(12) United States Patent
Trenkle et al.

(10) Patent No.: US 8,637,560 B2
(45) Date of Patent: Jan. 28, 2014

(54) IMIDAZOLIDINONE COMPOUNDS, METHODS TO INHIBIT DEUBIQUITINATION AND METHODS OF TREATMENT

(75) Inventors: William Trenkle, Bethesda, MD (US); Adrian Wiestner, Bethesda, MD (US); Qiuyan Wang, Bethesda, MD (US); Yihong Ye, Germantown, MD (US); Helena Mora-Jensen, Copenhagen (DK)

(73) Assignee: The United States of America as Represented by the Secretary of the Department of Health and Human Services, Washington, DC (US)

( * ) Notice: Subject to any disclaimer, the term of this patent is extended or adjusted under 35 U.S.C. 154(b) by 583 days.

(21) Appl. No.: 12/669,361

(22) PCT Filed: Jul. 18, 2008

(86) PCT No.: PCT/US2008/008797
§ 371 (c)(1),
(2), (4) Date: Jul. 20, 2010

(87) PCT Pub. No.: WO2009/011910
PCT Pub. Date: Jan. 22, 2009

(65) Prior Publication Data
US 2010/0286091 A1    Nov. 11, 2010

Related U.S. Application Data

(60) Provisional application No. 60/961,202, filed on Jul. 18, 2007.

(51) Int. Cl.
*A61K 31/4166* (2006.01)
*C07D 233/32* (2006.01)

(52) U.S. Cl.
USPC ............... 514/386; 548/311.1; 548/316.4

(58) Field of Classification Search
USPC ..................... 548/311.1, 316.4; 514/386
See application file for complete search history.

(56) References Cited

U.S. PATENT DOCUMENTS

| 2002/0091148 A1 | 7/2002 | Barnaung et al. |
| 2007/0037752 A1 | 2/2007 | Ansorge et al. |

FOREIGN PATENT DOCUMENTS

| WO | 9708150 A1 | 3/1997 |
| WO | 9736892 A1 | 10/1997 |
| WO | 0153297 A1 | 7/2001 |

OTHER PUBLICATIONS

Fiebiger, E. et al, "Dissection of the dislocation pathway for type I membrane proteins with a new small molecule inhibitor, Eeyarestatin." Molec. Bio. Cell, (2004), vol. 15, 1635-1646.*

Adams, J. (2004). The development of proteasome, inhibitors as anticancer drugs. Cancer Cell 5, 417-421.
Bays, N.W., Wilhovsky, S K., Goradia, A., Hodgkiss-Harlow, K., and Hampton, R.Y. (2001). HRD4/NPL4 Is Required for the Proteasomal Processing of Ubiquitinated ER Proteins. Mol Biol Cell 12, 4114-4128.
Bence, N.F., Bennett, E.J., and Kopito R.R. (2005). Application and Analysis of the GFP(u) Family of Ubiquitin-Proteasome System Reporters. Methods Enzymol 399, 481-490.
Blom, D., Hirsch C., Stern, P., Tortorella, D., and Ploegh, H.L. (2004). A glycosylated type I membrane protein becomes cytosolic when peptide: N-glycanase is compromised. Embo J 23, 650-658.
Boyce, M., Bryant, K., Jousse, C., Long, K., Harding, H., Scheuner, D. Kaufman, R., Ma, D., Coen, D., Ron, D., Yuan, J. (2005). A selective inhibitor of elF2alpha Dephosphorylation Protects Cells from ER Stress. Science, 307, 935-939.
Braun, S., Matuschewski, K., Rape, M., Thoms S., and Jentsch S. (2002). Role of the ubiquitin-selective CDC48 (UFD1/NPL4)chaperone (segregase) in ERAD of OLE1 and other substrates. Embo J 21, 615-621.
Burnett, B., Li, F., and Pittman, R.N. (2003). The polyglutamine neurodegenerative protein ataxin-3 binds poiyubiquitylated proteins and has ubiquitin protease activity. Hum Mol Genet 12, 3195-3205.
Carvalho, P., Goder, V., and Rapoport, T.A. (2006). Distinct ubiquitin-ligase complexes define convergent pathways for the degradation of ER proteins. Cell 126, 361-373.
Chen, X., Shen, J., and Prywes, R. (2002). The Luminal Domain of ATF6 Senses Endoplasmic Reticulum (ER) Stress and Causes Translocation of ATF6 from the ER to the Golgi. J Biol Chem 277, 13045-13052.
Degterev, A., Lugovskoy, A., Cardone, M., Mulley, B., Wagner, G , Mitchison, T., and Yuan, J. (2001). Identification of small-molecule inhibitors of interaction between the BH3 domain and Bcl-xL. Nature Cell Biology 3, 173-182.
DeLaBarre, B., Christianson, J.C., Kopito, R.R., and Brunger, A.T. (2006). Central pore residues mediate the p97/VCP activity required for ERAD. Mol Cell 22, 451-462.
Denic, V., Quan, E.M., and Weissman, J.S. (2006). A luminal surveillance complex that selects misfolded glycoproteins for ER-associated degradation. Cell 126, 349-359.
Fernandez, Y., Verhaegen, M., Miller, T P., Rush, J.L., Steiner. P , Opipari, Jr., A.W., Lowe, S.W., and Soengas, M.S. (2005). Differential Regulation of Noxa in Normal Melanocytes and Melanoma Cells by Protease Inhibition: Therapeutic Implications. Cancer Res. 65, 6294-6304.
Fiebiger, E., Hirsch, C., Vyas, J.M., Gordon, E., Pioegh, H.L., and Tortorella, D. (2004). Dissection of the dislocation pathway for type I membrane proteins with a new small molecule inhibitor, eeyarestatin. Mol Biol Cell 15, 1635-1646.
Fribley, A.M., Evenchik, B., Zeng, Q., Park, B.K., Guan, J.Y., Zhang, H, Hale, T.J., Soengas, M.S., Kaufman, R.J., and Wang, C.Y. (2006) Proteasome Inhibitor PS-341 Induces Apoptosis in Cisplatin-resistant Squamous Cell Carcinoma Cells by Induction of Noxa. J Biol Chem 281, 31440-31447.

(Continued)

Primary Examiner — Kamal Saeed
Assistant Examiner — Janet L Coppins
(74) Attorney, Agent, or Firm — Cantor Colburn LLP

(57) ABSTRACT

The present invention features imidazolidinone compounds and pharmaceutical compositions of imidazolidinone compounds. The compounds of the invention are utilized in methods of treating a deubiquitination-related disorder in a subject and inhibiting p97-associated deubiquitination.

18 Claims, 20 Drawing Sheets

(56) References Cited

OTHER PUBLICATIONS

Friedlander, R., Jarosch, E., Urban, J., Volkwein, C., and Sommer, T. (2000). A regulatory link between ER-associated protein degradation and the unfolded-protein response. Nat Cell Biol 2, 379-384, and Supplementary Information.

Gauss. P., Jarosch, E., Sommer, T. and Hirsch, C. (2006). A complex of Yos9p and the HRD ligase integrates endoplasmic reticulum quality control into the degradation machinery. Nat Cell Biol 8, 849-854.

Gomez-Bougie, P., Wuilleme-Toumie, S., Menoret, E., Trichet, V., Robillard, N., Philippe, M., Bataille, R., and Arriot, M. (2007). Noxa Up-regulation and Mcl-1 Cleavage Are Associated to Apoptosis Induction by Bortezomib in Multiple Myeloma. Cancer Res 67:11, 5418-5424.

Hampton, R.Y. (2002). ER-associated degradation in protein quality control and cellular regulation. Curr Opin Cell Biol 14, 476-482.

Haze, K., Yoshida, H., Yanagi, H., Yura, T., and Mori, K. (1999). Mammalian Transcription Factor ATF6 Is Synthesized as a Transmembrane Protein and Activated by Proteolysis in Response to Endoplasmic Reticulum Stress. Molecular Biology of the Cell 10, 3737-3799.

Hirsch, C., Blom. D., and Ploegh, H.L. (2003). A role for N-glycanase in the cytosolic turnover of glycoproteins Embo J 22, 1036-1046.

Hitchcock, A.L., Krebber, H., Fretze, S., Lin, A., Latterich, M., and Silver, P.A. (2001). The conserved npl4 protein complex mediates proteasome-dependent membrane-bound transcription factor activation Mol Biol Cell 12, 3226-3241.

Huppa, J.B., and Ploegh, H.L. (1997). The alpha chain of the T cell antigen receptor is degraded in the cytosol, Immunity 7, 113-122.

Kikkert, M., Hassink. G., Barel, M., Hirsch, C., van der Wal, F.J., and Wiertz, E. (2001). Ubiquitination is essential for human cytomegalovirus US11-mediated dislocation of MHC class I molecules from the endoplasmic reticulum to the cytosol. Biochem J 358, 369-377.

Lilley, B.N., and Ploegh, H.L. (2004). A membrane protein required for dislocation of misfolded proteins from the ER. Nature 429, 834-840.

Lilley, B.N., and Ploegh H.L. (2005a). Multiprotein complexes that link dislocation, ubiquitination, and extraction of misfolded proteins from the endoplasmic reticulum membrane. Proc Natl Acad Sci U S A 102, 14296-14301.

Liliey, B.N., and Ploegh, H.L. (2005b), Viral modulation of antigen presentation: manipulation of cellular targets in the ER and beyond. Immunol Rev 207, 126-144.

Meusser, B., Hirsch. C. Jarosch, E., and Sommer, T. (2005) ERAD: the long road to destruction. Nat Cell Biol 7, 766-772.

Neuber, O., Jarosch, E., Volkwein, C., Walter, J., and Sommer, T. (2005). Ubx2 links the Cdc48 complex to ER-associated protein degradation. Nat Cell Biol 7, 993-998 and Supplementary Information.

Ng, D.T., Spear, E.D., and Walter, P. (2000). The unfolded protein response regulates multiple aspects of secretory and membrane protein biogenesis and endoplasmic reticulum quality control. J Cell Biol 150, 77-88.

Nikiforov, M., Riblett, M., Tang, W.H., Gratchouck, V., Zhuang, D., Fernandez, Y., Verhaegen, M., Varambally, S., Chinnaiyan, A.M., Jakubowiak A.J., and Soengas, M.S. (2007). Tumor cell-selective regulation of NOXA by c-MYC in response to proteasome inhibition. PNAS 104, 19488-19493.

Oltersdorf, T., et al., An inhibitor of Bcl-2 family proteins induces regression of solid tumours. (2005) Nature 435, 677-681.

Perez-Galan, P., Roue, G., Villamor, N., Montserrat, E., Campo, E., and Colomier, D. (2006). The proteasome inhibitor bortezomib induces apoptosis in mantle-cell lymphoma through generation of ROS and Noxa activation independent of p53 status. Blood 107, 257-264.

Qin, J., et al., Proteasome Inhibitors Trigger NOXA-Mediated Apoptosis in Melanoma and Myeloma Cells. (2005) Cancer Res. 65, 6282-6293.

Rabinovich, E., Kerem, A., Frohlich, K.U., Diamant, N., and Bar-Nun, S. (2002). AAA-ATPase p97/Cdc48p, a Cytosolic Chaperone Required for Endoplasmic Reticulum-Associated Protein Degradation. Mol Cell Biol 22, 626-634.

Richly, H., Rape, M., Braun, S., Rumpf, S., Hoege, C., and Jentsch, S. (2005). A series of ubiquitin binding factors connects CDC48/p97 to substrate multiubiquitylation and proteasomal targeting. Cell 120, 73-84.

Rizzatti, E.C., Mora-Jensen, H., Weniger, M.A., Gibellini, F., Lee, E., Daibata, M., Lai, R., and Wiestner, A. Noxa mediates bortezomib induced apoptosis in both sensitive and intrinsically resistant mantel cell lymphoma cells and this effect is independent of constitutive activiey of AKT and NF-kappaB pathways. (2008). Leukemia & Lymphoma 49, 798-808.

Schuberth, C., and Buchberger, A. (2005). Membrane-bound Ubx2 recruits Cdc48 to ubiquitin ligases and their substrates to ensure efficient ER-associated protein degradation. Nat Cell Biol 7, 999-1006 and Supplementary Information 1-2.

Shamu, C.E., Flierman, D., Ploegh, H.L., Rapoport, T.A., and Chau, V. (2001). Polyubiquitination Is Required for US11-dependent Movement of MHC Class I Heavy Chain from Endoplasmic Reticulum into Cytosol. Mol Biol Cell 12, 2546-2555.

Shamu, C.E., Story, C.M., Rapoport, T.A., and Ploegh, H.L. (1999). The pathway of US11-dependent degradation of MHC class I heavy chains involves a ubiquitin-conjugated intermediate. J Cell Biol 147, 45-57.

Swanson, R., Locher, M., and Hochstrasser, M. (2001). A conserved ubiquitin ligase of the nuclear envelope/endoplasmic reticulum that functions in both ER-associated and Mat alpha 2 repressor degradation. Genes Dev 15, 2660-2674.

Taxis, C., Hitt, R., Park, S.H., Deak, P.M., Kostova, Z., and Wolf, D.H. (2003), Use of modular substrates demonstrates mechanistic diversity and reveals differences in chaperone requirement of ERAD. J Biol Chem 278, 35903-35913.

Travers, K.J., Patil, C.K., Wodicka, L., Lockhart, D.J., Weissman, J.S., and Walter, P. (2000). Functional and genomic anaylses reveal an essential coordination between the unfolded protein response and ER-associated degradation. Cell 101, 249-258.

Vashist, S., and Ng, D.T.W (2004). Misfolded proteins are sorted by a sequential checkpoint mechanism of ER quality control. J Cell Biol 165, 41-52.

Verma, R., Aravind, L., Oania R., McDonald, W.H., Yates, J. R., 3rd, Koonin, E.V., and Deshaies, R.J. (2002). Role of Rpn11 metalloprotease in deubiquitination and degradation by the 26S proteasome. Science 298, 611-615.

Wang, O., Li, L., and Ye, Y. (2006) Regulation of retrotranslocation by p97-associated deubiquitinating enzyme ataxin-3. J Cell Biol 174, 963-971.

Wiertz, E.J.H.J.; Jones; T.R., Sun, L.; Bogyo, M., Geuze, H.J., and Ploegh, H.L. (1996a). The human cytomegalovirus US11 gene product dislocates MHC class I heavy chains from the endoplasmic reticulum to the cytosol. Cell 84, 769-779.

Wiertz, E.J.H.J., Tortorella, D., Bogyo, M., Yu, J.; Mothes; W., Jones, T.R., Rapoport, T.A., and Ploegh, H.L. (1996b), Sec61-mediated transfer of a membrane protein. from the endoplasmic reticulum to the proteasome for destruction. Nature 384, 432-438.

Yao, T., and Cohen, R.E. (2002). A cryptic protease couples deubiquitination and degradation by the proteasome. Nature 419, 403-407 (abstract only).

Ye, Y. (2006). Diverse functions with a common regulator: ubiquitin takes command of an AAA ATPase. J Struct Biol 156, 29-40.

Ye, Y., Meyer. H.H., and Rapoport., T.A. (2001). The AAA ATPase Cdc48/p97 and its partners transport proteins from the ER into the cytosol. Nature 414, 652-656.

Ye, Y., Meyer, H.H., and Rapoport, (2003). Function of the p97-Ufd1-Npl4 complex in retrotranslocation from the ER to the cytosol: dual recognition of nonubiguitinated polypeptide segments and polyubiquitin chains. J Cell Biol 162, 71-84.

Ye, Y., Shibata, Y., Kikkert, M., van Voorden, S., Wiertz, E., and Rapoport, T.A. (2005). Recruitment of the p97 ATPase and ubiquitin ligases to the site of retrotranslocation at the endoplasmic reticulum membrane. PNAS 102, 14132-14138.

(56) References Cited

OTHER PUBLICATIONS

Ye, Y., Shibata, Y., Yun, C, Ron, D. and Rapoport, T.A. (2004). A membrane protein complex mediates retro-translocation from the ER lumen into the cytosol. Nature 429, 841-847.

Yu H., and Kopito, R.R. (1999). The role of multiubiquitination in dislocation and degradation of the alpha subunit of the T cell antigen receptor. J Biol Chem 274, 36852-36858.

Zhong, X., and Pittman, R.N. (2006). Ataxin-3 binds VCP/p97 and regulates retrotranslocation of ERAD substrates. Hum Mol Genet 15, 2409-2420.

Zhong, X., Shen, Y., Ballar, P., Apostolou, A., Agami, R., and Fang, S. (2004). AAA ATPase p97/valosin-containing protein interacts with gp78, a ubiquitin ligase for endoplasmic reticulum-associated degradation. J Biol Chem 279, 45676-45684.

Yao, T., et al. (2006). Proteasome recruitment and activation of the Uch37 deubiquitnating enzyme by Adrm1. Nature Cell Biology 8, 994-1002.

Lipson et al. "A Proteasomal ATPase Contributes to Dislocation of Endoplasmic Reticulum-associated Degradation (ERAD) Substrates" The Journal of Biological Chemistry; vol. 283; No. 11; pp. 7166-7175; Mar. 14, 2008.

Hein et al., "Untersuchung Uber Die Wirkung von nitrofuryl-propenyliden-benzhydraz Iden Gegenuber Trichomonaden, Bakterien, Hefen und Pilzen Unter besonderer Berucksichtigung der Ergebnisse im Ames-Test und Host-Medicated Assay" Arzeimittel Forschung. Drug Research, ECV Editio Cantor Verlag, Aulendorf, vol. 33; No. 3; Jan. 1, 1983; pp. 363-369. (English Summary provided on p. 363).

Jentsch et al. "Cdc48 (p97): A "Molecular Gearbox" in The Ubiquitin Pathway?" Trends in Biochemical Sciences, vol. 32, No. 1, Jan. 2007; pp. 6-11.

International Preliminary Report on Patentability and Search Report of the International Searching Authority for International Patent No. PCT/US2008/008797; International Filing Date: Jul. 18, 2008; Date of Mailing: Mar. 9, 2009.

Search Report of the International Searching Authority for International Patent No. PCT/US2008/008797; International Filing Date: Jul. 18, 2008; Date of Mailing: Mar. 9, 2009.

Wang et al. "Inhibition of P97-Dependent Protein Degradation by Eeyarestatin I" The Journal of Biological Chemistry. vol. 283, No. 12, Mar. 2008; pp. 7445-7454.

Wang et al., "Molecular perspectives on p97-VCP: Progress in Understanding its Structure and Diverse Biological Functions", Journal of Structural Biology, vol. 146; 2004; pp. 44-57.

\* cited by examiner

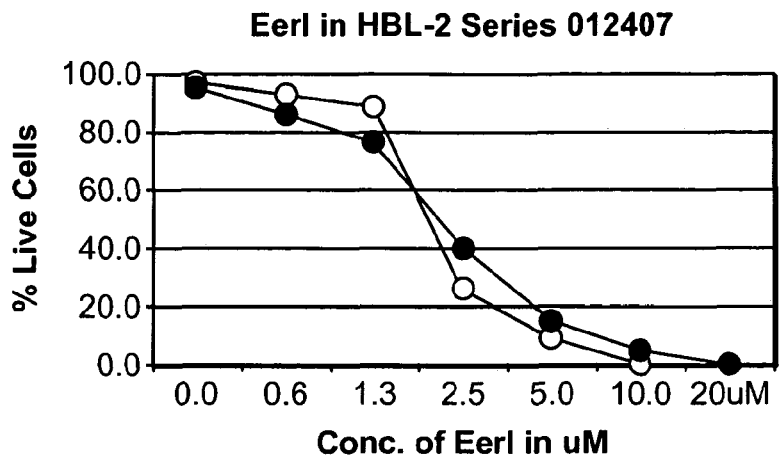
FIG. 1A
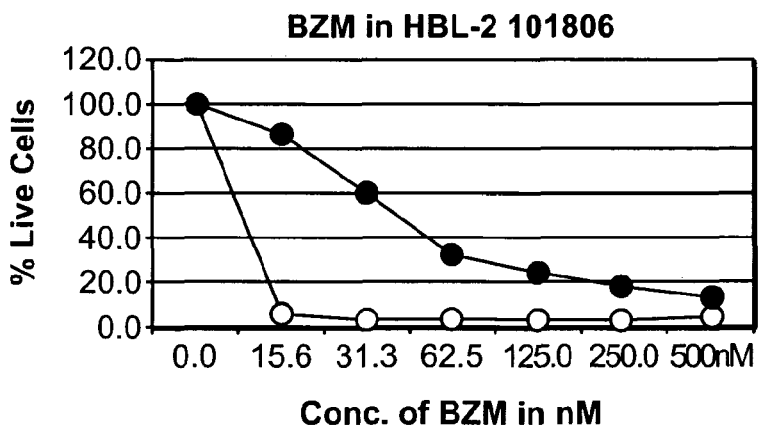
FIG. 1B
| HBL-2 | IC50 7M nM | IC50 FFR-1 |
|---|---|---|
| parental | ~5 | 2.07 |
| BR100 | 45.3 | 2.23 |
FIG. 1C

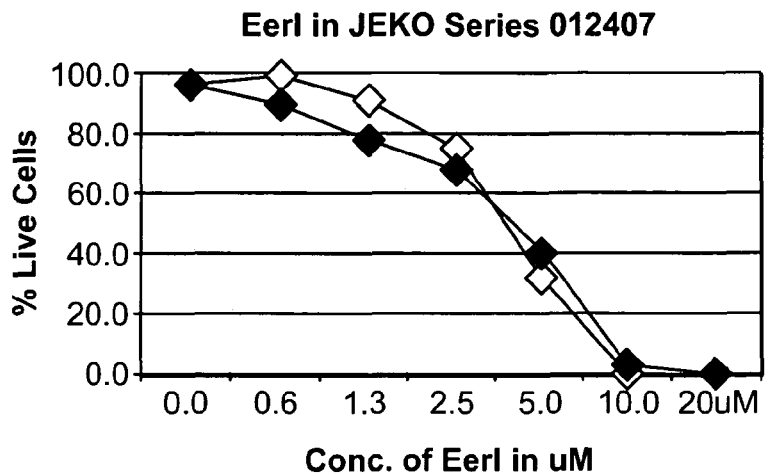
FIG 2A
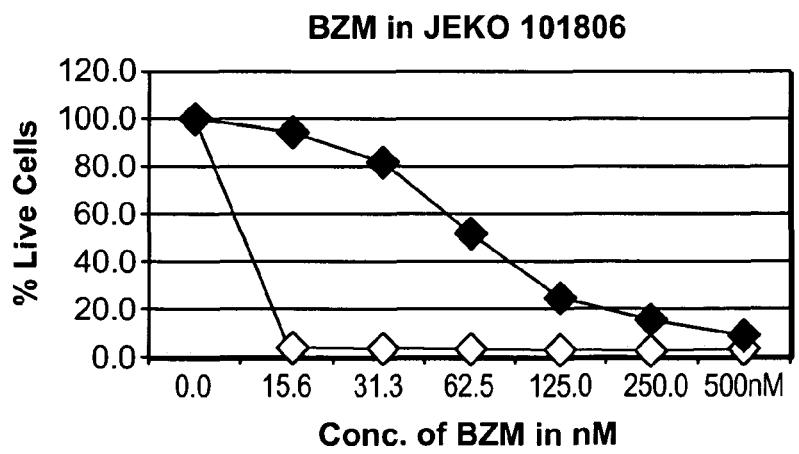
FIG 2B
| Jeko | IC50 7M nM | IC50 FFR-1 |
|---|---|---|
| parental | 8.1 | 3.72 |
| BR100 | 47.4 | 3.67 |
FIG 2C

| Sample | IC50 EER-1 uM |
|---|---|
| 2506 (CLL) | 1.4 |
| 4060 (CLL) | 1.6 |
| 2513 (PBMC) | 6 |
| 4171 (PBMC) | 11.4 |

| Sample | IC50 BZM nM |
|---|---|
| 2506 (CLL) | 80 |
| 4060 (CLL) | 100 |
| 2513 (PBMC) | 160 |
| 4171 (PBMC) | >200 |

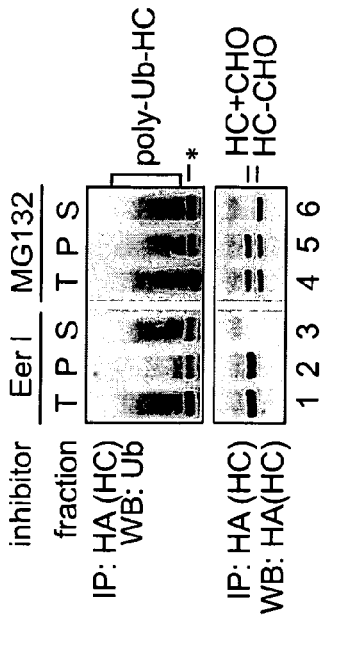
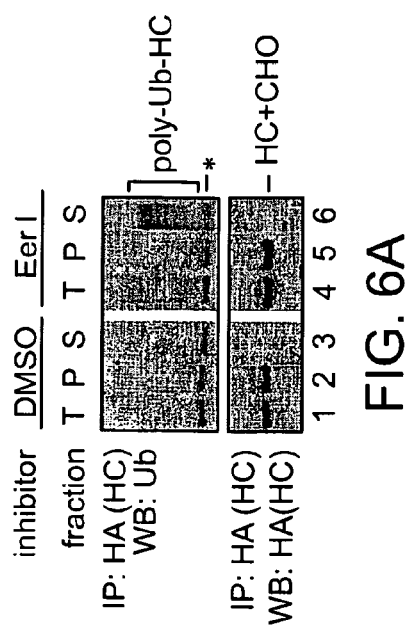
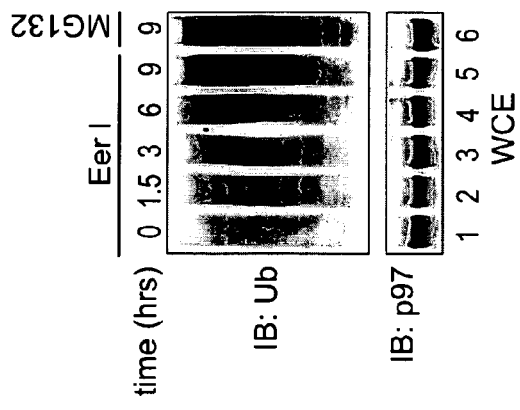
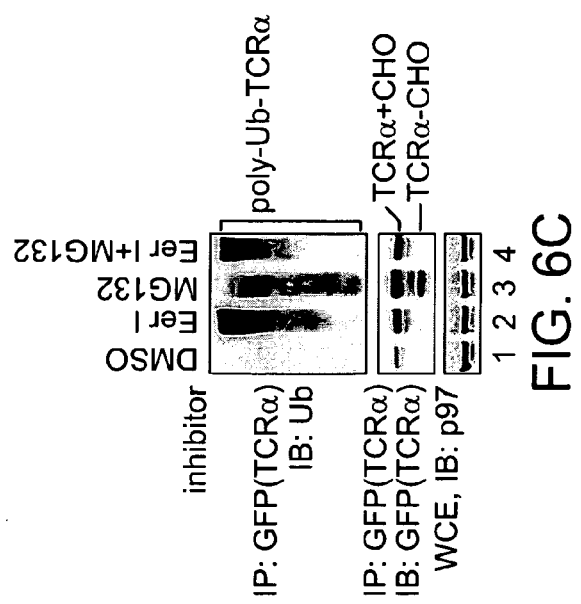
FIG. 6A
FIG. 6B
FIG. 6C
FIG. 6D

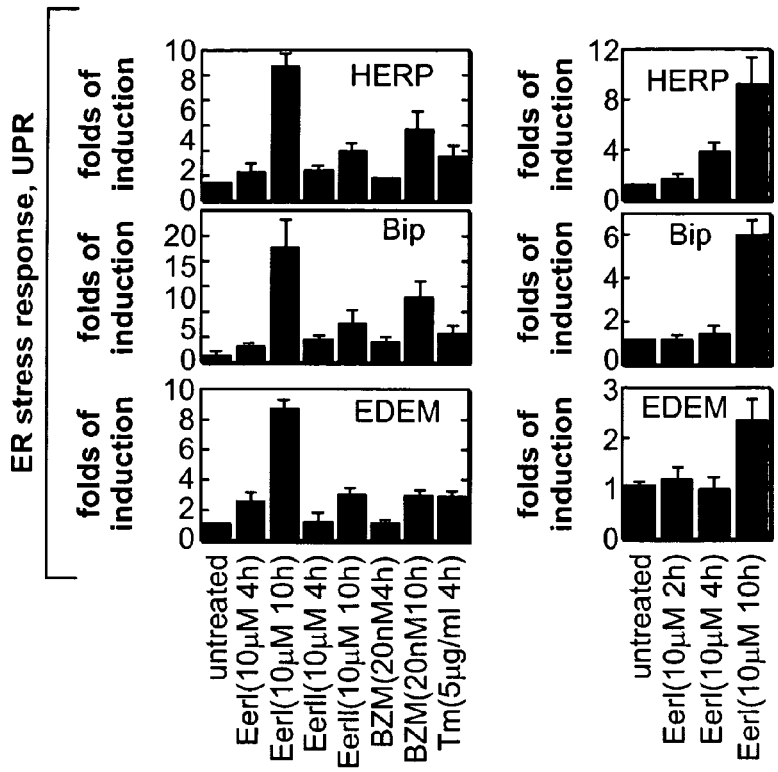
FIG. 13B
FIG. 14
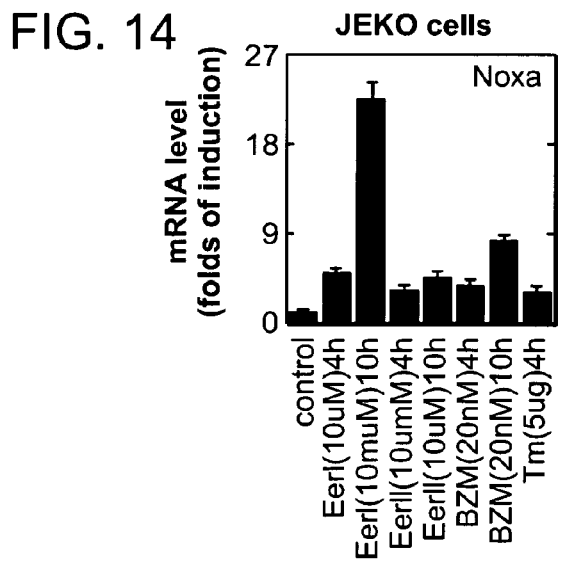
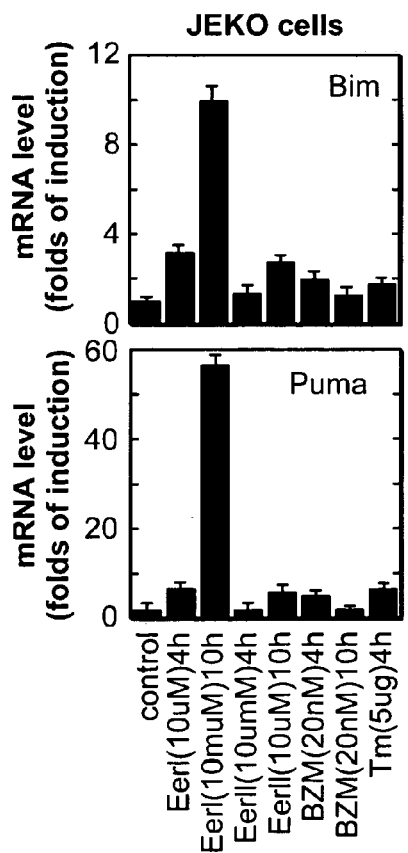

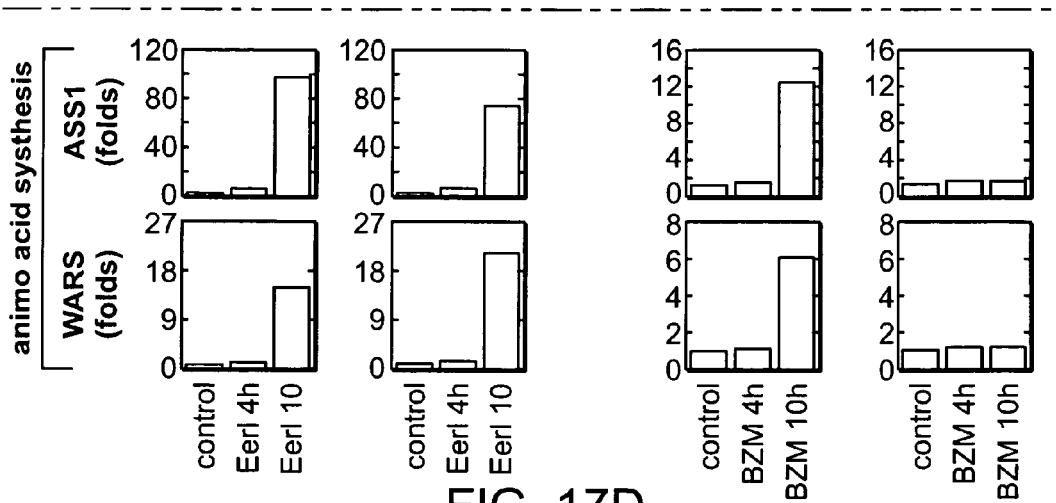
FIG. 17D
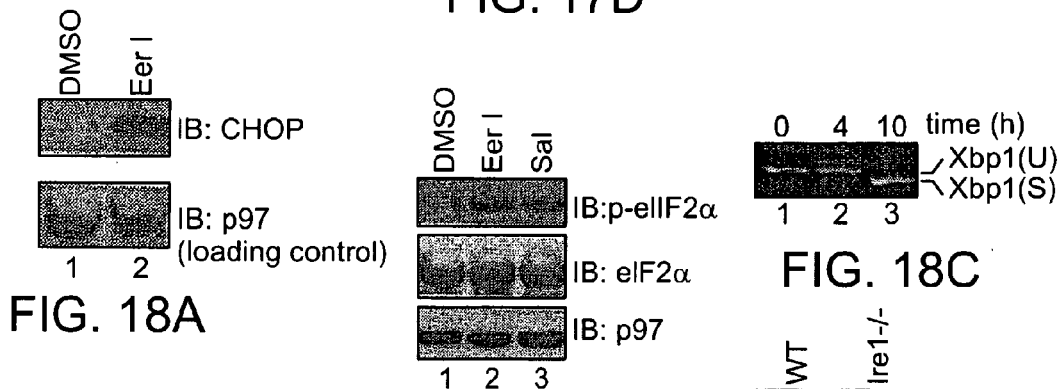
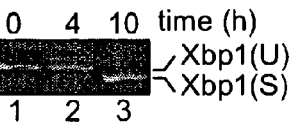
FIG. 18A
FIG. 18B
FIG. 18C
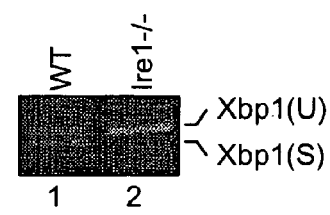
FIG. 18D
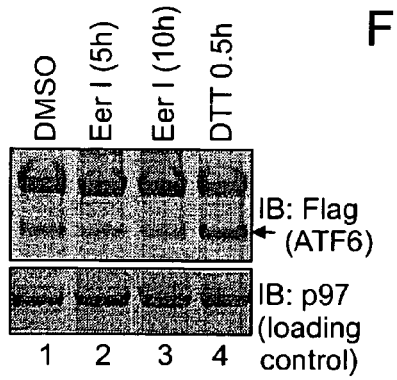
FIG. 18E
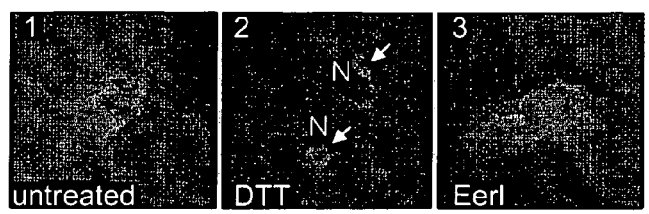
FIG. 18F

IMIDAZOLIDINONE COMPOUNDS, METHODS TO INHIBIT DEUBIQUITINATION AND METHODS OF TREATMENT

This application claims the benefit of U.S. Provisional Patent Application Ser. No. 60/961,202 filed Jun. 18, 2007, and to PCT/US08/008,9787, filed Jun. 18, 2008, both of which is are hereby incorporated by reference herein in its their entirety.

GOVERNMENT SUPPORT

Research supporting this application was carried out by the United States of America as represented by the Secretary, Department of Health and Human Services.

BACKGROUND OF THE INVENTION

Ubiquitin-mediated proteolysis is an important pathway of non-lysosomal protein degradation that controls the timed destruction of many cellular regulatory proteins. Ubiquitin is an evolutionarily highly conserved 76-amino acid polypeptide which is abundantly present in eukaryotic cells. The ubiquitin pathway leads to the covalent attachment of polyubiquitin chains to target substrates which are then degraded by a multi-catalytic proteasome complex. In addition to its role in proteasomal degradation of target proteins, the ubiquitin system is also involved in a number of cellular processes unrelated to proteasomal degradation including endocytosis, trafficking in the endosomal system, viral budding, DNA repair, nucleocytoplasmic trafficking and kinase activation.

A number of the steps that regulate protein ubiquitination are known. In particular, initially the ubiquitin activating enzyme (E1) forms a high energy thioester linkage with ubiquitin. Ubiquitin is then transferred to a reactive cysteine residue of one of many ubiquitin conjugating enzymes known as Ubc or ubiquitin E2 enzymes. The final transfer of ubiquitin to a target protein involves one of many ubiquitin protein ligases (E3s).

In eukaryotic cells the ubiquitin proteasome system (UPS) plays an important role in many protein quality control pathways, including the elimination of misfolded proteins from the endoplasmic reticulum (ER) (Hampton, Curr Opin Cell Biol 14, 476-482.2002; Meusser et al., 2005). The UPS dependent degradation of misfolded ER proteins by the so called ERAD pathway (ER-associated protein degradation) adapts cells to stress conditions that would other wise disturb ER homeostasis and cause programmed cell death. An inhibitor of ER-associated protein degradation called Eeyarestatin I (EERI) was recently identified, but the mechanism of its action is unclear (Fiebiger et al., 2004).

To degrade misfolded ER proteins, terminally misfolded polypeptides (both membrane and soluble substrates) are recognized by chaperones, and targeted to the export sites at the ER membrane. Polypeptides are subsequently transferred across the membrane via an unknown conduit to enter the cytosol where they become substrates of the UPS (Friedlander et al., 2000; Ng et al., 2000; Travers et al., 2000). Interestingly, the retrotranslocation pathway can be hijacked by certain viruses to downregulate the expression of correctly folded cellular proteins involved in the immune defense of cells, allowing these viruses to propagate without being detected by the cytotoxic T cells (Lilley and Ploegh, 2005b). For example, either of the two proteins (US11 and US2) encoded by human cytomegalovirus (HCMV) is able to induce rapid dislocation and degradation of newly synthesized MHC class I heavy chains (Wiertz et al., 1996a; Wiertz et al., 1996b).

Because polypeptides can adopt a variety of incorrectly folded states, different misfolded proteins are likely to be distinguished by discrete mechanisms. Genetic studies in yeast have uncovered at least two routes by which misfolded proteins can be selected to undergo retrotranslocation (Swanson et al., 2001; Taxis et al., 2003; Vashist and Ng, 2004). Recent biochemical analyses have identified molecular constituents that account for the mechanistic differences of these pathways. It appears that substrates containing lesions in their luminal domains (ERAD-L substrates) are recognized by chaperones such as Kar2p, Yos9p, and Htm1p/Mn11p, and are targeted to a membrane complex that contains proteins including Der1p, Usa1p, Hrd3p, and the ubiquitin ligase Hrd1p (Carvalho et al., 2006; Denic et al., 2006; Gauss et al., 2006). On the other hand, proteins carrying misfolding signals in their cytosolic domains (ERAD-C substrates) are disposed of by a different set of factors associated with another ubiquitin ligase Doa10p (Carvalho et al., 2006).

When substrates leave the ER, these pathways merge at a highly conserved AAA ATPase (ATPase associated with various cellular activities) termed Cdc48p in yeast or p97/VCP in mammals (Ye, 2006). In mammalian cells, p97 is recruited to the ER membrane via association with two membrane proteins, Derlin and VIMP (Lilley and Ploegh, 2004; Ye et al., 2004; Lilley and Ploegh, 2005a; Ye et al., 2005); whereas in yeast, the link of Cdc48p to the ER membrane is provided by Ubx2p (Neuber et al., 2005; Schuberth and Buchberger, 2005). With the assistance of a dimeric cofactor, Ufd1-Np14, Cdc48p/p97 acts on both ERAD-L and ERAD-C substrates to extract them from the membrane once these substrates are polyubiquitinated (Bays et al., 2001; Hitchcock et al., 2001; Ye et al., 2001; Braun et al., 2002; Rabinovich et al., 2002; Ye et al., 2003; Zhong et al., 2004).

In the next step, substrates dislocated by p97 need to be delivered to the proteasome, which likely occurs in a tightly coupled manner at the ER membrane with the help of some shuttling factors. It was proposed that several ubiquitin binding proteins including a p97-bound ubiquitin ligase Ufd2 and the proteasome-associated factor Rad23 may form a ubiquitin receiving chain to hand over polyubiquitinated substrates to the proteasome (Richly et al., 2005). The degradation of many ERAD substrates also involves a p97-interacting deubiquitinating enzyme (DUB) named ataxin-3 (atx3), which may be part of the substrate delivery system (Wang et al., 2006). The atx3-mediated deubiquitinating reaction appears to act on many misfolded substrates to facilitate their degradation. In the absence of p97-associated deubiquitnation, polyubiquitinated substrates are transferred to the proteasome, but remain intact as proteasome bound species.

Cdc48/p97 not only plays a central role in the ERAD pathway, it is also involved in many other ubiquitin dependent biological processes including cell cycle regulation, transcription control, membrane fusion, protein trafficking et al. (for review see Ye 2005). The p97 ATPase is one of the most abundant proteins in the cytosol (estimated to constitute 1% of the total cytosolic proteins), which is able to interact with various cofactors in a mutually exclusive manner. p97 can act either in conjunction with the proteasome to promote protein turnover, or independently to alter the activity of its substrates. Interestingly, both the proteolytic and non-proteolytic functions of p97 seem to involve ubiquitin one way or the other. Thus, it is generally believed that various p97 cofactors can engage the same ATPase to act on different ubiquitin-modified substrates, which would lead to discrete functional consequences. Intriguingly, several of the identified p97-cofactors are deubiquitinating enzymes, raising the possibility that p97-associated deubiquitination may be essential for its function in various cellular processes.

The development of cancer can depend on the accumulation of specific genetic alterations that allow aberrant cell proliferation, including growth of tumor cells. Ubiquitin is often attached to a substrate as a chain by a process termed polyubiquitination. Polyubiquitination marks the modified protein for degradation through the proteasome. Additionally, ubiquitination can alter the functional state of substrates. p97 is a ubiquitin selective chaperone that regulates many ubiquitin dependent cellular processes critical for cell viability. Compounds that disturb the ubiquitin pathways affect cell growth and other cellular functions. The ubiquitin-proteasome system is recognized to play a large role in tumor biology.

It thus would be desirable to have new compounds that have use in the treatment of undesired cell proliferation, including treatment against cancer cells, as well as for treatment against viral infections. It would be especially desirable to have new compounds that could inhibit p97 functions, including its associated deubiquitinating activities.

SUMMARY OF THE INVENTION

In one aspect, the invention provides a method of treating a deubiquitination-related disorder in a subject, comprising administering to said subject in need thereof, an effective amount of an imidazolidinone compound.

In other aspects, the invention provides a method of treating cancer in a subject identified as in need of such treatment, the method comprising administering to said subject an effective amount of a compound of formula I:

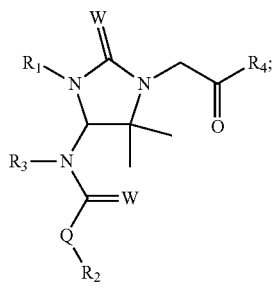

Formula I wherein
  each occurrence of W is independently O, S, or $NR_A$;
  Q is O, S, or $NR_A$;
  $R_1$ is selected from hydrogen, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted haloalkyl, optionally substituted alkoxy, optionally substituted cycloalkoxy, optionally substituted (cycloalkyl)alkoxy, or optionally substituted heterocycloalkyl;
  $R_2$ is selected from hydrogen, optionally substituted alkyl, optionally substituted cycloalkyl, optionally substituted aryl, optionally substituted heteroaryl, optionally substituted haloalkyl, optionally substituted alkoxy, optionally substituted cycloalkoxy, optionally substituted (cycloalkyl)alkoxy, or optionally substituted heterocycloalkyl;
  $R_3$ is selected from hydrogen or hydroxyl;
  $R_4$ is X—Y—Z;
  wherein X is O, S, or $NR_B$;
  Y is alkyl, alkenyl, or alkynyl, each of which may be substituted with a heteroatom; wherein at least one carbon of each alkyl, alkenyl, or alkynyl may be substituted by a heteroatom;
  Z is an optionally substituted aryl or an optionally substituted heteroaryl;
  each $R_A$ is independently selected from hydrogen, optionally substituted alkyl, optionally substituted aryl, or optionally substituted heteroaryl; and
  $R_B$ is selected from hydrogen or optionally substituted alkyl.

In another aspect, the invention provides a method of treating a subject suffering from or susceptible to viral infection comprising administering to the subject an effective amount an imidazolidinone compound.

In another aspect, the invention provides a method of inhibiting p97-associated deubiquitination in a subject, the method comprising the step of administering to the subject one or more compounds of Formula I:

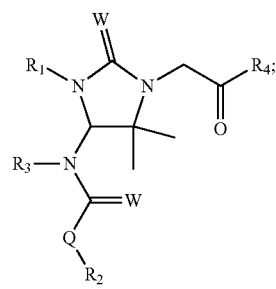

Formula I wherein
  each occurrence of W is independently O, S, or $NR_A$;
  Q is O, S, or $NR_A$;
  $R_1$ is selected from hydrogen, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted haloalkyl, optionally substituted alkoxy, optionally substituted cycloalkoxy, optionally substituted (cycloalkyl)alkoxy, or optionally substituted heterocycloalkyl;
  $R_2$ is selected from hydrogen, optionally substituted alkyl, optionally substituted cycloalkyl, optionally substituted aryl, optionally substituted heteroaryl, optionally substituted haloalkyl, optionally substituted alkoxy, optionally substituted cycloalkoxy, optionally substituted (cycloalkyl)alkoxy, or optionally substituted heterocycloalkyl;
  $R_3$ is selected from hydrogen or hydroxyl;
  $R_4$ is X—Y—Z;
  wherein X is O, S, or $NR_B$;
  Y is alkyl, alkenyl, or alkynyl, each of which may be substituted with a heteroatom; wherein at least one carbon of each alkyl, alkenyl, or alkynyl may be substituted by a heteroatom;
  Z is an optionally substituted aryl or an optionally substituted heteroaryl;
  each $R_A$ is independently selected from hydrogen, optionally substituted alkyl, optionally substituted aryl, or optionally substituted heteroaryl; and
  $R_B$ is selected from hydrogen or optionally substituted alkyl;

in an amount and under conditions sufficient to inhibit p97-associated deubiquitination.

In still another aspect, the invention provides a method of modulating p97-associated deubiquitination in a cell, the method comprising the step of administering to the subject one or more compounds of Formula I in an amount and under conditions sufficient to modulate p97-associated deubiquitination.

In yet another aspect, the invention provides a compound having formula (III)

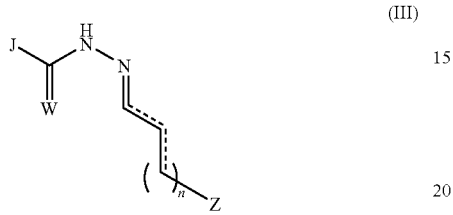

(III)

Wherein
W is O, S, or $NR_4$;
J is optionally substituted aryl, optionally substituted arylalkyl, optionally substituted alkyloxy, optionally substituted aryloxy, optionally substituted arylthio, optionally substituted alkylthio, optionally substituted arylamino, optionally substituted alkylamino, optionally substituted arylalkoxy, optionally substituted arylalkylthio, optionally substituted arylalkylamino, optionally substituted heteroaryl;
Z is an optionally substituted aryl or an optionally substituted heteroaryl; and
n is 0-3.

In certain aspects of the invention, the invention provides a compound having formula (III) in which Z is optionally substituted furan or nitrofuran. In other aspects of the invention, the invention provides a compound having formula (III) in which Y is phenyl or benzyloxy In another aspect, the invention provides a process for preparing a compound of formula (III)

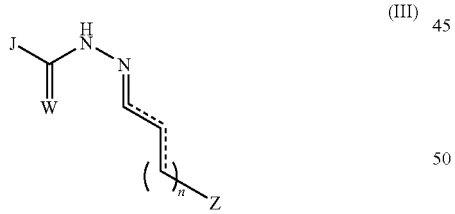

(III)

Wherein
W is O, S, or $NR_4$;
J is optionally substituted aryl, optionally substituted arylalkyl, optionally substituted alkyloxy, optionally substituted aryloxy, optionally substituted arylthio, optionally substituted alkylthio, optionally substituted arylamino, optionally substituted alkylamino, optionally substituted arylalkoxy, optionally substituted arylalkylthio, optionally substituted arylalkylamino, optionally substituted heteroaryl;
Z is an optionally substituted aryl or an optionally substituted heteroaryl; and
n is 0-3;
comprising the step of: reacting a compound of the formula:

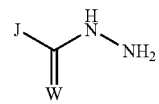

(IV)

wherein
W and J are as defined above
with a compound of the formula:

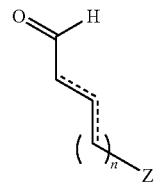

(V)

wherein
Z and n are as defined above
to produce a compound of formula (III).

In another aspect, the invention provides a process for preparing a compound of formula (II), in which Q is NH and $R_1$=$R_2$, comprising the steps of
a.) Reacting a compound of the formula (VI):

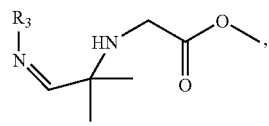

(VI)

with a compound of the formula (VII):

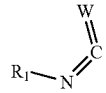

(VII)

and a compound of the formula (VIIa):

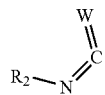

(VIIa)

wherein each occurrence of W may be the same or different and wherein $R_1$ and $R_2$ may be the same or different, to produce a compound of the formula (VIII):

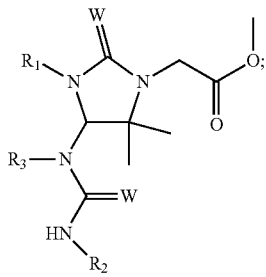

b) hydrazinolyzing the compound of formula (VIII) of step a); and c) reacting the product of step b) with a compound of the formula (V):

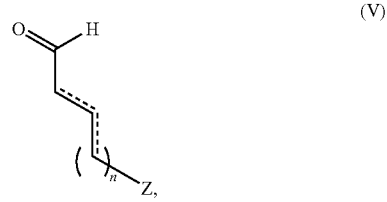

to produce a compound of formula (II).

In still another aspect, the invention provides method of treating a deubiquitination-related disorder in a subject, comprising administering to said subject in need thereof, an effective amount of an a compound of Formula (III), or pharmaceutically acceptable salt, solvate or hydrate thereof.

In another aspect, the invention provides a method of treating a subject suffering from or susceptible to viral infection comprising administering to the subject an effective amount a compound of Formula (III)

In other aspects, the invention provides a method of treating cancer in a subject identified as in need of such treatment, the method comprising administering to said subject an effective amount of a compound of formula III.

BRIEF DESCRIPTION OF THE DRAWINGS

FIG. 1A shows that EERI is equally potent against the bortezomib (BZM)-resistant cell line HBL-2 BR100 (black circle) as in the parental, bortezomib sensitive cell line (white circle). FIG. 1B shows the activity of bortezomib (BZM) against the bortezomib (BZM)-resistant cell line HBL-2 BR100 (black circle) and the parental, bortezomib sensitive cell line (white circle). FIG. 1C provides the $IC_{50}$ data of both EERI and bortezomib in the bortezomib-sensitive parental HBL-2 cell line and in the bortezomib-resistant HBL-2 BR100 cell line.

FIG. 2A shows that EERI is equally potent against the bortezomib (BZM)-resistant cell line Jeko BR100 (black diamond) as in the parental, bortezomib sensitive cell line (white diamond). FIG. 2B shows the activity of bortezomib against the bortezomib (BZM)-resistant cell line Jeko BR100 (black diamond) and the parental, bortezomib sensitive cell line (white diamond). FIG. 2C provides the $IC_{50}$ data of both EERI and bortezomib in the bortezomib-sensitive parental HBL-2 cell line and in the bortezomib-resistant HBL-2 BR100 cell line.

FIGS. 1-5 indicate that EERI is active against different hematologic tumor cell lines, remains active against bortezomib resistant MCL cell lines, is highly active against primary CLL cells, is non-toxic to normal blood cells at concentrations toxic to tumor cells, and synergizes with bortezomib against MCL cell lines.

FIG. 6 shows the accumulation of polyubiquitinated proteins in EerI-treated cells. (A) EerI treatment leads to an accumulation of polyubiquitinated heavy chain (HC) in the cytosol. A9 cells were treated with either DMSO or EerI (10 µM) (14 h), and permeabilized with the detergent, digitonin. A portion of the cells was solubilized directly (T), whereas the rest of each sample was fractionated into a pellet (P) and a supernatant fraction (S). HC was immunoprecipitated (IP) with anti-HA antibodies and analyzed by immunoblotting (IB). (HC+CHO, glycosylated HC; HC−CHO, deglycosylated HC; asterisk, a non-specific protein cross-reacting with the ubiquitin antibodies) (B) As in A, except that A9 cells treated with either EerI or the proteasome inhibitor MG132 (10 µM) were analyzed. (C) Accumulation of polyubiquitinated TCRα in EerI-treated cells. Where as indicated, TCRα-GFP expressing cells were treated with both EerI and MG132 (TCRα+CHO, glycosylated TCRα; TCRα−CHO, deglycosylated TCRα). A fraction of the extracts (WCE, whole cell extract) was analyzed directly by immunoblotting. (D) Accumulation of polyubiquitinated proteins in EerI-treated cells. Detergent extracts of 293T cells treated with the indicated compounds were analyzed by immunoblotting.

FIG. 14 shows that EERI induced the expression of several BH3-domain protein (Bim, Puma, Noxa) that can induce programmed cell death. FIG. 14 shows that the mRNA expression of several BH3-domain containing proteins including Noxa, Bim and Puma are all significantly induced by EerI treatment in JEKO cells. The experiments were carried out essentially as those shown in FIG. 13. Since these BH3 proteins are pro-apoptotic factors, their induction may explain the cell killing effect of EerI. Please note that BZM only induces the expression of Noxa, whereas EerI affects all of them, suggesting that EerI is a more effective therapeutic, including for use in cancer therapy.

FIGS. 6-10 show that EERI causes the accumulation of polyubiquitinated proteins in cells due to a defect in deubiquitination. Additionally, EERI inhibits p97 associate deubiquitination. The p97-associated deubiquitinating enzyme atx3 was identified as one of the target for EERI. Since all previously identified deubiquitination inhibitors including ubiquitin aldehyde are only effective in vitro due to a permeability problem, EERI is the first deubiquitinating inhibitor that blocks at least a subset of deubiquitinating activities in intact cells.

FIG. 11 demonstrates that EERI can have anti-retrovirus activity. In addition, EERI treatment elicits strong ER stress response that overlaps significantly with that induced by bortezomib, which explains the synergistic effect of the two compounds in killing cancer cells. Moreover, the expression of several proapoptotic BH3 domain containing proteins are highly induced by EERI, indicating that EERI may be used in combination with Bcl2 inhibitors, which has been demonstrated to induce the regression of certain tumors by activating the BH3 domain containing proapoptotic factors (Oltersdorf T., et al., 2005).

FIG. 18 shows that EerI activates the ATF4 and Ire1 branches of the UPR pathways—(A) EerI induces the expression of CHOP. Cell extracts from the indicated JEKO-1 cells were analyzed by immunoblotting. (B) EerI induces phosphorylation of eIF2α. Protein extracts from JEKO-1 cells untreated or treated with EerI were analyzed by immunoblotting with antibodies against the indicated proteins. As a control, we treated cells with Salubrinal (Sal), a phophatase inhibitor that promotes eIF2α phosphorylation (Boyce et al., 2005). (C, D) EerI induces the Ire1 dependent splicing of Xbp1 mRNA. (C) Total RNA from JEKO-1 cells treated with EerI for the indicated time points was subjected to analysis by RT-PCR. (D) RNA from EerI-treated wild type and Ire1α−/− MEF cells was analyzed as in (C). (E, F) EerI does not activate ATF6. (E) HeLa cells expressing Flag-tagged ATF6 were treated with the indicated chemicals. Cell extracts were analyzed by immunoblotting. (F) HeLa cells expressing Flag-tagged ATF6 were treated with the indicated chemicals and stained with Flag antibodies. N, nucleus. Arrows indicate the position of the Golgi.

DETAILED DESCRIPTION

Definitions

Figures 3A, 3B:
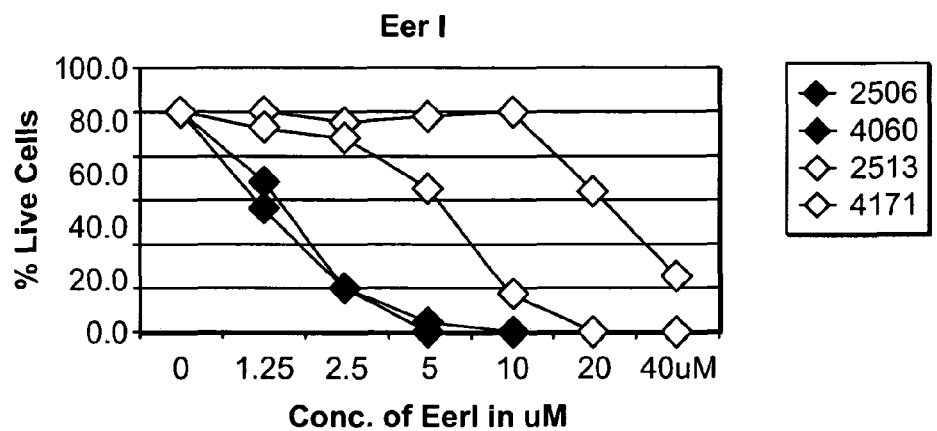
FIG. 3A shows the activity of EERI on primary CLL cells (black diamonds) and on normal peripheral blood mononuclear cells (PBMC, white diamonds).
FIG. 3B provides the IC50 data of EERI on CLL and PBMC samples.
Figures 4A, 4B:
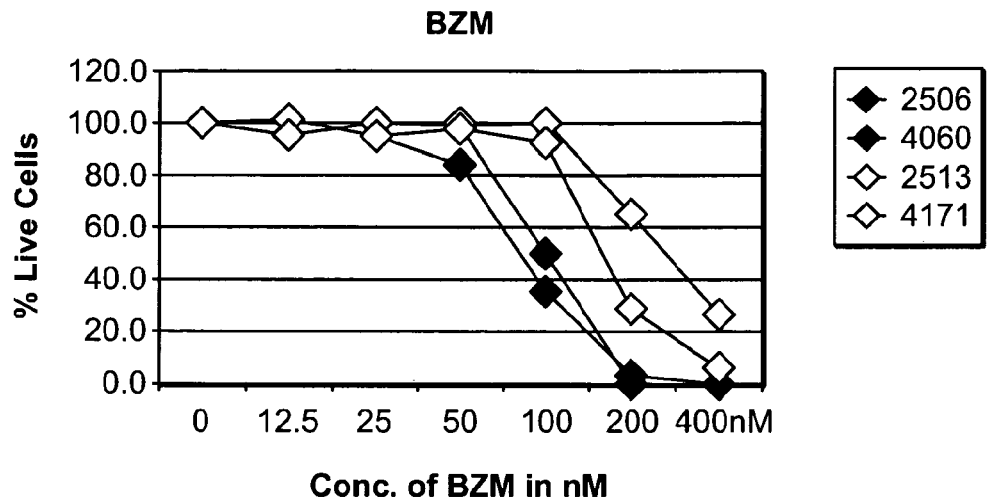
FIG. 4A shows the activity of bortezomib on primary CLL cells (black diamonds) and on normal peripheral blood mononuclear cells (white diamonds).
FIG. 4B provides the $IC_{50}$ data of bortezomib on CLL and PBMC. The data shows that EERI provides a better therapeutic window than bortezomib.
Figure 5A:
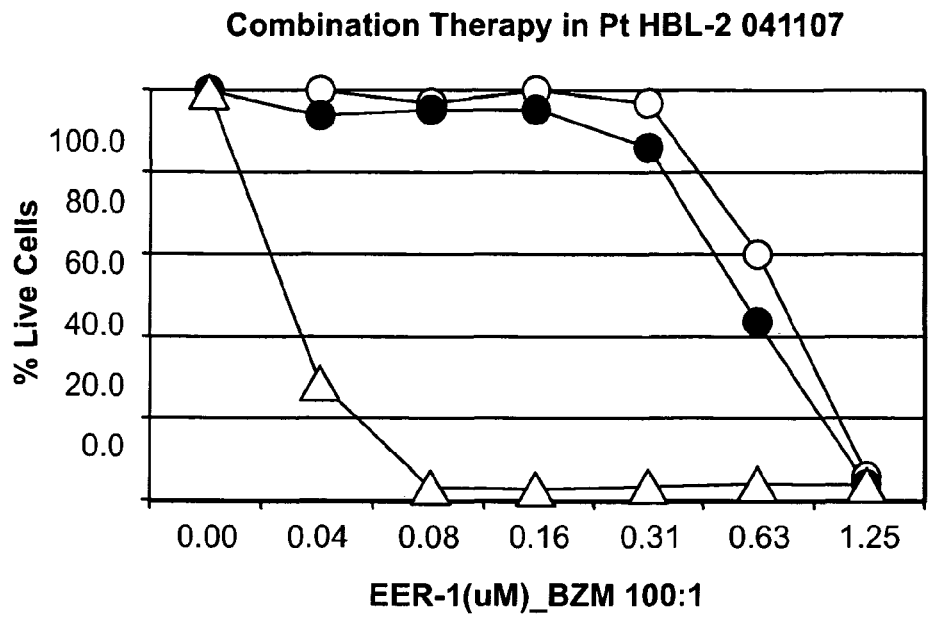
FIG. 5A shows the synergistic effects of EERI (black circle), BZM (white circle) and the combination of both (white triangle) on the parental bortezomib-sensitive cell line HBL-2. The CI (combination index) is 0.08 at IC50 and 0.06 at IC90. The CI thereby is a measure of synergy: <1 indicating that synergy exists.
Figure 5B:
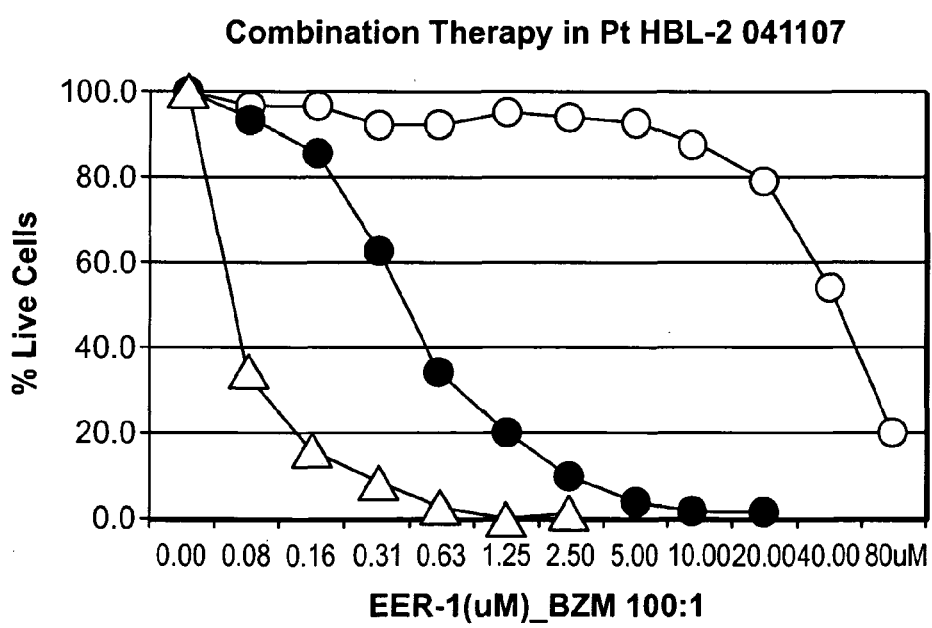
FIG. 5B shows the synergistic effects of EERI (black circle), BZM (white circle) and the combination of both (white triangle) on the bortezomib-resistant cell line HBL-2 BR100. The CI is 0.06 at IC50 and 0.04 at IC90. The CI (combination index) is a measure of synergy: <1 indicating that synergy exists.

As used herein, the term "alkyl" refers to a straight-chained or branched hydrocarbon group containing 1 to 12 carbon atoms. The term "lower alkyl" refers to a $C_1$-$C_6$ alkyl chain. Examples of alkyl groups include methyl, ethyl, n-propyl, isopropyl, tert-butyl, and n-pentyl. Alkyl groups may be optionally substituted with one or more substituents.

The term "alkenyl" refers to an unsaturated hydrocarbon chain that may be a straight chain or branched chain, containing 2 to 12 carbon atoms and at least one carbon-carbon double bond. Alkenyl groups may be optionally substituted with one or more substituents.

The term "alkynyl" refers to an unsaturated hydrocarbon chain that may be a straight chain or branched chain, containing the 2 to 12 carbon atoms and at least one carbon-carbon triple bond. Alkynyl groups may be optionally substituted with one or more substituents.

The $sp^2$ or sp carbons of an alkenyl group and an alkynyl group, respectively, may optionally be the point of attachment of the alkenyl or alkynyl groups.

The term "alkoxy" refers to an —O-alkyl radical. The term "ester" refers to a —C(O)O—R., where R is defined herein. An "amido" is an —C(O)NH$_2$, and an "N-alkyl-substituted amido" is of the formula C(O)NHR, where R is defined herein. The term "mercapto" refers to a —SH group. The term "alkylthio" refers to an —S-alkyl radical.

As used herein, the term "halogen" or "halo" means —F, —Cl, —Br or —I.

As used herein, the term "haloalkyl" means and alkyl group in which one or more (including all) the hydrogen radicals are replaced by a halo group, wherein each halo group is independently selected from —F, —Cl, —Br, and —I. The term "halomethyl" means a methyl in which one to three hydrogen radical(s) have been replaced by a halo group. Representative haloalkyl groups include trifluoromethyl, bromomethyl, 1,2-dichloroethyl, 4-iodobutyl, 2-fluoropentyl, and the like.

The term "cycloalkyl" refers to a hydrocarbon 3-8 membered monocyclic or 7-14 membered bicyclic ring system having at least one non-aromatic. Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclooctyl, cyclononyl, and cyclodecyl.

The term "cyclic" or similar term refers to a hydrocarbon 3-8 membered monocyclic or 7-14 membered bicyclic ring system having at least one non-aromatic ring, wherein the non-aromatic ring has some degree of unsaturation. Cyclic groups may be optionally substituted with one or more substituents. In one embodiment, 0, 1, 2, 3, or 4 atoms of each ring of a cyclic group may be substituted by a substituent. Examples of cyclic groups include cyclohexenyl, bicyclo[2.2.1]hept-2-enyl, dihydronaphthalenyl, benzocyclopentyl, cyclopentenyl, cyclopentadienyl, cyclohexenyl, cyclohexadienyl, cycloheptenyl, cycloheptadienyl, cycloheptatrienyl, cyclooctenyl, cyclooctadienyl, cyclooctatrienyl, cyclooctatetraenyl, cyclononenyl, cyclononadienyl, cyclodecenyl, cyclodecadienyl and the like.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

As used herein, the term "aralkyl" means an aryl group that is attached to another group by a ($C_1$-$C_6$)alkylene group. Aralkyl groups may be optionally substituted, either on the aryl portion of the aralkyl group or on the alkylene portion of the aralkyl group, with one or more substituent. Representative aralkyl groups include benzyl, 2-phenyl-ethyl, naphth-3-yl-methyl and the like.

As used herein, the term "alkylene" refers to an alkyl group that has two points of attachment. The term "($C_1$-$C_6$)alkylene" refers to an alkylene group that has from one to six carbon atoms. Non-limiting examples of alkylene groups include methylene (—CH$_2$—), ethylene (—CH$_2$CH$_2$—), n-propylene (—CH$_2$CH$_2$CH$_2$—), isopropylene (—CH$_2$CH(CH$_3$)—), and the like.

The term "arylalkoxy" refers to an alkoxy substituted with aryl.

The term "aryloxy" refers to an —O-aryl radical.

The term "arylthio" refers to an —S-aryl radical.

The term "arylalkythio" refers to an alkylthio substituted with aryl.

The term "heteroaryl" refers to an aromatic 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon (with appropriate hydrogen atoms unless otherwise indicated). Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, 1-oxo-pyridyl, furanyl, benzo[1,3]dioxolyl, benzo[1,4]dioxinyl, thienyl, pyrrolyl, oxazolyl, oxadiazolyl, imidazolyl thiazolyl, isoxazolyl, quinolinyl, pyrazolyl, isothiazolyl, pyridazinyl, pyrimidinyl, pyrazinyl, triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidinyl, pyrazolo[3,4]pyrimidinyl, and benzo(b)thienyl, 3H-thiazolo[2,3-c][1,2,4]thiadiazolyl, imidazo[1,2-d]-1,2,4-thiadiazolyl, imidazo[2,1-b]-1,3,4-thiadiazolyl, 1H,2H-furo[3,4-d]-1,2,3-thiadiazolyl, 1H-pyrazolo[5,1-c]-1,2,4-triazolyl, pyrrolo[3,4-d]-1,2,3-triazolyl, cyclopentatriazolyl, 3H-pyrrolo[3,4-c]isoxazolyl, 1H,3H-pyrrolo[1,2-c]oxazolyl, pyrrolo[2,1b]oxazolyl, and the like.

As used herein, the term "heteroaralkyl" or "heteroarylalkyl" means a heteroaryl group that is attached to another group by a ($C_1$-$C_6$)alkylene. Heteroaralkyl groups may be optionally substituted, either on the heteroaryl portion of the heteroaralkyl group or on the alkylene portion of the heteroaralkyl group, with one or more substituent. Representative heteroaralkyl groups include 2-(pyridin-4-yl)-propyl, 2-(thien-3-yl)-ethyl, imidazol-4-yl-methyl and the like.

The term "heterocycloalkyl" refers to a nonaromatic 5-8 membered monocyclic, 8-12 membered bicyclic, or 11-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si. Heterocycloalkyl groups may be optionally substituted with one or more substituents.

In one embodiment, 0, 1, 2, 3, or 4 atoms of each ring of a heterocycloalkyl group may be substituted by a substituent. Representative heterocycloalkyl groups include piperidinyl, piperazinyl, 2-oxopiperazinyl, 2-oxopiperidinyl, 2-oxopyrrolidinyl, 4-piperidonyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane, tetrahydrofuranyl, tetrahydrothienyl, thiirene.

The term "heterocycloalkyl" also refers to a nonaromatic 5-8 membered monocyclic, 8-12 membered bicyclic, or 11-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein the nonaromatic ring system has some degree of unsaturation. Heterocyclyl groups may be optionally substituted with one or more substituents. In one embodiment, 0, 1, 2, 3, or 4 atoms of each ring of a heterocyclyl group may be substituted by a substituent. Examples of these groups include thiirenyl, thiadiazirinyl, dioxazolyl, 1,3-oxathiolyl, 1,3-dioxolyl, 1,3-dithiolyl, oxathiazinyl, dioxazinyl, dithiazinyl, oxadiazinyl, thiadiazinyl, oxazinyl, thiazinyl, 1,4-oxathiin, 1,4-dioxin, 1,4-dithiin, 1H-pyranyl, oxathiepinyl, 5H-1,4-dioxepinyl, 5H-1,4-dithiepinyl, 6H-isoxazolo[2,3-d] 1,2,4-oxadiazolyl, 7aH-oxazolo[3,2-d]1,2,4-oxadiazolyl, and the like.

The term "alkylamino" refers to an amino substituent which is further substituted with one or two alkyl groups. The term "aminoalkyl" refers to an alkyl substituent which is further substituted with one or more amino groups. The term "mercaptoalkyl" refers to an alkyl substituent which is further substituted with one or more mercapto groups. The term "hydroxyalkyl" or "hydroxylalkyl" refers to an alkyl substituent which is further substituted with one or more hydroxyl groups. The term "sulfonylalkyl" refers to an alkyl substituent which is further substituted with one or more sulfonyl groups. The term "sulfonylaryl" refers to an aryl substituent which is further substituted with one or more sulfonyl groups. The term alkylcarbonyl refers to an —C(O)-alkyl. The term "mercaptoalkoxy" refers to an alkoxy substituent which is further substituted with one or more mercapto groups.

The term "alkylcarbonylalkyl" refers to an alkyl substituent which is further substituted with —C(O)-alkyl. The alkyl or aryl portion of alkylamino, aminoalkyl, mercaptoalkyl, hydroxyalkyl, mercaptoalkoxy, sulfonylalkyl, sulfonylaryl, alkylcarbonyl, and alkylcarbonylalkyl may be optionally substituted with one or more substituents.

As used herein the term "substituent" or "substituted" means that a hydrogen radical on a compound or group (such as, for example, alkyl, alkenyl, alkynyl, alkylene, aryl, aralkyl, heteroaryl, heteroaralkyl, cycloalkyl, or heterocycloalkyl group) is replaced with any desired group that do not substantially adversely affect the stability of the compound. In one embodiment, desired substituents are those which do not adversely affect the activity of a compound. The term "substituted" refers to one or more substituents (which may be the same or different), each replacing a hydrogen atom. Examples of substituents include, but are not limited to, halogen (F, Cl, Br, or I), hydroxyl, amino, alkylamino, arylamino, dialkylamino, diarylamino, cyano, nitro, mercapto, oxo (i.e., carbonyl), thio, imino, formyl, carbamido, carbamyl, carboxyl, thioureido, thiocyanato, sulfoamido, sulfonylalkyl, sulfonylaryl, alkyl, alkenyl, alkoxy, mercaptoalkoxy, aryl, heteroaryl, cycloalkyl, heterocycloalkyl, wherein alkyl, alkenyl, alkyloxy, aryl, heteroaryl, cycloalkyl, and heterocycloalkyl are optionally substituted with alkyl, aryl, heteroaryl, halogen, hydroxyl, amino, mercapto, cyano, nitro, oxo (=O), thioxo (=S), or imino (=NR$^c$).

In other embodiments, substituents on any group (such as, for example, alkyl, alkenyl, alkynyl, aryl, aralkyl, heteroaryl, heteroaralkyl, cycloalkyl, heterocycloalkyl) can be at any atom of that group, wherein any group that can be substituted (such as, for example, alkyl, alkenyl, alkynyl, aryl, aralkyl, heteroaryl, heteroaralkyl, cycloalkyl, heterocycloalkyl) can be optionally substituted with one or more substituents (which may be the same or different), each replacing a hydrogen atom. Examples of suitable substituents include, but not limited to alkyl, alkenyl, alkynyl, cycloalkyl, heterocloalkyl, aralkyl, heteroaralkyl, aryl, heteroaryl, halogen, haloalkyl, cyano, nitro, alkoxy, aryloxy, alkylthio, hydroxyl, hydroxylalkyl, oxo (i.e., carbonyl), carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, thio, mercapto, mercaptoalkyl, arylsulfonyl, amino, aminoalkyl, dialkylamino, alkylcarbonylamino, alkylaminocarbonyl, alkoxycarbonylamino; alkylamino, arylthio, arylamino, diarylamino, alkylcarbonyl, or arylamino-substituted aryl; arylalkylamino, aralkylaminocarbonyl, amido, alkylaminosulfonyl, arylaminosulfonyl, dialkylaminosulfonyl, alkylsulfonylamino, arylsulfonylamino, imino, carbamido, carbamyl, thioureido, thiocyanato, sulfoamido, sulfonylalkyl, sulfonylaryl, or mercaptoalkoxy.

Additional suitable substituents an alkyl, alkenyl, alkynyl, aryl, aralkyl, heteroaryl, heteroaralkyl, cycloalkyl, and heterocycloalkyl include, without limitation halogen, CN, NO$_2$, OR$^{15}$, SR$^{15}$, S(O)$_2$OR$^{15}$, NR$^{15}$R$^{16}$, C$_1$-C$_2$ perfluoroalkyl, C$_1$-C$_2$ perfluoroalkoxy, 1,2-methylenedioxy, (=O), (=S), (=NR$^{15}$), C(O)OR$^{15}$, C(O)NR$^{15}$R$^{16}$, OC(O)NR$^{15}$R$^{16}$, NR$^{15}$C(O)R$^{15}$R$^{16}$, C(NR$^{16}$)NR$^{15}$R$^{16}$, NR$^{15}$C(NR$^{16}$) NR$^{15}$R$^{16}$, S(O)$_2$NR$^{15}$R$^{16}$, R$^{17}$, C(O)H, C(O)R$^{17}$, NR$^{15}$C(O) R$^{17}$, Si(R$^{15}$)$_3$, OSi(R$^{15}$)$_3$, Si(OH)$_2$R$^{15}$, B(OH)$_2$, P(O) (OR$^{15}$)$_2$, S(O)R$^{17}$, or S(O)$_2$R$^{17}$. Each R$^{15}$ is independently hydrogen, C$_1$-C$_6$ alkyl optionally substituted with cycloalkyl, aryl, heterocycloalkyl, or heteroaryl. Each le is independently hydrogen, C$_3$-C$_6$ cycloalkyl, aryl, heterocycloalkyl, heteroaryl, C$_1$-C$_4$ alkyl or C$_1$-C$_4$ alkyl substituted with C$_3$-C$_6$ cycloalkyl, aryl, heterocycloalkyl or heteroaryl. Each R$^{17}$ is independently C$_3$-C$_6$ cycloalkyl, aryl, heterocycloalkyl, heteroaryl, C$_1$-C$_4$ alkyl or C$_1$-C$_4$ alkyl substituted with C$_3$-C$_6$ cycloalkyl, aryl, heterocycloalkyl or heteroaryl. Each C$_3$-C$_6$ cycloalkyl, aryl, heterocycloalkyl, heteroaryl and C$_1$-C$_4$ alkyl in each R$^{15}$, R$^{16}$ and R$^{17}$ can optionally be substituted with halogen, CN, C$_1$-C$_4$ alkyl, OH, C$_1$-C$_4$ alkoxy, COOH, C(O) OC$_1$-C$_4$ alkyl, NH$_2$, C$_1$-C$_4$ alkylamino, or C$_1$-C$_4$ dialkylamino.

As used herein, the term "lower" refers to a group having up to six atoms. For example, a "lower alkyl" refers to an alkyl radical having from 1 to 6 carbon atoms, and a "lower alkenyl" or "lower alkynyl" refers to an alkenyl or alkynyl radical having from 2 to 6 carbon atoms, respectively.

The recitation of a listing of chemical groups in any definition of a variable herein includes definitions of that variable as any single group or combination of listed groups.

Combinations of substituents and variables envisioned by this invention are preferably those that result in the formation of stable compounds. The term "stable", as used herein, refers to compounds which possess stability sufficient to allow manufacture and which maintains the integrity of the compound for a sufficient period of time to be useful for the purposes detailed herein (e.g., formulation into therapeutic products, intermediates for use in production of therapeutic compounds, isolatable or storable intermediate compounds, treating diseases, disorders or symptoms thereof). The compounds produced by the methods herein can be incorporated into compositions, including solutions, capsules, crèmes, or ointments for administration to a subject (e.g., human, animal). Such compositions (e.g., pharmaceuticals) are useful for providing to the subject desirable health or other physiological benefits that are associated with such compounds.

The compounds of this invention include the compounds themselves, as well as their salts, solvates, hydrates, polymorphs, or prodrugs, if applicable.

The term "pharmaceutically acceptable salt" also refers to a salt prepared from a compound of any one of the formulae disclosed herein having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl, N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like. The term "pharmaceutically acceptable salt" also refers to a salt prepared from a compound of any one of the formulae disclosed herein having a basic functional group, such as an amino functional group, and a pharmaceutically acceptable inorganic or organic acid. Suitable acids include hydrogen sulfate, citric acid, acetic acid, oxalic acid, hydrochloric acid (HCl), hydrogen bromide (HBr), hydrogen iodide (HI), nitric acid, phosphoric acid, lactic acid, salicylic acid, tartaric acid, ascorbic acid, succinic acid, maleic acid, besylic acid, fumaric acid, gluconic acid, glucaronic acid, formic acid, benzoic acid, glutamic acid, methanesulfonic acid, ethanesulfonic acid, benzenesulfonic acid, and p-toluenesulfonic acid.

As used herein, the terms "subject" and "patient" are used interchangeably. As used herein, the terms "subject" and "subjects" refer to an animal, preferably a mammal including a non-primate (e.g., a cow, pig, horse, cat, dog, rat, and mouse) and a primate (e.g., a monkey, ape, monkey, or human), and more particularly a human.

Compounds of the Invention

As discussed above, compounds of the following Formula (I), or pharmaceutically acceptable salt, solvate or hydrate thereof are provided, as well as the use of such compounds in the treatment of the diseases and disorders disclosed herein:

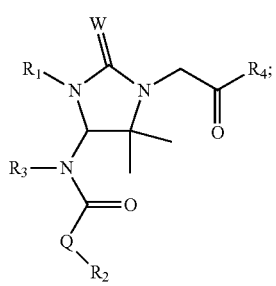

Formula I wherein
W is O, S, or $NR_A$;
Q is O, S, or $NR_A$;
$R_1$ is selected from hydrogen, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted haloalkyl, optionally substituted alkoxy, optionally substituted cycloalkoxy, optionally substituted (cycloalkyl)alkoxy, or optionally substituted heterocycloalkyl;
$R_2$ is selected from hydrogen, optionally substituted alkyl, optionally substituted cycloalkyl, optionally substituted aryl, optionally substituted heteroaryl, optionally substituted haloalkyl, optionally substituted alkoxy, optionally substituted cycloalkoxy, optionally substituted (cycloalkyl)alkoxy, or optionally substituted heterocycloalkyl;
$R_3$ is selected from hydrogen or hydroxyl;
$R_4$ is X—Y—Z;
wherein X is O, S, or $NR_B$;
Y is alkyl, alkenyl, or alkynyl, each of which may be substituted with a heteroatom; wherein at least one carbon of each alkyl, alkenyl, or alkynyl may be substituted by a heteroatom;
Z is an optionally substituted aryl or an optionally substituted heteroaryl;
each $R_A$ is independently selected from hydrogen, optionally substituted alkyl, optionally substituted aryl, or optionally substituted heteroaryl; and
$R_B$ is selected from hydrogen or optionally substituted alkyl.

In one embodiment, $R_1$ is selected from optionally substituted cycloalkyl, optionally substituted cycloalkenyl, optionally substituted aryl, or optionally substituted heteroaryl. In another embodiment, $R_2$ is selected from optionally substituted aryl or optionally substituted heteroaryl. In other embodiments, Q is $NR_A$; and $R_A$ is hydrogen. In still other embodiments, $R_3$ is hydroxyl.

In another aspect, compounds of the following Formula (II), or pharmaceutically acceptable salt, solvate or hydrate thereof are provided as well as use of such compounds in the treatment of the diseases and disorders disclosed herein:

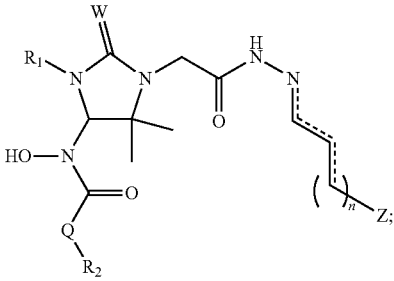

Formula II wherein
Q is O, S, or $NR_A$;
$R_1$ is selected from hydrogen, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted haloalkyl, optionally substituted alkoxy, optionally substituted cycloalkoxy, optionally substituted (cycloalkyl)alkoxy, or optionally substituted heterocycloalkyl;
$R_2$ is selected from hydrogen, optionally substituted alkyl, optionally substituted cycloalkyl, optionally substituted aryl, optionally substituted heteroaryl, optionally substituted haloalkyl, optionally substituted alkoxy, optionally substituted cycloalkoxy, optionally substituted (cycloalkyl)alkoxy, or optionally substituted heterocycloalkyl;
Z is an optionally substituted aryl or an optionally substituted heteroaryl; and
n is 0-3.

Specifically preferred compounds of the invention particularly for use in the therapeutic methods disclosed herein are the following (and salts and solvates thereof):

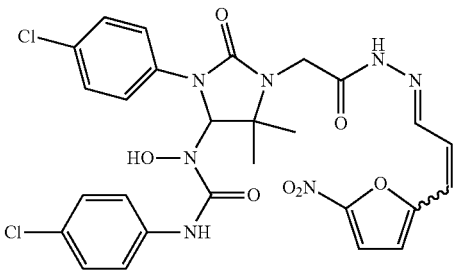 [SMILES: CC1(C)C(N(O)C(=O)Nc2ccc(Cl)cc2)N(c2ccc(Cl)cc2)C(=O)N1CC(=O)N/N=C/C=Cc1ccc([N+](=O)[O-])o1]

Eeyarestatin I; 1-(4-chloro-phenyl)-3-[3-(4-chloro-phenyl)-5,5-dimethyl-1-[3-(5-nitro-furan-2-yl)-allyldiene-hydrazinocarbonylmethyl]-2-oxo-imidazolidin-4-yl]-1-hydroxyl-urea; and

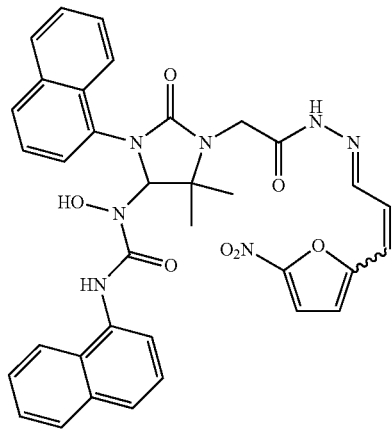 [SMILES: CC1(C)C(N(O)C(=O)Nc2cccc3ccccc23)N(c2cccc3ccccc23)C(=O)N1CC(=O)N/N=C/C=Cc1ccc([N+](=O)[O-])o1]

Eeyarestatin II; 1-[5,5-dimethyl-3-naphthalen-1-yl-1 [3-(5-nitro-furan-2-yl)-allyldiene-hydrazinocarbonylmethyl]-2-oxo-imidazolidin-4-yl]-3-naphthalen-1-yl-1-hydroxyl-urea.

In another aspect, compounds of the following Formula (III), or pharmaceutically acceptable salt, solvate or hydrate thereof are provided as well as use of such compounds in the treatment of the diseases and disorders disclosed herein:

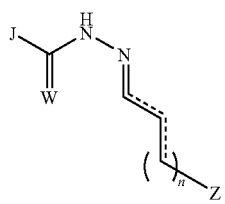

(III)

Wherein

Figure 19A:
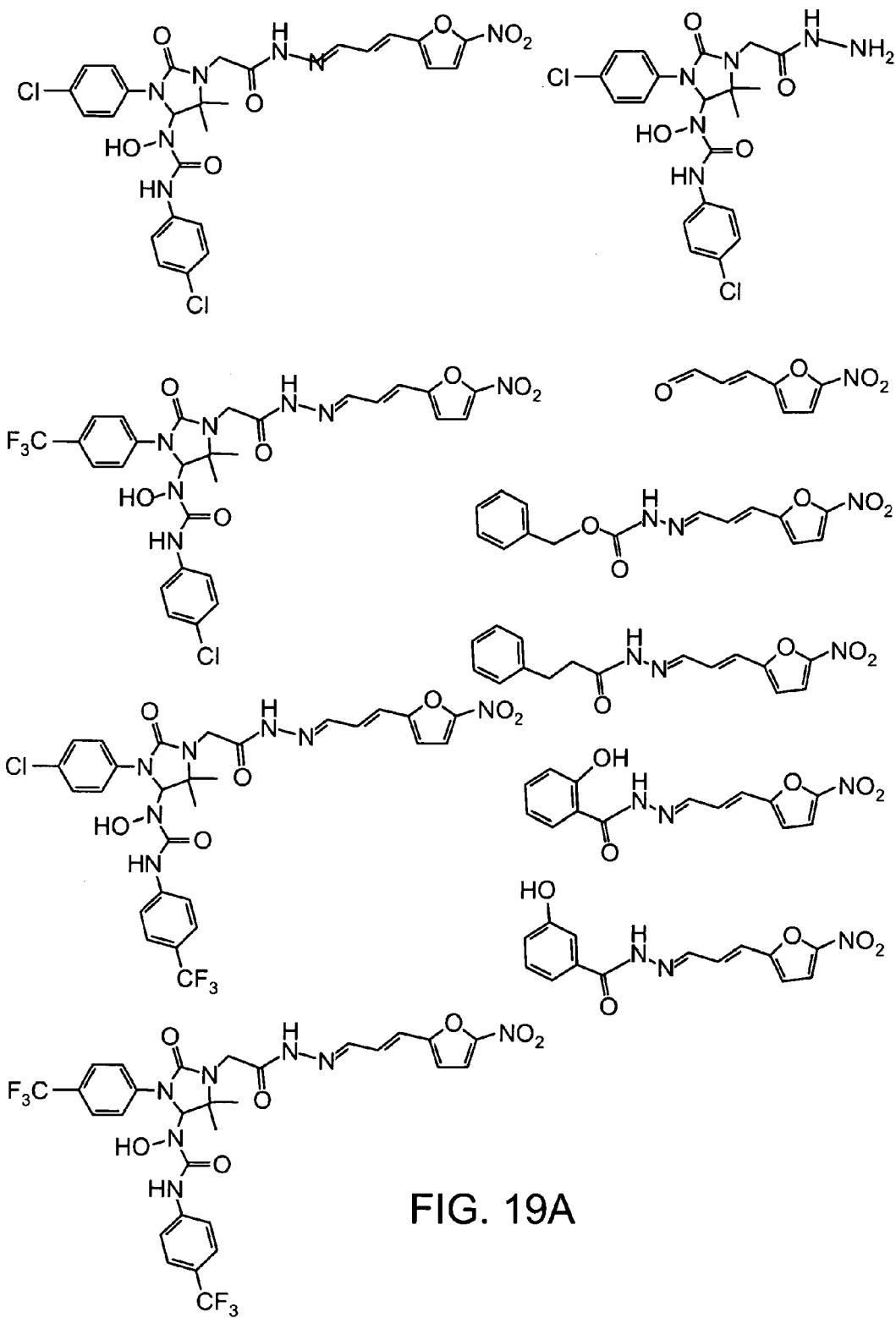
FIG. 19 shows (A) cytotoxicity of EerI and its structurally related chemicals. JEKO-1 cells were treated with the indicated chemicals at concentrations ranging from 0.625 µM to 100 µM for 48 hours. Cell viability was measured by a MTT assay. The estimated IC50 indicates the concentration of compound required to achieve 50% killing in JEKO-1 cells. (B) the Cell killing data for the depicted structures.
Figure 19B:
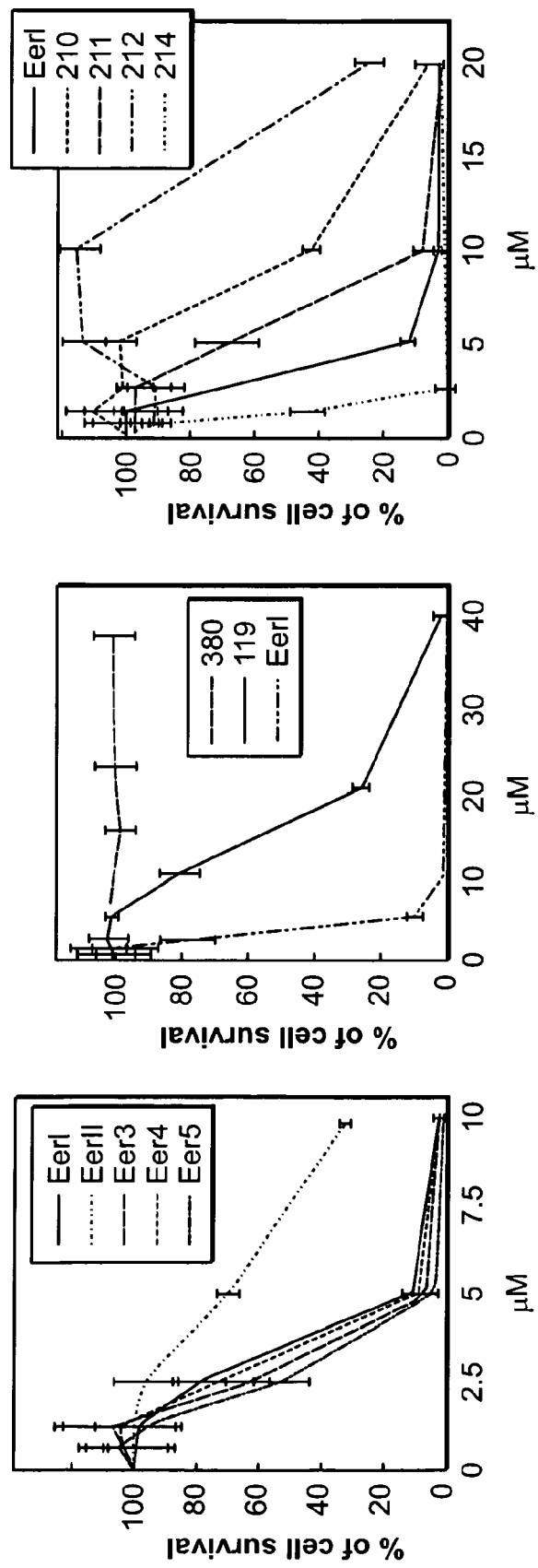

W is O, S, or $NR_A$;

J is optionally substituted aryl, optionally substituted arylalkyl, optionally substituted alkyloxy, optionally substituted aryloxy, optionally substituted arylthio, optionally substituted alkylthio, optionally substituted arylamino, optionally substituted alkylamino, optionally substituted arylalkoxy, optionally substituted arylalkylthio, optionally substituted arylalkylamino, optionally substituted heteroaryl;

Z is an optionally substituted aryl or an optionally substituted heteroaryl; and n is 0-3;

Specifically preferred compounds of the invention of formula III particularly for use in the therapeutic methods disclosed herein are the following (and salts and solvates thereof) include those shown in FIG. 19.

The compounds herein are commercially available or can be synthesized. As can be appreciated by the skilled artisan, methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, 2nd. Ed., Wiley-VCH Publishers (1999); T. W. Greene and P. G. M. Wuts, *Protective Groups in Organic Synthesis*, 3rd. Ed., John Wiley and Sons (1999); L. Fieser and M. Fieser, *Fieser and Fieser's Reagents for Organic Synthesis*, John Wiley and Sons (1999); and L. Paquette, ed., *Encyclopedia of Reagents for Organic Synthesis*, John Wiley and Sons (1995), and subsequent editions thereof.

The compounds herein may contain one or more asymmetric centers and thus occur as racemates and racemic mixtures, single enantiomers, individual diastereomers and diastereomeric mixtures. All such isomeric forms of these compounds are expressly included in the present invention.

The compounds herein may also contain linkages (e.g., carbon-carbon bonds) wherein bond rotation is restricted about that particular linkage, e.g. restriction resulting from the presence of a ring or double bond. Accordingly, all cis/trans and E/Z isomers are expressly included in the present invention. The compounds herein may also be represented in multiple tautomeric forms, in such instances, the invention expressly includes all tautomeric forms of the compounds described herein, even though only a single tautomeric form may be represented (e.g., alkylation of a ring system may result in alkylation at multiple sites, the invention expressly includes all such reaction products).

All such isomeric forms of such compounds herein are expressly included in the present invention. All crystal forms and polymorphs of the compounds described herein are expressly included in the present invention.

Methods of Synthesis

In a specific aspect, the invention provides a process for preparing a compound of formula (II), in which Q is NH and $R_1 = R_2$, comprising the steps of a.) Reacting a compound of the formula (VI):

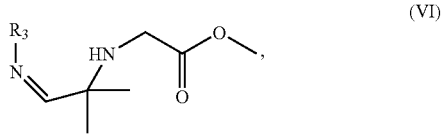

(VI)

with a compound of the formula (VII):

(VII)

and a compound of the formula (VIIa):

(VIIa)

wherein each occurrence of W may be the same or different and wherein $R_1$ and $R_2$ may be the same or different, to produce a compound of the formula (VIII):

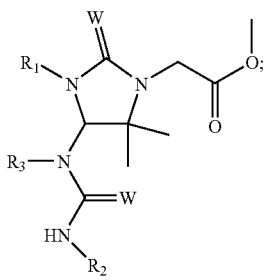
(VIII)

b) hydrazinolyzing the compound of formula (VIII) of step a); and
c) reacting the product of step b) with a compound of the formula (V):

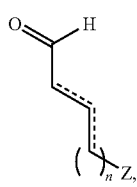
(V)

to produce a compound of formula (II).

In another aspect, the invention provides a process for preparing a compound of formula (III)

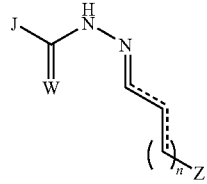
(III)

Wherein
W is O, S, or $NR_A$;
J is optionally substituted aryl, optionally substituted arylalkyl, optionally substituted alkyloxy, optionally substituted aryloxy, optionally substituted arylthio, optionally substituted alkylthio, optionally substituted arylamino, optionally substituted alkylamino, optionally substituted arylalkoxy, optionally substituted arylalkylthio, optionally substituted arylalkylamino, optionally substituted heteroaryl;

Z is an optionally substituted aryl or an optionally substituted heteroaryl; and n is 0-3;

comprising the step of: reacting a compound of the formula:

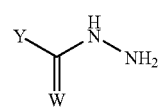
(IV)

wherein
W and Y are as defined above
with a compound of the formula:

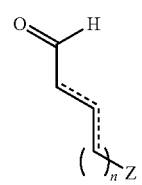
(V)

wherein
Z and n are as defined above
to produce a compound of formula (III).

Furthermore, Eeyarestatin I may be synthesized using the following general scheme:

Scheme 1

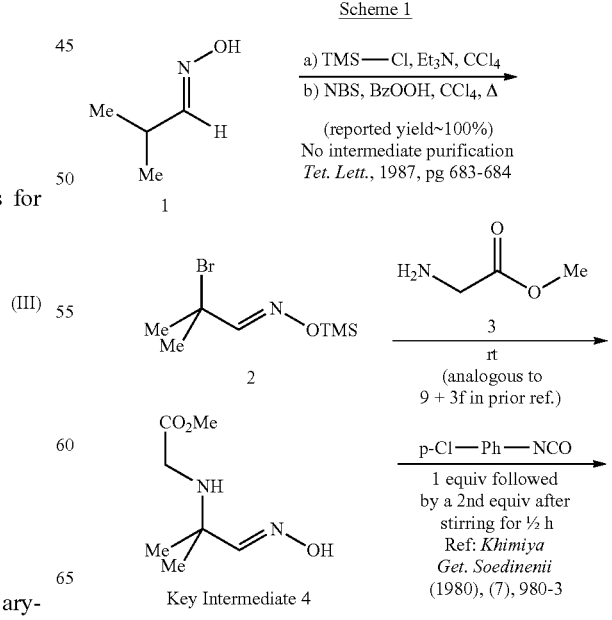

Key Intermediate 4

-continued

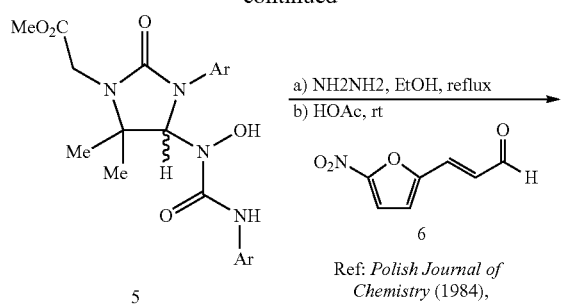

Ref: *Polish Journal of Chemistry* (1984), 58(4-5-6), 585-91.

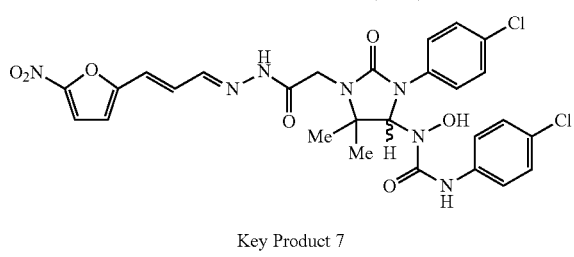

Key Product 7

Similarly, differentially substituted analogs of Eeyarestatin I may be synthesized using the following general scheme:

Scheme 2.

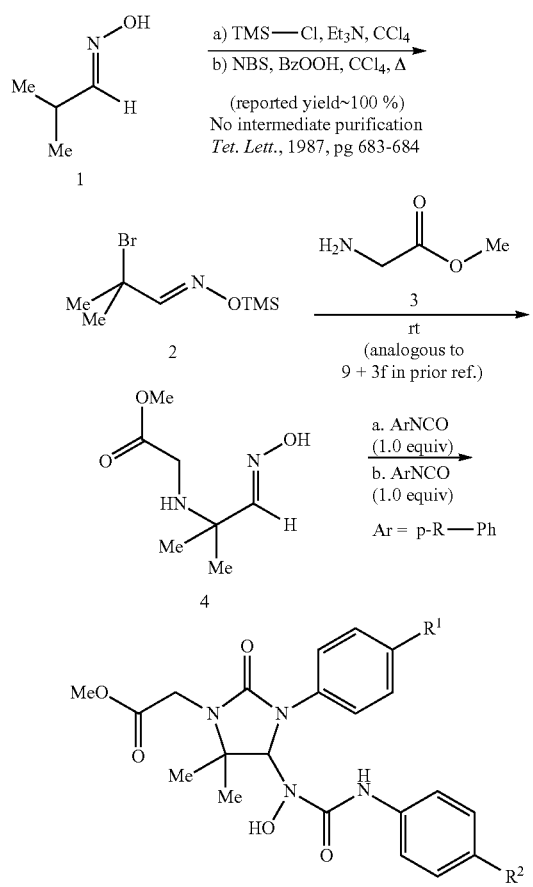

a $R^1, R^2 = Cl$; 99%
b $R^1, R^2 = CF_3$; 99%

-continued

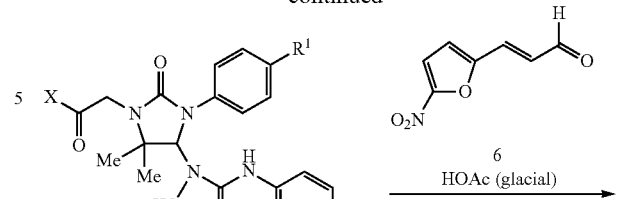

$X = OMe$ ⎤
$X = NHNH_2$ ⎦ $\xleftarrow{NH_2NH_2}{EtOH, reflux}$ a, 61%; b, 62%
c, 88%, d, in progress

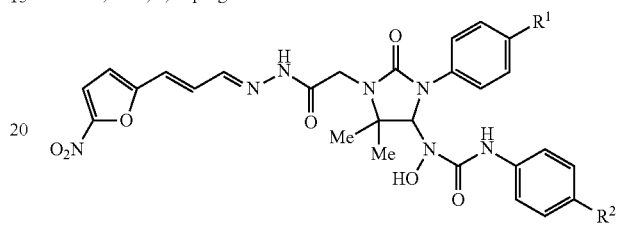

7a, 82%; 7b, 86%
7c, 86%, 7d, 65%

In an alternative synthesis, the transition from (4) to (5) can be accomplished using the synthetic scheme depicted below:

Scheme 3

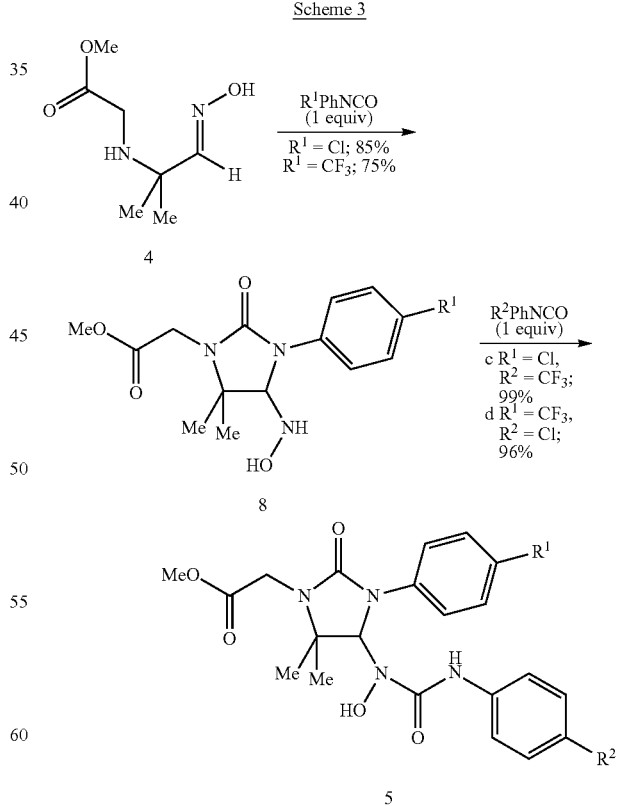

Methods of Treatment

In one aspect, the invention provides a method of treating a deubiquitination-related disorder in a subject, comprising administering to said subject in need thereof, an effective amount of an imidazolidinone compound.

In one embodiment, the imidazolidinone compound is a deubiquitination inhibitor.

Without being bound by theory, it is believed that the imidazolidinone compound binds p97 either directly or indirectly in cells. As such, in one embodiment, the imidazolidinone compound is an compound which binds to or otherwise associates with p97. In certain embodiments, the imidazolidinone compound binds to or otherwise associates with p97 without inhibiting deubiquitination.

In another embodiment the compound is of Formula (I), or pharmaceutically acceptable salt, solvate or hydrate thereof:

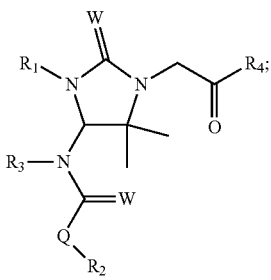

Formula I wherein
  each occurrence of W is independently O, S, or $NR_A$;
  Q is O, S, or $NR_A$;
  $R_1$ is selected from hydrogen, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted haloalkyl, optionally substituted alkoxy, optionally substituted cycloalkoxy, optionally substituted (cycloalkyl)alkoxy, or optionally substituted heterocycloalkyl;
  $R_2$ is selected from hydrogen, optionally substituted alkyl, optionally substituted cycloalkyl, optionally substituted aryl, optionally substituted heteroaryl, optionally substituted haloalkyl, optionally substituted alkoxy, optionally substituted cycloalkoxy, optionally substituted (cycloalkyl)alkoxy, or optionally substituted heterocycloalkyl;
  $R_3$ is selected from hydrogen or hydroxyl;
  $R_4$ is X—Y—Z;
  wherein X is O, S, or $NR_B$;
  Y is alkyl, alkenyl, or alkynyl, each of which may be substituted with a heteroatom; wherein at least one carbon of each alkyl, alkenyl, or alkynyl may be substituted by a heteroatom;
  Z is an optionally substituted aryl or an optionally substituted heteroaryl;
  each $R_A$ is independently selected from hydrogen, optionally substituted alkyl, optionally substituted aryl, or optionally substituted heteroaryl; and
  $R_B$ is selected from hydrogen or optionally substituted alkyl.

In a further embodiment, $R_1$ is selected from optionally substituted cycloalkyl, optionally substituted cycloalkenyl, optionally substituted aryl, or optionally substituted heteroaryl. In another embodiment, $R_2$ is selected from optionally substituted aryl or optionally substituted heteroaryl. In other embodiments, Q is $NR_A$; and $R_A$ is hydrogen. In still other embodiments, $R_3$ is hydroxyl.

In another embodiment, the compound is of Formula (II), or pharmaceutically acceptable salt, solvate or hydrate thereof:

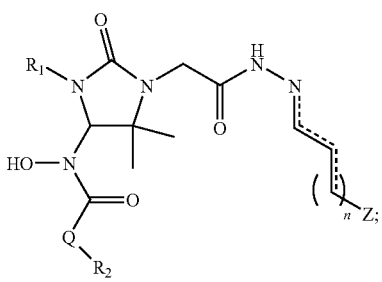

Formula II wherein
  Q is O, S, or $NR_A$;
  $R_1$ is selected from hydrogen, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted haloalkyl, optionally substituted alkoxy, optionally substituted cycloalkoxy, optionally substituted (cycloalkyl)alkoxy, or optionally substituted heterocycloalkyl;
  $R_2$ is selected from hydrogen, optionally substituted alkyl, optionally substituted cycloalkyl, optionally substituted aryl, optionally substituted heteroaryl, optionally substituted haloalkyl, optionally substituted alkoxy, optionally substituted cycloalkoxy, optionally substituted (cycloalkyl)alkoxy, or optionally substituted heterocycloalkyl;
  Z is an optionally substituted aryl or an optionally substituted heteroaryl; and
  n is 0-3.

In another embodiment, the compound is of formula (III)

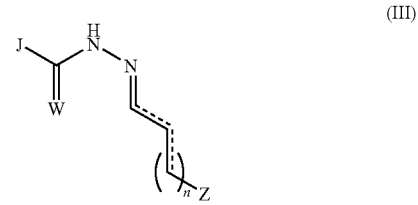

(III)

Wherein
  W is O, S, or $NR_A$;
  J is optionally substituted aryl, optionally substituted arylalkyl, optionally substituted alkyloxy, optionally substituted aryloxy, optionally substituted arylthio, optionally substituted alkylthio, optionally substituted arylamino, optionally substituted alkylamino, optionally substituted arylalkoxy, optionally substituted arylalkylthio, optionally substituted arylalkylamino, optionally substituted heteroaryl;
  Z is an optionally substituted aryl or an optionally substituted heteroaryl; and
  n is 0-3.

In another embodiment, the subject is identified as being in need of inhibition of deubiquitination, and the compound of formula I is administered to the identified subject.

In another embodiment, the invention provides a method further comprising the step of identifying a subject in need of such treatment for a deubiquitination disorder and administering the compound to the identified subject.

In certain embodiments, the subject is suffering from a cell proliferative disorder or disease. In one embodiment, the disorder is cancer, tumor, neoplasm, neovascularization, vascularization, cardiovascular disease, intravasation, extravasation, metastasis, arthritis, infection, Alzheimer's Disease, blood clot, atherosclerosis, melanoma, skin disorder, rheumatoid arthritis, diabetic retinopathy, macular edema, or macular degeneration, inflammatory and arthritic disease, autoimmune disease or osteosarcoma. Certain therapeutic methods of the invention include treating malignancies, including solid tumors and disseminated cancers. Exemplary tumors that may be treated in accordance with the invention include e.g. cancers of the lung, prostate, breast, liver, colon, breast, kidney, pancreas, brain, skin including malignant melanoma and Kaposi's sarcoma, testes or ovaries, or leukemias or lymphoma including Hodgkin's disease. Exemplary autoimmune diseases include, but are not limited to lupus.

In a further embodiment, the subject is suffering from a solid tumor or disseminated cancer. In another further embodiment, the cancer is leukemia, multiple myeloma or lymphoma.

In certain embodiments, the subject being treated with the imidazolidinone compound of the invention is resistant to treatment with a proteasome inhibitor. In one embodiment, the subject being treated with the imidazolidinone compound of the invention is resistant to treatment with bortezomib (BZM).

In certain aspects, the invention provides a method of treating a subject suffering from a deubiquitination related disorder, wherein the subject is treated with a composition comprising a compound of formula I and a proteasome inhibitor. In one embodiment, the proteasome inhibitor is bortezomib. In another embodiment, the disorder is resistant to treatment with a proteasome inhibitor, such as bortezomib. The combination of the compound of the invention and the proteasome inhibitor provides the unexpected result of a synergistic effect in treating certain disorders as delineated in the invention.

In other embodiments, the method further comprises administering an additional therapeutic agent. In a further embodiment, the additional therapeutic agent is an anticancer compound.

One or more compounds of the invention including those of the formulae herein may be administered in coordination with a regime of one or more other chemotherapeutic agents, particularly a compound that functions against cancer cells other than by p97 associated deubiquitination inhibition, such as an antineoplastic drug, e.g., an alkylating agent (e.g., mechloroethamine, chlorambucil, cyclophosamide, melphalan, or ifosfamide), an antimetabolite such as a folate antagonist (e.g., methotrexate), a purine antagonist (e.g. 6-mercaptopurine) or a pyrimidine antagonist (e.g., 5-fluorouracil). Other, non-limiting examples of chemotherapeutic agents that might be used in coordination with one or more compounds of the invention include taxanes and topoisomerase inhibitors. In addition, other non-limiting examples of active therapeutics include biological agents, such as monoclonal antibodies or IgG chimeric molecules, that achieve their therapeutic effect by specifically binding to a receptor or ligand in a signal transduction pathway associated with cancer (e.g. therapeutic antibodies directed against CD20 (e.g. rituximab) or against VEGF (e.g. bevacizumab)).

In one embodiment, the invention provides a method of treating a deubiquitination-related disorder in a subject wherein the subject is a mammal, preferably a primate or human.

In other aspects, the invention provides a method of treating cancer in a subject identified as in need of such treatment, the method comprising administering to said subject an effective amount of a compound of formula I:

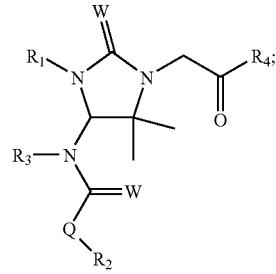

Formula I wherein
  each occurrence of W is independently O, S, or $NR_A$;
  Q is O, S, or $NR_A$;
  $R_1$ is selected from hydrogen, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted haloalkyl, optionally substituted alkoxy, optionally substituted cycloalkoxy, optionally substituted (cycloalkyl)alkoxy, or optionally substituted heterocycloalkyl;
  $R_2$ is selected from hydrogen, optionally substituted alkyl, optionally substituted cycloalkyl, optionally substituted aryl, optionally substituted heteroaryl, optionally substituted haloalkyl, optionally substituted alkoxy, optionally substituted cycloalkoxy, optionally substituted (cycloalkyl)alkoxy, or optionally substituted heterocycloalkyl;
  $R_3$ is selected from hydrogen or hydroxyl;
  $R_4$ is X—Y—Z;
  wherein X is O, S, or $NR_B$;
  Y is alkyl, alkenyl, or alkynyl, each of which may be substituted with a heteroatom; wherein at least one carbon of each alkyl, alkenyl, or alkynyl may be substituted by a heteroatom;
  Z is an optionally substituted aryl or an optionally substituted heteroaryl;
  each $R_A$ is independently selected from hydrogen, optionally substituted alkyl, optionally substituted aryl, or optionally substituted heteroaryl; and
  $R_B$ is selected from hydrogen or optionally substituted alkyl.

In one embodiment, the compound is a deubiquitination inhibitor.

In another embodiment, the subject is resistant to treatment with a proteasome inhibitor, such as bortezomib.

In another embodiment, the compound of formula I used in the treatment of cancer is:

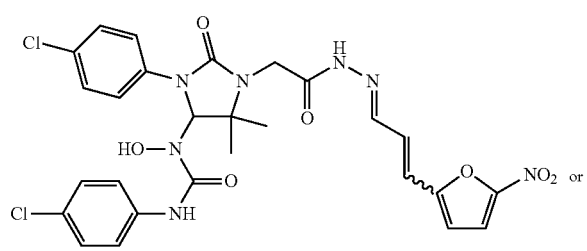

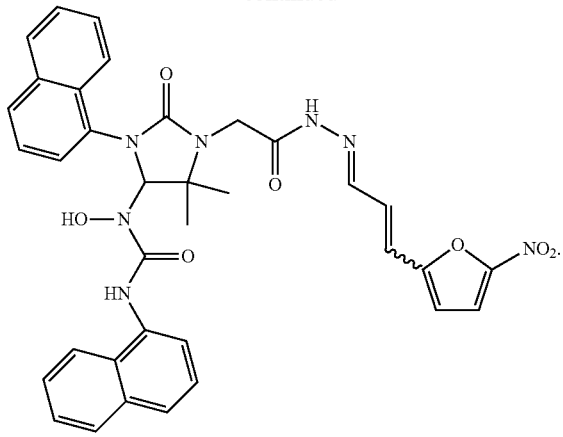

In another embodiment, the invention provides a method further comprising an additional therapeutic agent. In a further embodiment, the additional therapeutic agent is an anticancer compound.

In certain embodiments, the step of administering the compound comprises administering the compound orally, topically, parentally, intravenously or intramuscularly.

In yet another embodiment, the invention provides a method comprising the step of administering an effective amount of a composition comprising a compound of formula I and a pharmaceutically suitable excipient.

In another aspect, the invention provides a method of treating a subject suffering from or susceptible to viral infection comprising administering to the subject an effective amount an imidazolidinone compound.

In one embodiment, the subject is infected with a retrovirus. In a further embodiment, the subject is infected with HIV.

In another embodiment, the subject is identified as having a virus infection and the compound is administered to the identified subject.

In still another embodiment, the compound of the following Formula (I), or pharmaceutically acceptable salt, solvate or hydrate thereof is administered to the subject:

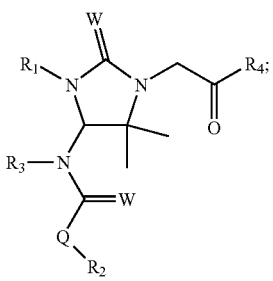

Formula I wherein each occurrence of W is independently O, S, or $NR_A$;

Q is O, S, or $NR_A$;

$R_1$ is selected from hydrogen, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted haloalkyl, optionally substituted alkoxy, optionally substituted cycloalkoxy, optionally substituted (cycloalkyl)alkoxy, or optionally substituted heterocycloalkyl;

$R_2$ is selected from hydrogen, optionally substituted alkyl, optionally substituted cycloalkyl, optionally substituted aryl, optionally substituted heteroaryl, optionally substituted haloalkyl, optionally substituted alkoxy, optionally substituted cycloalkoxy, optionally substituted (cycloalkyl)alkoxy, or optionally substituted heterocycloalkyl;

$R_3$ is selected from hydrogen or hydroxyl;

$R_4$ is X—Y—Z;

wherein X is O, S, or $NR_B$;

Y is alkyl, alkenyl, or alkynyl, each of which may be substituted with a heteroatom; wherein at least one carbon of each alkyl, alkenyl, or alkynyl may be substituted by a heteroatom;

Z is an optionally substituted aryl or an optionally substituted heteroaryl;

each $R_A$ is independently selected from hydrogen, optionally substituted alkyl, optionally substituted aryl, or optionally substituted heteroaryl; and $R_B$ is selected from hydrogen or optionally substituted alkyl.

In another embodiment, a compound of the following Formula (II), or pharmaceutically acceptable salt, solvate or hydrate thereof, is administered to the subject:

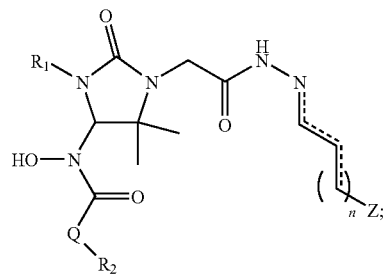

Formula II wherein

Q is O, S, or $NR_A$;

$R_1$ is selected from hydrogen, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted haloalkyl, optionally substituted alkoxy, optionally substituted cycloalkoxy, optionally substituted (cycloalkyl)alkoxy, or optionally substituted heterocycloalkyl;

$R_2$ is selected from hydrogen, optionally substituted alkyl, optionally substituted cycloalkyl, optionally substituted aryl, optionally substituted heteroaryl, optionally substituted haloalkyl, optionally substituted alkoxy, optionally substituted cycloalkoxy, optionally substituted (cycloalkyl)alkoxy, or optionally substituted heterocycloalkyl;

Z is an optionally substituted aryl or an optionally substituted heteroaryl; and n is 0-3.

In another embodiment, the administered compound is of formula (III)

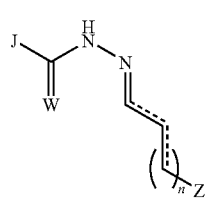

Wherein
W is O, S, or NR$_A$;
J is optionally substituted aryl, optionally substituted arylalkyl, optionally substituted alkyloxy, optionally substituted aryloxy, optionally substituted arylthio, optionally substituted alkylthio, optionally substituted arylamino, optionally substituted alkylamino, optionally substituted arylalkoxy, optionally substituted arylalkylthio, optionally substituted arylalkylamino, optionally substituted heteroaryl;
Z is an optionally substituted aryl or an optionally substituted heteroaryl; and
n is 0-3.

In other embodiments, the invention provides a method further comprising administering an additional therapeutic agent.

For an antiviral therapy, one or more compounds of the invention including those of the formulae herein may be administered in coordination with a regime of one or more other antiviral agents such as reverse transcriptase inhibitors such as dideoxynucleosides, e.g. zidovudine (AZT), 2',3'-dideoxyinosine (ddI) and 2',3'-dideoxycytidine (ddC), lamivudine (3TC), stavudine (d4T), and TRIZIVIR (abacavir+zidovudine+lamivudine), nonnucleosides, e.g., efavirenz (DMP-266, DuPont Pharmaceuticals/Bristol Myers Squibb), nevirapine (Boehringer Ingleheim), and delaviridine (Pharmacia-Upjohn), TAT antagonists such as Ro 3-3335 and Ro 24-7429, protease inhibitors, e.g., indinavir (Merck), ritonavir (Abbott), saquinavir (Hoffmann LaRoche), nelfinavir (Agouron Pharmaceuticals), 141 W94 (Glaxo-Wellcome), atazanavir (Bristol Myers Squibb), amprenavir (Glaxo SmithKline), fosamprenavir (Glaxo SmithKline), tipranavir (Boehringer Ingleheim), KALETRA (lopinavir+ritonavir, Abbott), and other agents such as 9-(2-hydroxyethoxymethyl)guanine (acyclovir), interferon, e.g., alpha-interferon, interleukin II, and phosphonoformate (Foscarnet), or entry inhibitors, e.g., T20 (enfuvirtide, Roche/Trimeris) or UK-427,857 (Pfizer), or in conjunction with other immune modulation agents or treatments including bone marrow or lymphocyte transplants or other medications such as levamisol or thymosin which would increase lymphocyte numbers and/or function as is appropriate. Because many of these drugs are directed to different targets, e.g., viral integration, a synergistic may result with this combination.

In one embodiment, one or more compounds of the invention including those of the formulae herein are used in conjunction with one or more therapeutic agents useful for treatment or prevention of HIV, a symptom associated with HIV infection, or other disease or disease symptom such as a secondary infection or unusual tumor such as herpes, cytomegalovirus, Kaposi's sarcoma and Epstein-Barr virus-related lymphomas among others, that can result in HIV immunocompromised subjects.

In certain embodiments of the invention, one or more compounds of the invention including those of the formulae herein are used in conjunction with a standard HIV antiviral treatment regimens. Without being limited by theory, it is believed that this combination is advantageous in that the compound(s) of the formulae herein can activate latent HIV infected cells to replicate by stimulating lytic viral replication, thus making them susceptible to the co-administered standard HIV antiviral treatment regimens. In this manner, the latent or secondary reservoirs of HIV-infected cells are depleted through "controlled" activation (rather than serendipitous or uncontrolled activation), resulting in more complete elimination of infection. In another aspect, the treatment methods herein include administration of a so-called HIV-drug "cocktail" or combination therapy, wherein a combination of reverse transcriptase inhibitor(s) and HIV protease inhibitor(s) is co-administered.

In one aspect, the invention provides a method of inhibiting p97-associated deubiquitination. In one embodiment, the invention provides a method of inhibiting p97-associated deubiquitination in a subject, comprising administering to said subject an effective amount of an imidazolidinone compound.

In another aspect, the invention provides a method of inhibiting p97-associated deubiquitination in a subject, the method comprising the step of administering to the subject a compound of Formula I:

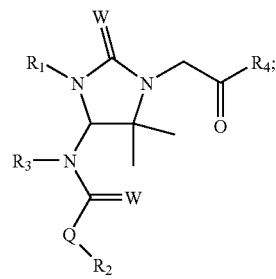

Formula I wherein
each occurrence of W is independently O, S, or NR$_A$;
Q is O, S, or NR$_A$;
R$_1$ is selected from hydrogen, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted haloalkyl, optionally substituted alkoxy, optionally substituted cycloalkoxy, optionally substituted (cycloalkyl)alkoxy, or optionally substituted heterocycloalkyl;
R$_2$ is selected from hydrogen, optionally substituted alkyl, optionally substituted cycloalkyl, optionally substituted aryl, optionally substituted heteroaryl, optionally substituted haloalkyl, optionally substituted alkoxy, optionally substituted cycloalkoxy, optionally substituted (cycloalkyl)alkoxy, or optionally substituted heterocycloalkyl;
R$_3$ is selected from hydrogen or hydroxyl;
R$_4$ is X—Y—Z;
wherein X is O, S, or NR$_B$;
Y is alkyl, alkenyl, or alkynyl, each of which may be substituted with a heteroatom; wherein at least one carbon of each alkyl, alkenyl, or alkynyl may be substituted by a heteroatom;
Z is an optionally substituted aryl or an optionally substituted heteroaryl;

each $R_A$ is independently selected from hydrogen, optionally substituted alkyl, optionally substituted aryl, or optionally substituted heteroaryl; and $R_B$ is selected from hydrogen or optionally substituted alkyl;

in an amount and under conditions sufficient to inhibit p97-associated deubiquitination.

In one embodiment, the subject is identified as being in need of inhibition of deubiquitination, and the compound of formula I is administered to the identified subject.

In still another aspect, the invention provides a method of modulating p97-associated deubiquitination in a cell, the method comprising the step of administering to the subject one or more compounds of Formula I in an amount and under conditions sufficient to modulate p97-associated deubiquitination.

In one embodiment, the modulation is a blocking regulation.

In another aspect, the invention provides for the use of an imidazolidinone compound in the manufacture of a medicament for inhibiting or reducing cancer in a patient, the compound being of formula I:

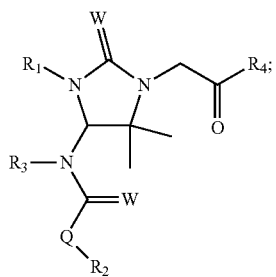

Formula I wherein
each occurrence of W is independently O, S, or $NR_A$;
Q is O, S, or $NR_A$;
$R_1$ is selected from hydrogen, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted haloalkyl, optionally substituted alkoxy, optionally substituted cycloalkoxy, optionally substituted (cycloalkyl)alkoxy, or optionally substituted heterocycloalkyl;
$R_2$ is selected from hydrogen, optionally substituted alkyl, optionally substituted cycloalkyl, optionally substituted aryl, optionally substituted heteroaryl, optionally substituted haloalkyl, optionally substituted alkoxy, optionally substituted cycloalkoxy, optionally substituted (cycloalkyl)alkoxy, or optionally substituted heterocycloalkyl;
$R_3$ is selected from hydrogen or hydroxyl;
$R_4$ is X—Y—Z;
wherein X is O, S, or $NR_B$;
Y is alkyl, alkenyl, or alkynyl, each of which may be substituted with a heteroatom; wherein at least one carbon of each alkyl, alkenyl, or alkynyl may be substituted by a heteroatom;
Z is an optionally substituted aryl or an optionally substituted heteroaryl;
each $R_A$ is independently selected from hydrogen, optionally substituted alkyl, optionally substituted aryl, or optionally substituted heteroaryl; and $R_B$ is selected from hydrogen or optionally substituted alkyl.

The imidazolidinone compounds of the formulae herein are useful in cancer therapies. Preferred compounds of the formulae herein show activity in tumor cells that are resistant to treatment with a proteasome inhibitor, including bortezomib (BZM). Additionally, the combination of an imidazolidinone compound of the invention and a proteasome inhibitor provide synergistic effects in the treatment of certain disorders, including cancer.

Therapeutic methods of invention include treating or preventing undesired cell growth, particularly cancer, tumors and the like. More preferably, the disease or disorder suitable for treatment by the methods of the invention include cancers selected from solid (tumors) and disseminated cancers particularly melanoma, carcinoma, leukemia, lymphoma, pediatric sarcoma, sarcoma, breast cancer, ovarian cancer, testicular cancer, prostate cancer, brain cancer, head or neck cancer, and lung cancer.

The present invention further provides methods of treating or preventing an undesired cell proliferation disease or disorder such as cancer comprising the administration of an imidazolidinone compound to a patient susceptible to or suffering from an undesired cell proliferation disease or disorder such as cancer. Preferred methods of the invention are suitable for use in anti-cancer therapies and comprise the administration of one or more compounds of the formulae herein, alone or in combination with other anti-cancer or anti-tumor therapeutics. Malignancies for treatment include both solid and disseminated cancers.

In a further aspect, the invention provides methods of treating or preventing a retroviral infection comprising the administration of an imidazolidinone compound to mammalian cells infected with or susceptible to infection by a retrovirus such as HIV. Therapeutic methods of the invention also include treating or preventing viral infections, particularly retroviral infections in mammalian cells, such as human cells infected with HIV. Such methods can include administering to a subject cells or a patient an effective amount of one or more imidazolidinone compounds particularly one or more compounds of the formulae herein. Preferably, such administration decreases or eliminates the pool of infected cells and/or decreases the viral population.

Therapeutic methods of the invention can also include the step of identifying that the subject is in need of treatment of diseases or disorders described herein, e.g., identifying that the subject is in need of treatment for cancer or treatment for a retroviral infection. The identification can be in the judgment of a subject or a health professional and can be subjective (e.g., opinion) or objective (e.g., measurable by a test or a diagnostic method). Tests for cancer are known and may include e.g. analysis of patient sample (e.g. biopsed tissue, or patient fluid such as blood, saliva, etc.) and for cancer cells or protein markers of a cancer. Tests for retroviral infection such as HIV infection are known in the art and include polymerase chain reaction-based (PCR-based) amplification and detection of viral RNA; Western blot detection of anti-HIV antibodies; agglutination assays for anti-HIV antibodies; ELISA-based detection of HIV-specific antigens (e.g., p24); and line immunoassay (LIA). In each of these methods, a sample of biological material, such as blood, plasma, semen, or saliva, is obtained from the subject to be tested. Thus, the methods of the invention can include the step of obtaining a sample of biological material (such as a bodily fluid) from a subject; testing the sample to determine the presence or absence of detectable cancer of retroviral infection such as HIV infection, HIV particles, or HIV nucleic acids; and determining whether the subject is in need of treatment according to the invention.

The methods delineated herein can further include the step of assessing or identifying the effectiveness of the treatment or prevention regimen in the subject by assessing the presence, absence, increase, or decrease of a marker, including a marker or diagnostic measure of cancer or of a retroviral infection such as HIV infection, HIV replication, viral load, or expression of an HIV infection marker; preferably this assessment is made relative to a measurement made prior to beginning the therapy. Such assessment methodologies are known in the art and can be performed by commercial diagnostic or medical organizations, laboratories, clinics, hospitals and the like. As described above, the methods can further include the step of taking a sample from the subject and analyzing that sample. The sample can be a sampling of cells, genetic material, tissue, or fluid (e.g., blood, plasma, sputum, etc.) sample. The methods can further include the step of reporting the results of such analyzing to the subject or other health care professional. The method can further include additional steps wherein (such that) the subject is treated for the indicated disease or disease symptom.

The present invention also comprises methods of modulating p97-associated deubiquitination in a subject, which suitably comprise administering to the subject one or more compounds of the formulae herein in an amount and under conditions sufficient to modulate p97-associated deubiquitination. Preferably, the modulation is down-regulation. Effective dosage amounts and administration protocols can be readily determined empirically, e.g. by standard efficacy evaluations. Efficacy and thus p97-associated deubiquitination modulation can be assessed e.g. by therapeutic benefit as discussed herein, such as in vitro or in vivo treatment against cancer or viral infection.

Compounds of the invention also will be useful to probe the function of the ubiquitin system and in inhibiting non-proteasomal functions of ubiquitination. In addition to its role in proteasomal degradation of target proteins, the ubiquitin system is also involved in a number of cellular processes unrelated to proteasomal degradation including endocytosis, trafficking in the endosomal system, viral budding, DNA repair, nucleocytoplasmic trafficking and kinase activation. Prior to the preferred present compounds, there have been limited tools that allow probing of the role of the ubiquitin system in these processes.

The invention demonstrates a deubiquitination inhibitor that can block a subset of deubiquitinating activities in intact cells. Since UPS plays a critical role in cell cycle progression, which is particularly essential for the survival of cancer cells, an UPS inhibitor such as, e.g., EerI, provides a therapeutic for certain types of cancer.

The finding that retrotranslocation substrates accumulate in polyubiquitinated form in the cytosol of EerI-treated cells is unexpected because a previous report suggested that EerI blocks substrate dislocation from the ER membrane (Fiebiger et al., 2004). In that work, cells treated with EerI for 8-16 hours were radiolabeled to follow the fate of newly synthesized substrates. Given the fact that polyubiquitinated proteins accumulate in EerI-treated cells, which should rapidly deplete the free ubiquitin pool, it is not surprising that long treatment with EerI can block dislocation, as it is known that polyubiquitination is essential for dislocation of HC in US11 cells (Kikkert et al., 2001; Shamu et al., 2001). By contrast, the invention examined the steady state accumulation of several ERAD substrates during the entire treatment period. Thus, assuming that the dislocation of newly synthesized substrates is blocked after a certain period of treatment with EerI, the cytosolic accumulation of polyubiquitinated intermediates that occurs prior to the inhibition of dislocation can still be detected with our method, but not with the published radiolabeling approach. The results also indicate that the previous classification of EerI as a specific ERAD inhibitor is an oversimplified view (Fiebiger et al., 2004). The fact that GFPµ, a soluble proteasomal substrate, is stabilized by EerI indicates that EerI can act on both membrane and soluble substrates. This finding also suggests that the target of EerI must reside in the cytosol. In support of this view, the data of the invention suggest that EerI targets p97-associated deubiquitination, which is essential for the degradation of p97-bound substrates including those extracted from the ER membrane.

The therapeutic methods of the invention generally comprise administration of an effective amount of one or more compounds of the invention to cells or a subject including a mammal, such as a primate, especially a human, in need of such treatment. The methods herein include administering to the subject (including a subject identified as in need of such treatment) an effective amount of a compound described herein, or a composition described herein to produce such effect.

The treatment methods of the invention also will be useful for treatment of mammals other than humans, including for veterinary applications such as to treat horses and livestock e.g. cattle, sheep, cows, goats, swine and the like, and pets (companion animals) such as dogs and cats.

For diagnostic or research applications, a wide variety of mammals will be suitable subjects including rodents (e.g. mice, rats, hamsters), rabbits, primates and swine such as inbred pigs and the like. Additionally, for in vitro applications, such as in vitro diagnostic and research applications, body fluids (e.g., blood, plasma, serum, cellular interstitial fluid, saliva, feces and urine) and cell and tissue samples of the above subjects will be suitable for use.

Compounds of the invention may be administered singularly (i.e., sole therapeutic agent of a regime) to treat or prevent diseases and conditions such as undesired cell proliferation and/or viral infection as disclosed herein.

Compounds of the invention also may be administered as a "cocktail" formulation, i.e., coordinated administration of one or more compounds of the invention together with one or more other active therapeutics.

Pharmaceutical Compositions

Compounds of the invention can be administered by a variety of routes, such as orally or by injection, e.g., intramuscular, intraperitoneal, subcutaneous or intravenous injection, or topically such as transdermally, vaginally and the like.

In a particular embodiment, the compounds of the invention are administered intravenously. Compounds of the invention may be suitably administered to a subject in the protonated and water-soluble form, e.g., as a pharmaceutically acceptable salt of an organic or inorganic acid, e.g., hydrochloride, sulfate, hemi-sulfate, phosphate, nitrate, acetate, oxalate, citrate, maleate, mesylate, etc. If the compound has an acidic group, e.g. a carboxy group, base additional salts may be prepared. Lists of additional suitable salts may be found, e.g., in *Remington's Pharmaceutical Sciences*, 17$^{th}$ ed., Mack Publishing Company, Easton, Pa.

Compounds of the invention can be employed, either alone or in combination with one or more other therapeutic agents as discussed above, as a pharmaceutical composition in mixture with conventional excipient, i.e., pharmaceutically acceptable organic or inorganic carrier substances suitable for oral, parenteral, enteral or topical application which do not deleteriously react with the active compounds and are not deleterious to the recipient thereof. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds.

Pharmaceutical compositions of the invention include a compound of the invention packaged together with instructions (written) for therapeutic use of the compound, particularly to treat a subject suffering from or susceptible to cancer.

For oral administration, pharmaceutical compositions containing one or more compounds of the invention may be formulated as e.g. tablets, troches, lozenges, aqueous or oily suspensions, dispersible powders or granules, emulsions, hard or soft capsules, syrups, elixers and the like. Typically suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

For parenteral application, e.g., sub-cutaneous, intraperitoneal or intramuscular, particularly suitable are solutions, preferably oily or aqueous solutions as well as suspensions, emulsions, or implants, including suppositories. Ampoules are convenient unit dosages.

The actual amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests conducted with regard to the foregoing guidelines. See also *Remington's Pharmaceutical Sciences*, supra. In general, a suitable effective dose of one or more compounds of the invention, particularly when using the more potent compound(s) of the invention, will be in the range of from 0.01 to 100 milligrams per kilogram of bodyweight of recipient per day, preferably in the range of from 0.01 to 20 milligrams per kilogram bodyweight of recipient per day, more preferably in the range of 0.05 to 4 milligrams per kilogram bodyweight of recipient per day; or any dosage range in which the low end of the range is any amount between 0.01 mg/kg/day and 90 mg/kg/day and the upper end of the range is any amount between 1 mg/kg/day and 100 mg/kg/day (e.g., 0.5 mg/kg/day and 2 mg/kg/day, 5 mg/kg/day and 20 mg/kg/day). The desired dose is suitably administered once daily, or several sub-doses, e.g. 2 to 4 sub-doses, are administered at appropriate intervals through the day, or other appropriate schedule. Such sub-doses may be administered as unit dosage forms, e.g., containing from 0.05 to 10 milligrams of compound(s) of the invention, per unit dosage; or any dosage range in which the low end of the range is any amount between 0.05 mg/day and 400 mg/day and the upper end of the range is any amount between 1 mg/day and 500 mg/day (e.g., 5 mg/day and 100 mg/day, 150 mg/day and 500 mg/day).

A "pharmaceutically acceptable derivative or prodrug" means any pharmaceutically acceptable salt, ester, salt of an ester, or other derivative of a compound of this invention which, upon administration to a recipient, is capable of providing (directly or indirectly) an active compound of this invention. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or central nervous system) relative to the parent species. Preferred prodrugs include derivatives where a group which enhances aqueous solubility or active transport through the gut membrane is appended to the structure of formulae described herein. See, e.g., Alexander, J. et al. *Journal of Medicinal Chemistry* 1988, 31, 318-322; Bundgaard, H. *Design of Prodrugs*; Elsevier: Amsterdam, 1985; pp 1-92; Bundgaard, H.; Nielsen, N. M. *Journal of Medicinal Chemistry* 1987, 30, 451-454; Bundgaard, H. *A Textbook of Drug Design and Development*; Harwood Academic Publ.: Switzerland, 1991; pp 113-191; Digenis, G. A. et al. *Handbook of Experimental Pharmacology* 1975, 28, 86-112; Friis, G. J.; Bundgaard, H. *A Textbook of Drug Design and Development*; 2 ed.; Overseas Publ.: Amsterdam, 1996; pp 351-385; Pitman, I. H. *Medicinal Research Reviews* 1981, 1, 189-214.

The invention also provides kits for treatment or prevention of a disease or disorder (or symptoms) thereof associated with ubiquitination. In one embodiment, the kit includes an effective amount of a compound herein in unit dosage form, together with instructions for administering the compound to a subject suffering from or susceptible to a disease or disorder or symptoms thereof associated with ubiquitination, wherein the effective amount of a compound is as described herein. In preferred embodiments, the kit comprises a sterile container which contains compound; such containers can be boxes, ampules, bottles, vials, tubes, bags, pouches, blister-packs, or other suitable container form known in the art. Such containers can be made of plastic, glass, laminated paper, metal foil, or other materials suitable for holding medicaments. The instructions will generally include information about the use of the compound for treatment of a disease or disorder or symptoms thereof associated with ubiquitination, including treatment of cell proliferative diseases and disorders and/or treatment of viral infections particularly retroviral infections such as HIV infections; in preferred embodiments, the instructions include at least one of the following: description of the compound; dosage schedule and administration for treatment of a disease or disorder or symptoms; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

EXAMPLES

This invention is further illustrated by the following examples which should not be construed as limiting. The contents of all references, patents and published patent applications cited throughout this application, as well as the figures, are incorporated herein by reference.

Example 1

Effect of EER on Cancer/Tumor

Experiments for FIGS. 1-5 were conducted in vitro by keeping cell lines in RPMI medium with 10% FCS and primary cells in AIM V medium. Cells were seeded into 96 well plates at a concentration of 4×10e5/ml for cell lines at a concentration of 5×10e6/mL for primary cells. Cells were incubated for 2 days (cell lines) or 3 days (primary samples) in the indicated concentration of drug (bortezomib from commercial clinical grade stock; EER1 provided by Dr. Ye and Dr. Trenkle). Viability was determined using the standard MTT assay. Synergy calculations were carried out with Calcusyn software.

Example 2

Accumulation of Polyubiquitinated Intermediates in EerI-treated Cells

The effect of EerI on the degradation of haemagglutinin (HA)-tagged MHC class I heavy chain (HC) in astrocytoma cells expressing the HCMV protein US11 (A9 cells) was examined. A9 cells were treated with EerI or, as a control, with DMSO. The cells were permeabilized in a buffer containing 0.028% of digitonin, and fractionated into a pellet fraction containing the ER membranes and a supernatant fraction containing the cytosol (Shamu et al., 1999; Ye et al., 2001, 2003). HC was immunoprecipitated from detergent extracts of these fractions under denaturing condition, and analyzed by immunoblotting (Shamu et al., 1999; Wang et al., 2006). Compared with DMSO-treated cells, polyubiquitinated HC was accumulated in the cytosol of EerI-treated cells (FIG. 6A, lanes 4, 6). As a positive control, A9 cells were treated with MG132, a proteasome inhibitor. Consistent with previous reports (Wiertz et al., 1996a; Shamu et al., 1999; Ye et al., 2001), inhibition of the proteasome function uncoupled dislocation and degradation, leading to accumulation of polyubiquitinated HC in the cytosol (FIG. 6B, lanes 4, 6). However, a significant fraction of HC accumulated in MG132-treated cells was non-ubiquitinated species with its N-linked glycan removed by a cytosolic N-glycanase (Hirsch et al., 2003; Blom et al., 2004). The accumulation of non-modified substrates upon inhibition of the proteasome function has been observed for many proteasomal substrates, and was generally attributed to deubiquitination by cytosolic DUBs. Interestingly, EerI-treated cells contained very few such deubiquitinated, deglycosylated HC molecules, although they accumulated a similar amount of polyubiquitinated HC. These results suggest that EerI may inhibit a deubiquitinating process required for the degradation of dislocated HC.

The effect of EerI and MG132 on the degradation of overexpressed TCRα-GFP, a glycoprotein dislocated from the ER membrane due to the lack of its assembly partner (Huppa and Ploegh, 1997; Yu and Kopito, 1999; DeLaBarre et al., 2006), was next examined. Similar to HC, polyubiquitinated TCRα-GFP was accumulated in MG132-treated cells together with a deubiquitinated, deglycosylated species (FIG. 6C, lane 3). In contrast, cells treated with EerI alone or with both EerI and MG132 accumulated polyubiquitinated TCRα-GFP (lanes 2, 4), but they contained few deubiquitinated, deglycosylated TCRα-GFP molecules. These data suggest that the deubiquitinating process inhibited by EerI is also involved in TCRα degradation, and this deubiquitinating process occurs upstream of the proteasome.

Consistent with the notion that EerI inhibits certain deubiquitinating processes, cells exposed to EerI started to accumulate polyubiquitinated proteins ~1.5 hours after treatment. In addition, for a given time period, EerI-treated cells accumulated more polyubiquitinated proteins than MG132-treated cells (FIG. 6D), even though EerI was shown to affect the degradation of a subset of proteasomal substrates (Fiebiger et al., 2004).

Example 3

EerI Inhibits p97-Associated Deubiquitination (PAD)

Figure 7A:
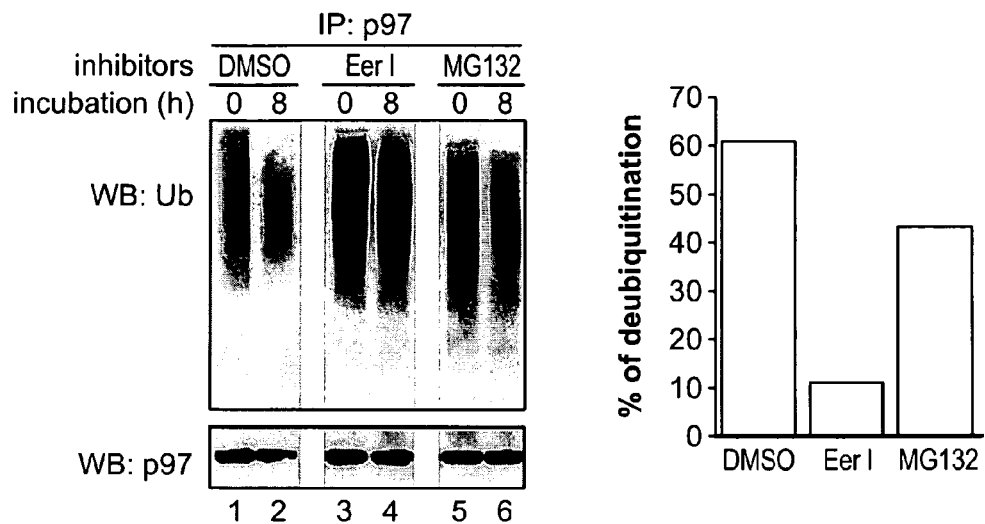
FIG. 7 shows that EerI inhibits p97-associated deubiquitination (PAD). (A) p97 and its associated proteins were immunoprecipitated from detergent extracts of DMSO-, MG132-, or EerI-treated cells, and incubated in vitro for the indicated time points. (B) As in A, except that ATP (5 mM) was included in the deubiquitinating reactions. Note that only 30% of the immunoprecipitated material for EerI-treated samples was loaded on the gel.
Figure 7B:
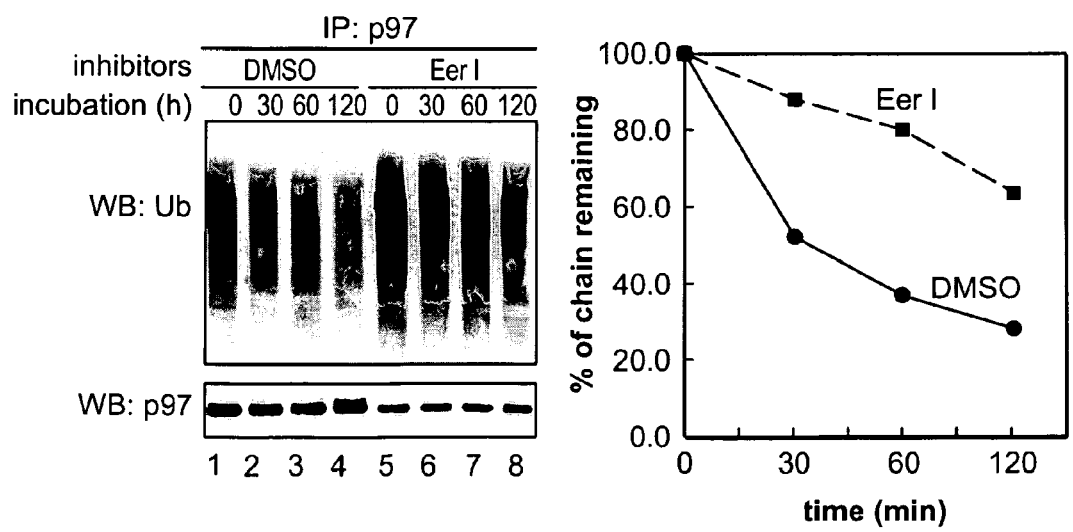

To study PAD, a previously established in vitro deubiquitination assay was used. p97 and its associated substrates immunoprecipitated from cell extracts were incubated in vitro. Ubiquitin chains on these substrates were deconjugated by deubiquitinating enzymes (DUBs) present in the precipitated complex, leading to a reduction in polyubiquitinated proteins (Wang et al., 2006). Interestingly, in vitro deubiquitination of p97 substrates was slow unless ATP was present (FIG. 7B). This is unlikely owing to ATP-dependent degradation of these substrates by the proteasome because the proteolytic subunit of the proteasome was not detected in p97 immunoprecipitates under this condition (Wang et al., 2006). Perhaps, p97-bound substrates needed to be released in an ATP dependent reaction before they could gain access to a p97-associated DUB.

Because addition of EerI to permeabilized US11 cells did not inhibit the retrotranslocation and degradation of MHC class I heavy chain, it was suspected that EerI may need to be metabolized into an active species in intact cells to exert its inhibitory effect. Consistent with this interpretation, US11 cells grown in suspension after being treated with trypsin no longer responded to EerI. These trypsin-treated cells apparently can still take up EerI because they became yellowish and autofluorescent after exposure to EerI (EerI is a yellow chemical that emits fluorescence at a wavelength of 488 nm). Thus, it is possible that trypsinization/permeabilization of cells disrupts certain cellular pathways required to activate EerI. For these reasons, we isolated p97-polyubiquitinated substrate complexes from either control or EerI-treated cells, and subjected them to in vitro deubiquitination. Compared with substrates from control cells, substrates isolated from EerI-treated cells were significantly more stable (only reduced by ~10% after incubation compared with ~60% for substrates isolated from non-treated cells) (FIG. 7A). Kinetic experiment further supports this conclusion (FIG. 7B). On the other hand, inhibition of the proteasome function did not apparently block PAD since ubiquitinated proteins bound to p97 from MG132-treated cells were also deubiquitinated (FIG. 7A, lane 6 vs. lane 5). Together, these data suggest that EerI blocks deubiquitination reactions associated with p97.

Example 4

EerI Inhibits atx3-Mediated Deubiquitination

Figure 8A:
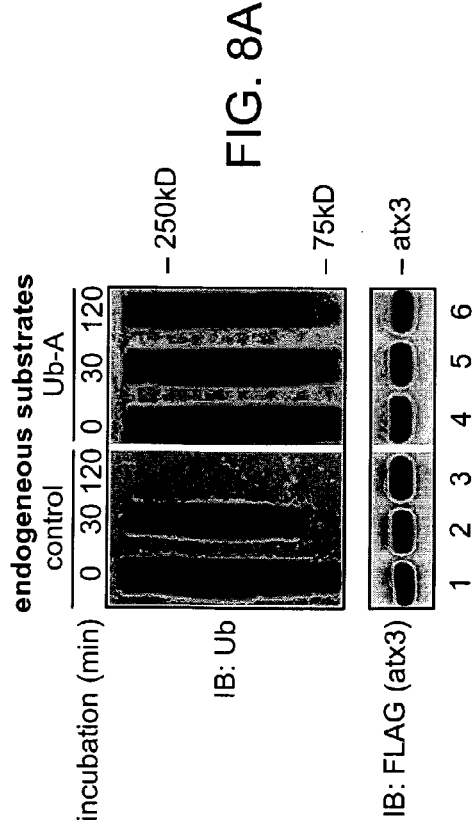
FIG. 8 shows that EerI inhibits atx3-dependent deubiquitination. (A) atx3-dependent deubiquitination. FLAG-tagged atx3 and its associated proteins were immunoprecipitated from detergent extracts of atx3-expressing cells. Precipitated materials were incubated in the absence or presence of ubiquitin aldehyde (Ub-A), and analyzed by immunoblotting (IB). (B, C) EerI inhibits atx3-dependent deubiquitination. (B), atx3 and its associated proteins immunoprecipitated from detergent extracts of DMSO- or EerI-treated cells (10 µM, 5 h) were incubated and analyzed as in A. (C) As in B, except that MG132-treated cells were also analyzed. (D) As in B, except that Ub2-7 was used in the deubiquitinating reaction as a substrate.

Since atx3 acts downstream of dislocation to promote deubiquitination of p97-bound substrates during retrotranslocation (Wang et al., 2006), a study to determine whether EerI affects atx3-associated deubiquitination was undertaken. To study atx3-dependent deubiquitination, atx3 and its associated substrates were immunoprecipitated from detergent extracts of 293T cells expressing FLAG-tagged atx3, and incubated in vitro Immunoblotting showed that ubiquitinated proteins bound by atx3 were rapidly turned over, which was apparently caused by deubiquitination because it could be inhibited by ubiquitin aldehyde, a deubiquitination inhibitor (FIG. 8A). Because substrates coprecipitated with deubiquitination defective atx3 mutant (atx3-C14A) that had its catalytic Cys substituted with an Ala remained stable under the same condition (Wang et al., 2006), the disappearance of atx3-associated substrates in this reaction is primarily caused by atx3-mediated deubiquitination.

Figure 8B:
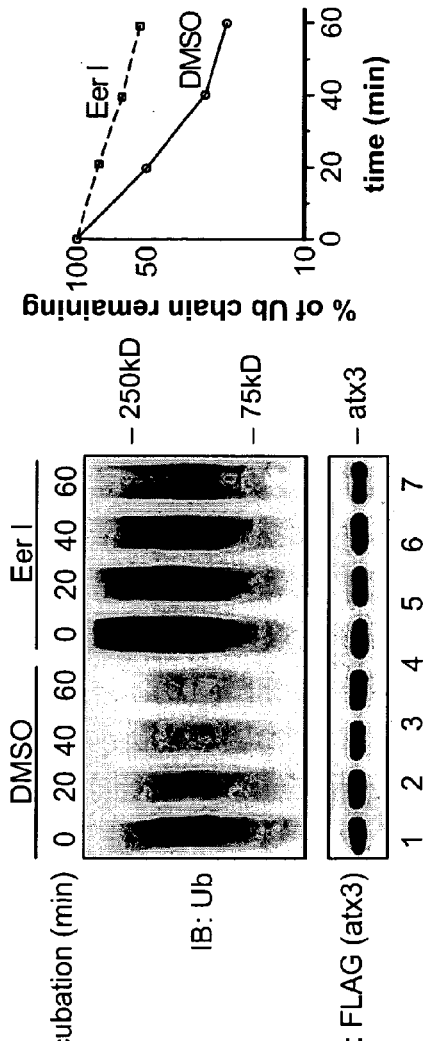
Figure 8C:
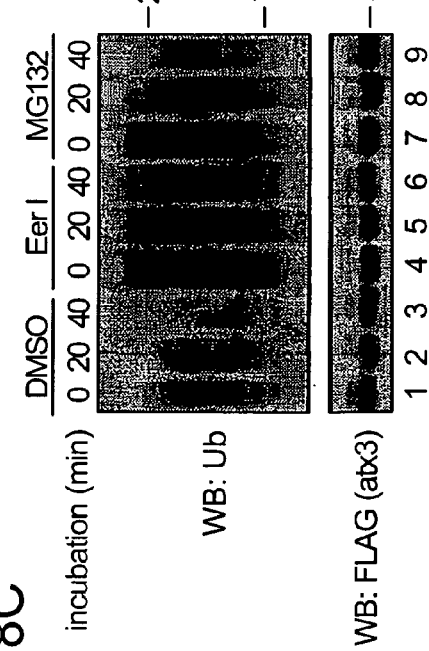
Figure 8D:
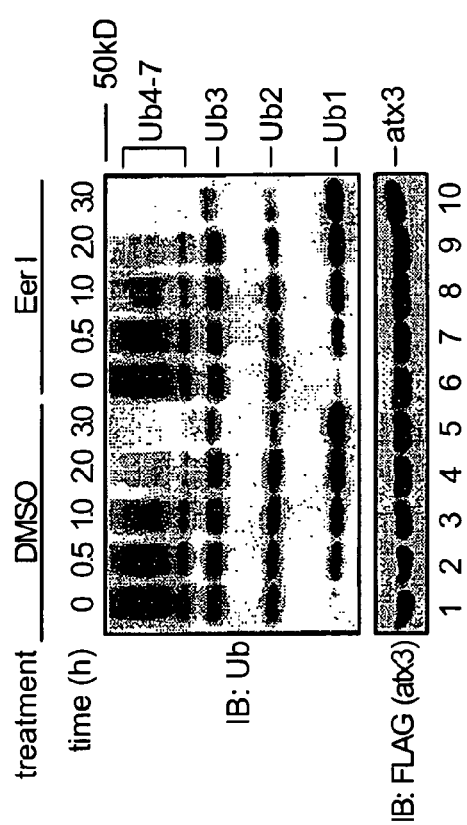

In accordance with the idea that EerI may need to be converted into an active form in cells before it can inhibit the degradation of p97 substrates, addition of EerI to purified atx3-substrate complex had no effect on atx3-mediated deubiquitination. The atx3-substrate complexes was isolated from DMSO-, EerI-, or MG132-treated cells, and analyzed the deubiquitination of these substrates in vitro. Compared with control cells, atx3-bound ubiquitin conjugates from EerI-treated cells were more resistant to deubiquitination (FIG. 8B, C). In contrast, ubiquitinated atx3 substrates isolated from MG132-treated cells were rapidly deconjugated in vitro similarly to those from control cells (FIG. 8C). These data indicate that EerI inhibits atx3-associated deubiquitination. Since atx3 purified from either DMSO- or EerI-treated cells was equally active in deubiquitinating exogenously added ubiquitin oligomers (Ub2-7) (FIG. 8D), EerI appears to inhibit atx3-associated deubiquitination without irreversibly abolishing its enzymatic activity. Further, because the association of p97 with atx3 was not affected in EerI-treated cells, EerI or its metabolites may influence atx3-associated deubiquitination possibly by acting on ubiquitin conjugates rather than on the enzyme.

Example 5

PAD is Not Required for Substrate Delivery to the Proteasome

Figure 9:
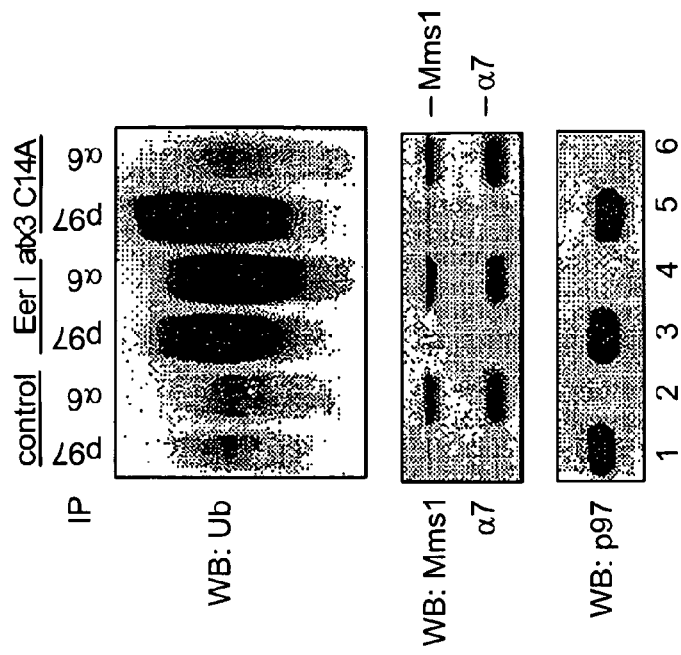
FIG. 9 shows that EerI does not prevent polyubiquitinated proteins from reaching the proteasome. Polyubiquitinated proteins are accumulated as both p97- and the proteasome-bound species in EerI-treated cells. Ubiquitinated proteins associated with p97 or with the proteasome were immunoprecipitated (IP) with either anti-p97 or anti-α6 antibodies, respectively, and analyzed by immunoblotting (IB).

In S. cerevisiae, ubiquitin chains on substrates of cdc48p, the homologue of p97, appear to be progressively shortened while substrates are being transferred to the proteasome (Richly et al., 2005). However, whether chain shortening per se is required for the proteasomal delivery of substrates is unclear. To address this question, a comparison between the relative amount of substrates bound by p97 vs. those associated with the proteasome was carried out. A blockage in substrate transfer should lead to the accumulation of ubiquitinated substrates bound to p97, resulting in an increase in the ratio of p97 bound-vs. the proteasome bound-substrates, as demonstrated previously by expressing a deubiquitinating defective atx3 mutant (C14A) (Wang et al., 2006). The detergent extracts of DMSO- or EerI-treated cells were subjected to immunoprecipitation with either p97 antibodies or antibodies against α6, a subunit of the 20S proteasome Immunoblotting showed that in DMSO-treated cells α6 antibodies precipitated the 26S proteasome (as indicated by the simultaneous presence of a7, another subunit of the 20S proteasome, and Mms1, a subunit of the 19S proteasome in the immunoprecipitates) together with some ubiquitinated proteins. Likewise, anti-p97antibodies precipitated similar amount of ubiquitinated substrates in complex with the ATPase itself (FIG. 9, lanes 1, 2). In EerI-treated cells, the levels of ubiquitinated proteins bound by p97 and by the proteasome were simultaneously increased, but their ratio remained unchanged (lanes 3, 4). This was in sharp contrast to atx3 C14A expressing cells, in which the accumulated polyubiquitinated substrates were mostly bound by p97 (Wang et al., 2006) (FIG. 9 lanes 5, 6). These data indicate that although EerI-treated cells contain elevated levels of polyubiquitin chains, these ubiquitin conjugates are partitioned among the components of the UPS pathway similarly as those in untreated cells. Thus, the lack of deubiquitination at p97 does not seem to cause any blockage in transferring polyubiquitinated proteins to the proteasome.

Example 6

EerI Inhibits the Degradation of GFPμ, a Soluble Proteasomal Substrate

Figure 10:
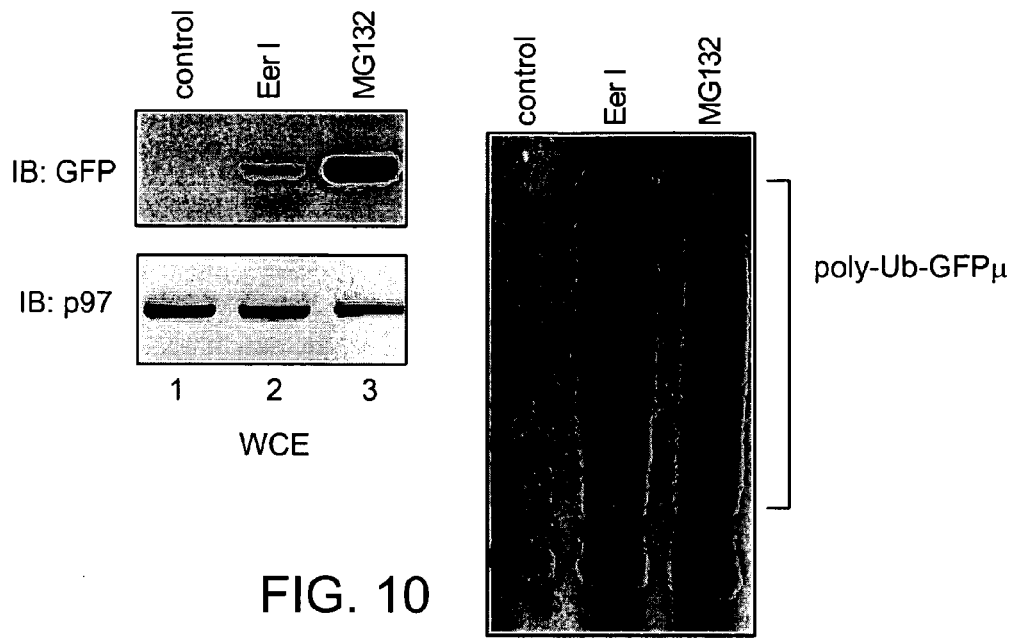
FIG. 10 shows that EerI inhibits the degradation of a cytosolic p97 substrate. Astrocytoma cells expressing HA-tagged GFPµ were treated with the indicated chemicals (12 h). The steady state levels of GFPµ in whole cell extracts (WCE) were analyzed by immunoblotting (IB). Where as indicated, GFPµ was first immunoprecipitated before immunoblotting analyses.

Since a large portion of p97 is localized in the cytosol, it may be involved in degradation of misfolded cytosolic proteins. In fact, GFPμ, a model proteasomal substrate (Bence et al., 2005) appeared to be degraded in a p97 dependent manner, because the expression of a dominant negative p97 mutant stabilized this substrate in part as a p97-associated form (data not shown). Interestingly, the degradation of GFPμ is also strongly influenced by the expression of an atx3 mutant (Burnett et al., 2003), raising the possibility that PAD may be involved in GFPμ degradation. Indeed, in EerI-treated cells, GFPμ was present almost exclusively as polyubiquitinated form. This was in contrast to MG132-treated cells in which GFPμ was mostly accumulated in the deubiquitinated form, and only to a lesser extent as polyubiquitinated species (FIG. 10). These data indicate that EerI also delays the degradation of a soluble p97 substrate likely by inhibiting its deubiquitination.

Example 7

EERI has Anti-Viral Activity

Figure 11:
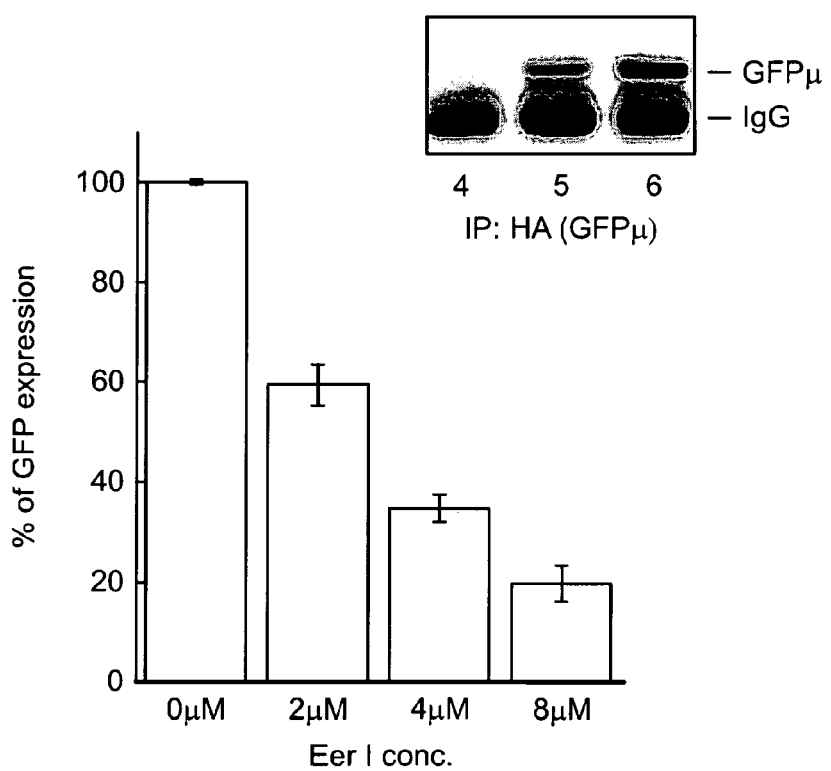
FIG. 11 shows that EERI can inhibit the production of a recombinant retrovirus that expresses a GFP reporter gene. The IC50 is ~3 uM.
Figure 12A:
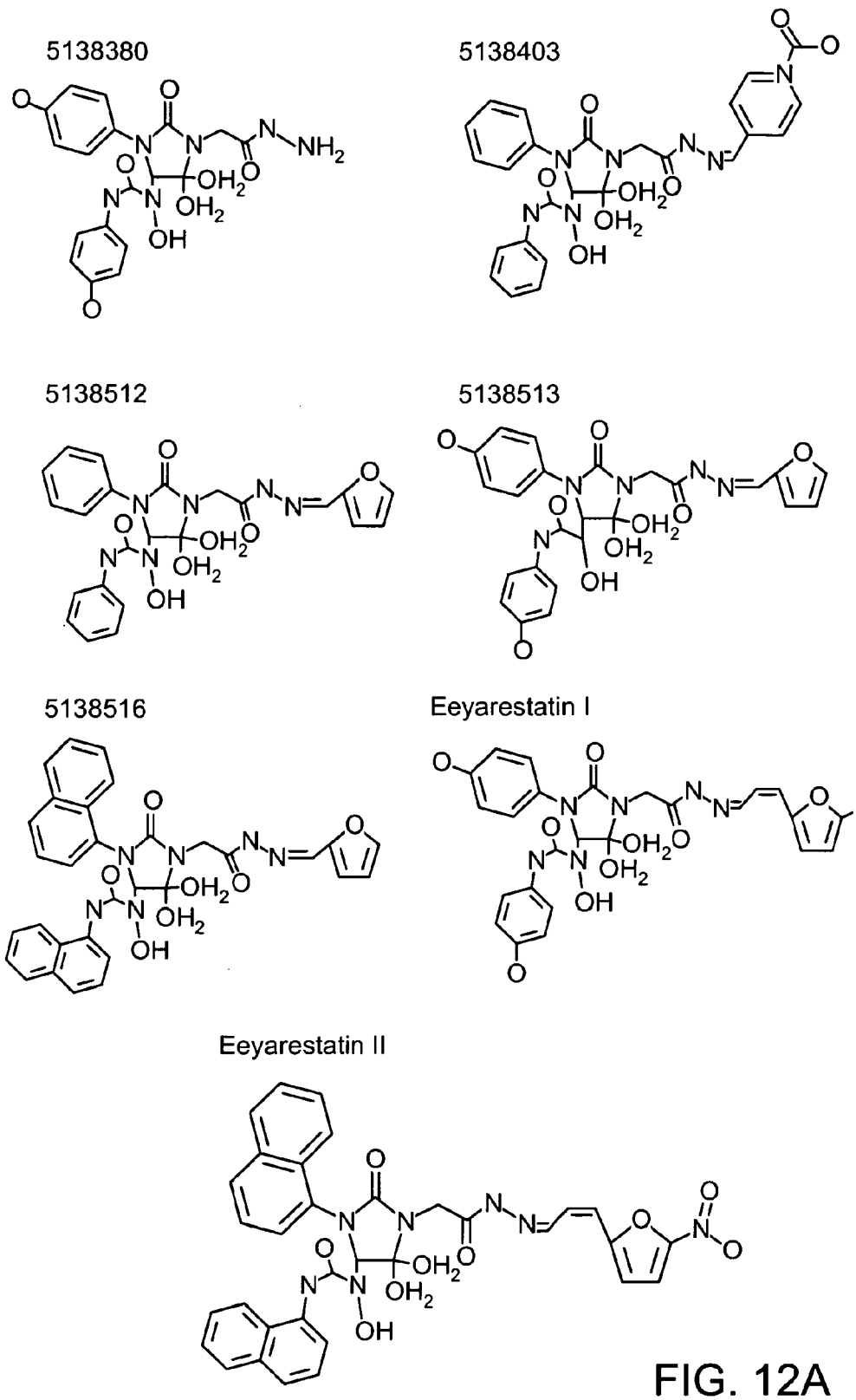
FIG. 12A provides various imidazolidinone compounds that were examined. The results show that with the exception of EerI and II, other analogues did not cause accumulation of polyubiquitinated proteins in cells (FIG. 12C, D). Consistent with this result, these chemical analogues are significantly less active in HBL2 cell toxicity assay (FIG. 12B).
Figure 12B:
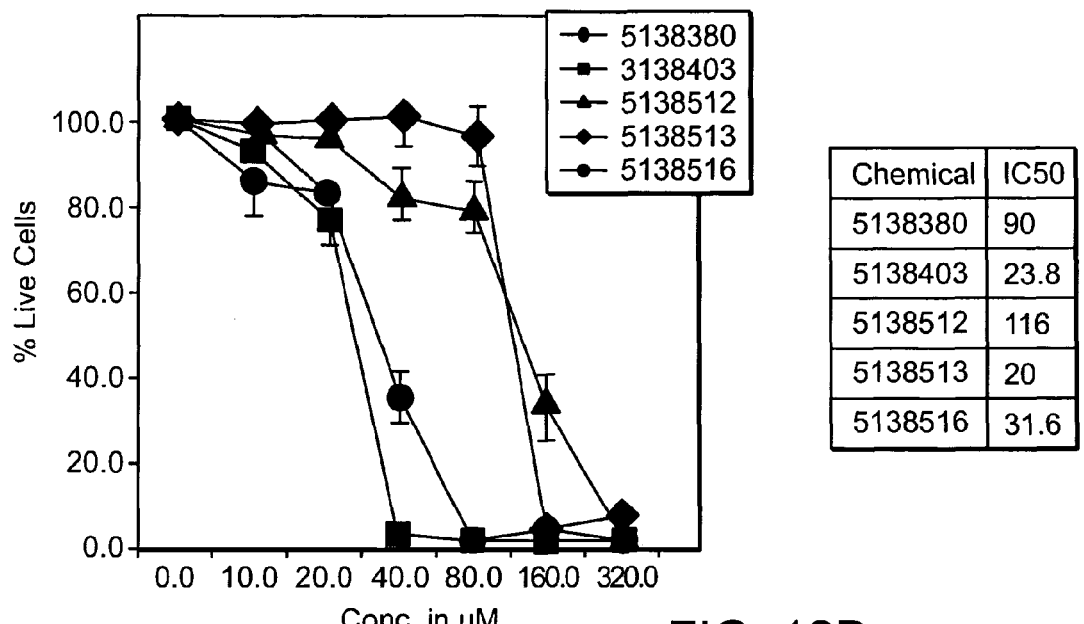
FIG. 12 shows the comparative effects of structurally related analogues of EERI on the inhibitory activity on deubiquitination.
Figure 12C:
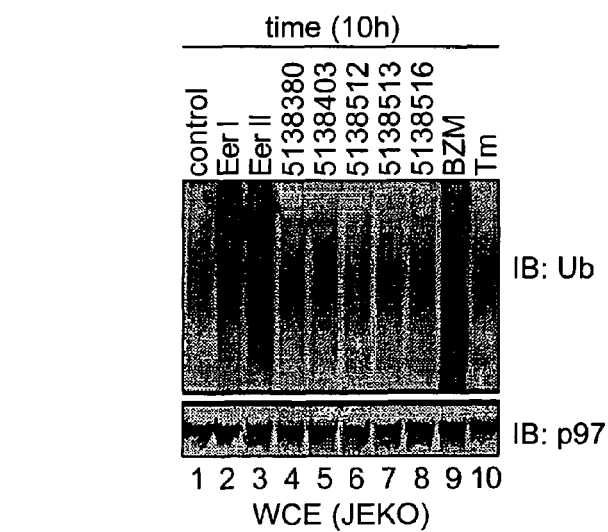
Figure 12D:
Figure 13A:
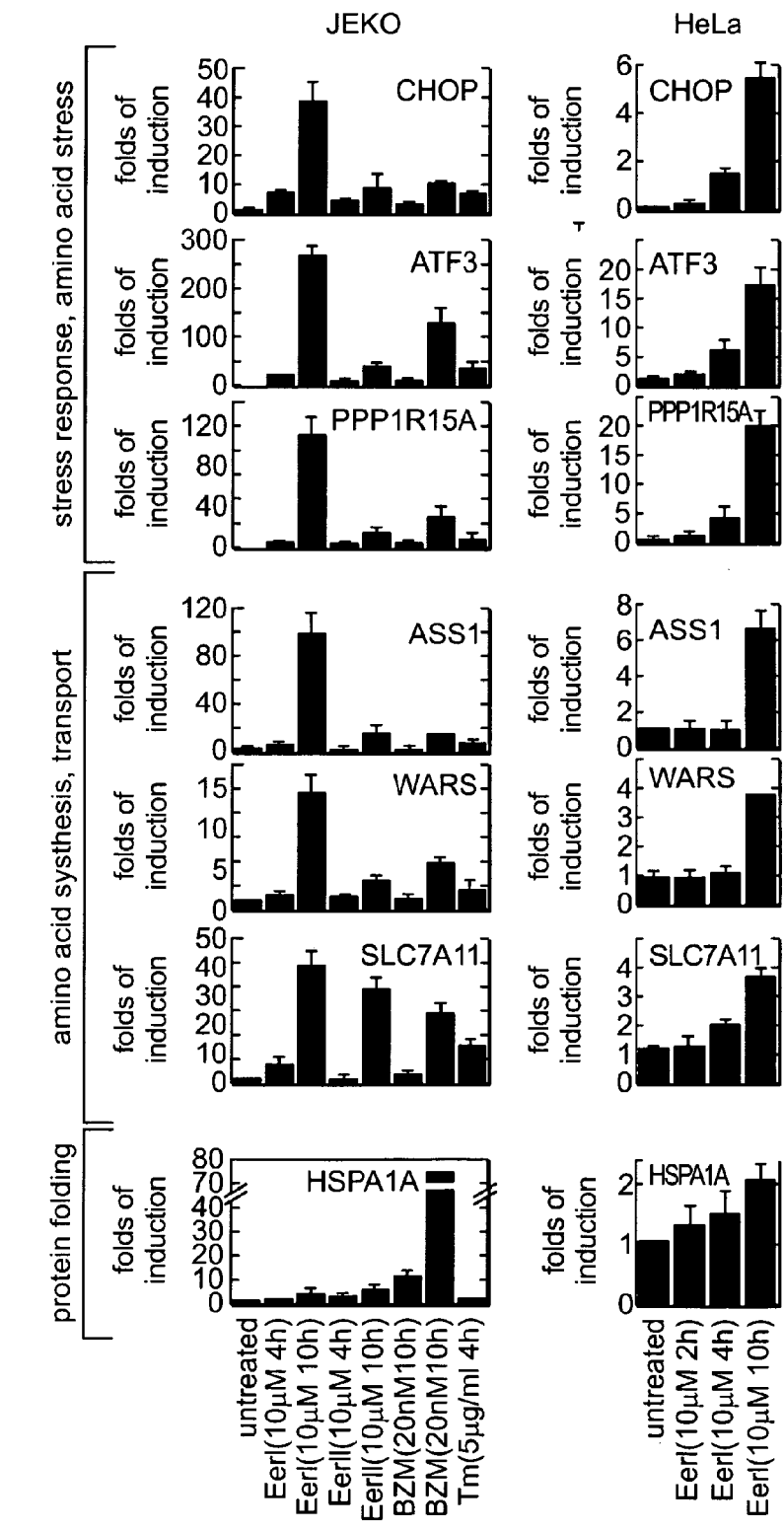
In FIG. 13, gene expression profiles were examined in cells treated with EerI, EerII, BZM (the proteasome inhibitor), and Tunicamycin (TM) by quantitative RT-PCR. The data indicates that EerI, BZM, and the ER stress inducer Tunicamycin, induce the expression of a similar set of genes. Thus, although EERI and BZM act on cells by different mechanisms, they both elicit ER stress responses, which may cause cell death. In particular, the data explain why EerI can potentiate the killing effect of BZM. The data also indicates that the combination of the two drugs may be a more effective therapy, as demonstrated in FIG. 5, because it can reduce the dose of both drugs, and thus reduce the side effect of each one.

GP293 packaging cells were transfected with a pLNCX2-GFP construct together with a plasmid expressing the viral protein VSVG. After transfection, the medium was replaced to include the indicated concentration of EERI. Medium that contains the viral particles was collected 36 hours later and was used to infect a target cells. Infection was allowed to proceed for 10 hours before the medium was replaced with fresh medium. The expression of the GFP protein as a result of viral infection was measured by a fluorescence meter. FIG. 11 shows that EERI can inhibit the production of a recombinant retrovirus that expresses a GFP reporter gene. The IC50 was ~3 uM.

To analyze the change in gene expression profile in cells treated with EERI, bortezomib, or tunicamycin, cells were lysed in the Trizol reagent, and the total RNA was precipitated by 2-propanol. The precipitated RNA was further purified by a RNA clean-up kit (Qiagen). The purified RNA was quantified, and used as template to synthesize cDNA. The expression of various genes was then determined by quantitative RT-PCR.

Example 8

EerI-Induced Cell Death Requires the BH3-Only Protein NOXA

Previous studies demonstrated that bortezomib activates the expression of NOXA, a BH3 domain-containing pro-apoptotic protein, to induce cytotoxicity in cancer cells (Fernandez et al., 2005; Fribley et al., 2006; Gomez-Bougie et al., 2007; Nikiforov et al., 2007; Perez-Galan et al., 2006; Qin et al., 2005; Rizzatti et al., 2008).

Figure 15A:
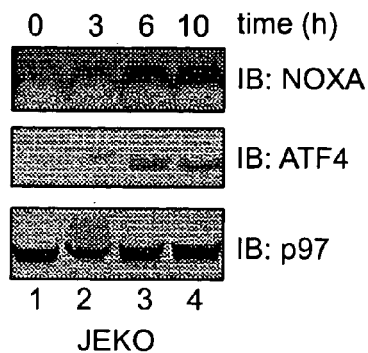
FIG. 15 shows that the effect of NOXA on EerI-induced cell death—(A-C) Induction of NOXA expression by EerI. (A) Cell extracts from JEKO-1 cells treated with EerI (10 µM) for the indicated time points were analyzed by immunoblotting with antibodies against the indicated proteins. (B) 293T cells were treated with EerI for 24 h. Protein extracts were analyzed by immunoblotting. (C) NOXA mRNA in EerI-treated JEKO-1 cells was determined by quantitative RT-PCR. (D) NOXA knock-down cells. JEKO-1 cells stably expressing two different NOXA shRNAs or a luciferase shRNA (shLuc) were treated with EerI (+) or with DMSO as a control (−) for 24 h. Protein extracts were analyzed by immunoblotting.—(E-G) NOXA knock-down protects cells from EerI-induced cell death. (E) JEKO-1 cells expressing the indicated shRNA were treated with EerI (5 µM) for 24 h. Cell death was determined by an annexin V-labeling apoptotic assay. Shown is the mean of two independent experiments with error bars representing the standard deviation of the mean estimate. (F) As in (E), except that cells were treated with the indicated concentrations of EerI, and that the parental JEKO-1 line was also included. (G) JEKO-1 cells expressing the indicated shRNA were treated with the indicated concentrations of EerI for 24 h. Cell viability was measured by the MTT assay. (H) EerI synergizes with a BH3 inhibitor (BH31-1). JEKO-1 cells were treated with the indicated compounds for 48 h. Cell viability was measured by the MTT assay.
Figure 15B:
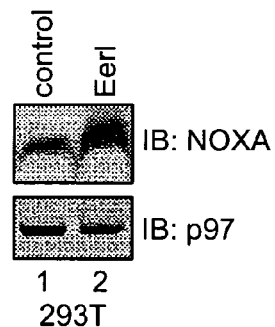
Figure 15C:
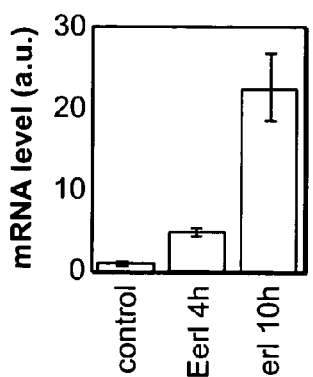
Figure 16:
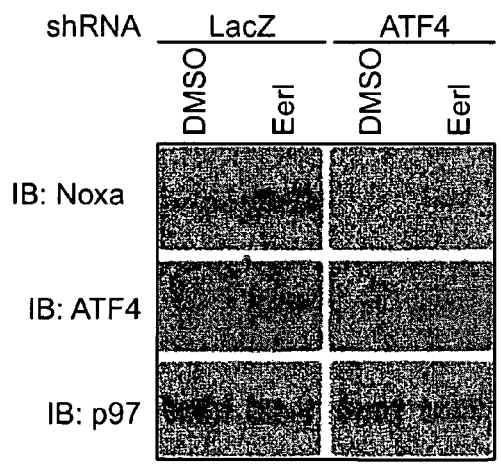
FIG. 16 shows ATF4 is required for NOXA activation by EerI. HeLa cells transfected with constructs expressing either a control shRNA or an ATF4 specific shRNA were treated as indicated. Cell extracts were analyzed by immunoblotting with the indicated antibodies.

The expression of NOXA in EerI-treated cells was analyzed and Immunoblotting showed that the level of NOXA protein was rapidly increased in a variety of cancer and transformed cell lines following treatment with EerI (FIG. 15A, B; FIG. 16; data not shown). Quantitative RT-PCR revealed a similar increase in NOXA mRNA in EerI-treated JEKO-1 cells (FIG. 15C), suggesting that the accumulation of NOXA protein in these cells is likely due to increased NOXA mRNA expression.

Figure 15D:
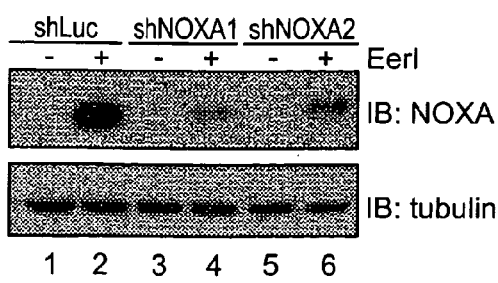

To see whether NOXA is involved in EerI-induced cell death, short hairpin RNA (shRNA) in JEKO-1 cells was stably expressed to knock down NOXA expression. Among five target sequences tested, two shRNA sequence designated as shNOXA1 and shNOXA2 could effectively downregulate NOXA (FIG. 15D). Untransfected JEKO-1 cells or cells stably expressing an irrelevant shRNA (shLuc) were used as controls.

Figure 15E:
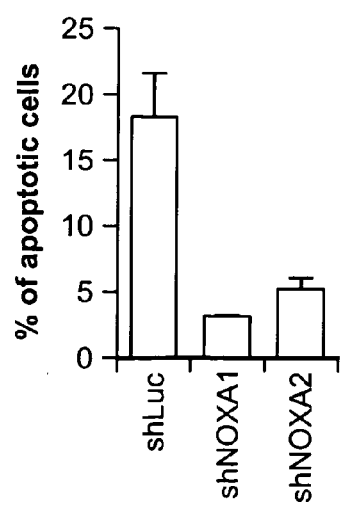
Figure 15F:
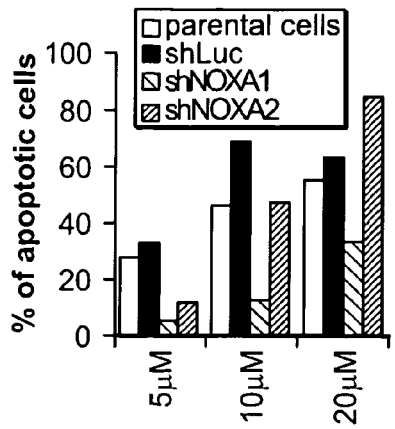
Figure 15G:
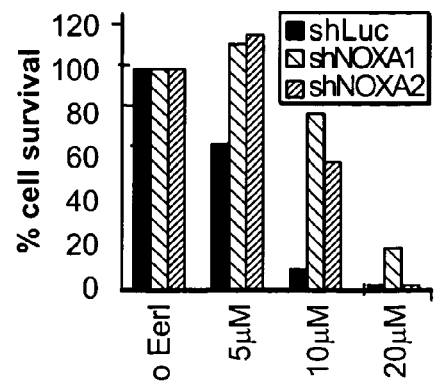

EerI-induced cytotoxicity was measured using both the MTT and a flow cytometry based annexin V-labeling assay. When the EerI concentration was relatively low (5 uM), the expression of shNOXA1 and shNOXA2 effectively protected cells from EerI-induced cell death to a similar degree (FIG. 15E). However, when exposed to higher concentrations of EerI, shNOXA2 cells were significantly more sensitive to EerI than shNOXA1 cells (FIG. 15F, G), consistent with the fact that shNOXA1 was more effective than shNOXA2 in downregulating NOXA (FIG. 15D; data not shown). These data indicate that NOXA plays an essential role in EerI-induced cytotoxicity.

Figure 15H:
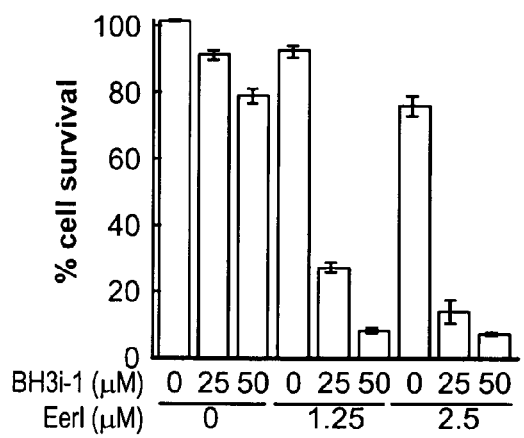

Since the pro-apoptotic activity of NOXA acts by interfering with the interaction between the pro-survival Bcl-2 family proteins and the death effectors BAX and BAK, chemicals that inhibit the interaction of Bcl-2 proteins with BAX or BAK should mimic the action of NOXA and therefore synergize with EerI. A previous high throughput screen identified two such Bcl-2 antagonists (Degterev et al., 2001). One of these BH3 mimetics (BH3i-1) was used in a combination treatment experiment with EerI. As a single agent BH31-1 did not induce significant toxicity in MCL cells (FIG. 15H), while the presence of EerI strongly enhanced its cytotoxicity (FIG. 15H). These data indicate that, similar to EerI induces apoptosis in hematological cancer cells by acting through the BH3-only protein NOXA.

Example 9

EERI Induces an Integrated Stress Response Program at the ER

Figure 17A:
FIG. 17 shows that EerI and bortezomib have overlapping as well as distinct activities (A-B) Microarray analyses of gene expression profiles of EerI- and bortezomib-treated JEKO-1 cells. (C) EerI and bortezomib activate an integrated ER stress response program. The mRNA levels of the indicated genes in JEKO-1 and JEKO 100BR cells following the treatment with either EerI (10 µM) or bortezomib (BZM, 20 nM) were determined by quantitative RT-PCR. Representative data from two independent experiments are shown. Error bars hereafter represent standard deviation of the PCR reactions estimated on the basis of triplicated samples.
Figure 17B:
Figure 17C:
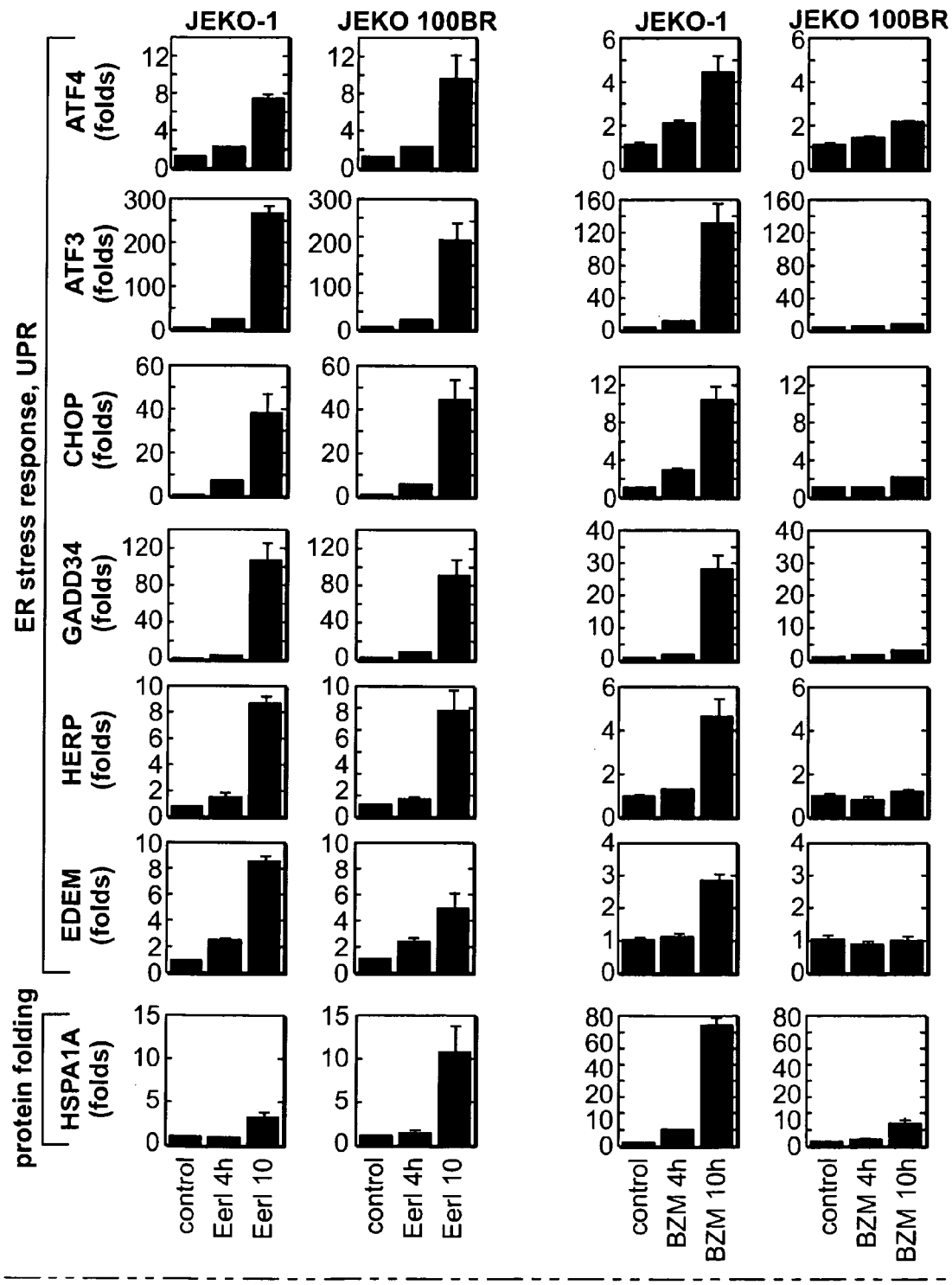

Genes upregulated in response to EerI include those involved in protein folding at the ER, ERAD, and amino acid import and metabolism (Supplemental table). These data indicate that an integrated stress response is elicited by EERI. Quantitative RT-PCR (qRT-PCR) using a select set of probes confirmed this observation (FIG. 17). As anticipated, EerI activated these ER stress genes in both JEKO-1 and JEKO 100BR cells.

The most highly upregulated genes in EerI treated cells included CHOP, GADD34, and ATF3, a transcription factor of the ATF/CREB family (FIG. 17; FIG. 18A). Moreover, a rapid accumulation of ATF4 protein was observed in response to EerI treatment in various cell lines, which was presumably caused by enhanced protein translation because the ATF4 mRNA level was only slightly increased in EerI-treated cells (FIG. 15A; FIG. 16). The above mentioned proteins constitute a pathway downstream of the protein kinase PERK to mediate responses to stress signals at the ER. Thus, the PERK branch of the UPR appeared to be activated by EerI. This conclusion was supported by the observation that EerI induced eIF2α phosphorylation (FIG. 18B), an event directly mediated by PERK.

To further characterize the effect of EerI on ER homeostasis, the effect of EerI on the splicing of)(bpi mRNA was assayed, which gives rise to an)(bpi variant lacking a small intron (FIG. 18C). The splicing of)(bpi is a direct indicator of Ire1 activation in response to ER stress. RT-PCR analyses in JEKO-1 cells treated with EerI showed that EerI induced the splicing of Xbp1. EerI also induced)(bpi splicing in wild type, but not Ire1α deficient MEF cells (FIG. 18D), suggesting that EerI activates the Ire1 branch of the UPR.

Finally, the effect of EerI on the activation of ATF6 was tested, using HeLa cells. As a positive control, dithiothreitol (DTT), a reducing agent that interfered with protein folding in the ER was used Immunoblotting showed that DTT rapidly induced the cleavage of ATF6 (FIG. 18E, lane 4), as previously demonstrated (Haze et al., 1999; Shen et al., 2002). In contrast, no increase in ATF6 cleavage was observed in EerI-treated cells (FIG. 18E, lanes 1-3) Immunofluorescence experiments further demonstrated that, in EerI-treated cells, most ATF6 remained associated with the ER (FIG. 18F, panel 3). This is in contrast to cells exposed to DTT, in which rapid translocation of ATF6 to the Golgi was observed (FIG. 18F, panel 2 versus panel 1). Together, these results suggest that in contrast to agents impairing protein folding at the ER, EerI activates an integrated ER stress program that includes the PERK and Ire1 branches.

All references cited herein, whether in print, electronic, computer readable storage media or other form, are expressly incorporated by reference in their entirety, including but not limited to, abstracts, articles, journals, publications, texts, treatises, technical data sheets, internet web sites, databases, patents, patent applications, and patent publications.

EQUIVALENTS

Those skilled in the art will recognize, or be able to ascertain using no more than routine experimentation, many equivalents to the specific embodiments of the invention described herein. Such equivalents are intended to be encompassed by the following claims.

REFERENCES

Adams, J. (2004). The development of proteasome inhibitors as anticancer drugs. Cancer Cell 5, 417-421.

Bays, N. W., Wilhovsky, S. K., Goradia, A., Hodgkiss-Harlow, K., and Hampton, R. Y. (2001). HRD4/NPL4 Is Required for the Proteasomal Processing of Ubiquitinated ER Proteins. Mol Biol Cell 12, 4114-4128.

Bence, N. F., Bennett, E. J., and Kopito, R. R. (2005). Application and Analysis of the GFP(u) Family of Ubiquitin-Proteasome System Reporters. Methods Enzymol 399, 481-490.

Blom, D., Hirsch, C., Stern, P., Tortorella, D., and Ploegh, H. L. (2004). A glycosylated type I membrane protein becomes cytosolic when peptide: N-glycanase is compromised. Embo J 23, 650-658.

Braun, S., Matuschewski, K., Rape, M., Thoms, S., and Jentsch, S. (2002). Role of the ubiquitin-selective CDC48 (UFD1/NPL4)chaperone (segregase) in ERAD of OLE1 and other substrates. Embo J 21, 615-621.

Burnett, B., Li, F., and Pittman, R. N. (2003). The polyglutamine neurodegenerative protein ataxin-3 binds polyubiquitylated proteins and has ubiquitin protease activity. Hum Mol Genet. 12, 3195-3205.

Carvalho, P., Goder, V., and Rapoport, T. A. (2006). Distinct ubiquitin-ligase complexes define convergent pathways for the degradation of ER proteins. Cell 126, 361-373.

DeLaBarre, B., Christianson, J. C., Kopito, R. R., and Brunger, A. T. (2006). Central pore residues mediate the p97/VCP activity required for ERAD. Mol Cell 22, 451-462.

Denic, V., Quan, E. M., and Weissman, J. S. (2006). A luminal surveillance complex that selects misfolded glycoproteins for ER-associated degradation. Cell 126, 349-359.

Fiebiger, E., Hirsch, C., Vyas, J. M., Gordon, E., Ploegh, H. L., and Tortorella, D. (2004). Dissection of the dislocation pathway for type I membrane proteins with a new small molecule inhibitor, eeyarestatin. Mol Biol Cell 15, 1635-1646.

Friedlander, R., Jarosch, E., Urban, J., Volkwein, C., and Sommer, T. (2000). A regulatory link between ER-associated protein degradation and the unfolded-protein response. Nat Cell Biol 2, 379-384.

Gauss, R., Jarosch, E., Sommer, T., and Hirsch, C. (2006). A complex of Yos9p and the HRD ligase integrates endoplasmic reticulum quality control into the degradation machinery. Nat Cell Biol 8, 849-854.

Hampton, R. Y. (2002). ER-associated degradation in protein quality control and cellular regulation. Curr Opin Cell Biol 14, 476-482.

Hirsch, C., Blom, D., and Ploegh, H. L. (2003). A role for N-glycanase in the cytosolic turnover of glycoproteins. Embo J 22, 1036-1046.

Hitchcock, A. L., Krebber, H., Frietze, S., Lin, A., Latterich, M., and Silver, P. A. (2001). The conserved np14 protein complex mediates proteasome-dependent membrane-bound transcription factor activation. Mol Biol Cell 12, 3226-3241.

Huppa, J. B., and Ploegh, H. L. (1997). The alpha chain of the T cell antigen receptor is degraded in the cytosol. Immunity 7, 113-122.

Kikkert, M., Hassink, G., Barel, M., Hirsch, C., van der Wal, F. J., and Wiertz, E. (2001). Ubiquitination is essential for human cytomegalovirus US11-mediated dislocation of MHC class 1 molecules from the endoplasmic reticulum to the cytosol. Biochem J 358, 369-377.

Lilley, B. N., and Ploegh, H. L. (2004). A membrane protein required for dislocation of misfolded proteins from the ER. Nature 429, 834-840.

Lilley, B. N., and Ploegh, H. L. (2005a). Multiprotein complexes that link dislocation, ubiquitination, and extraction of misfolded proteins from the endoplasmic reticulum membrane. Proc Natl Acad Sci USA 102, 14296-14301.

Lilley, B. N., and Ploegh, H. L. (2005b). Viral modulation of antigen presentation: manipulation of cellular targets in the ER and beyond. Immunol Rev 207, 126-144.

Meusser, B., Hirsch, C., Jarosch, E., and Sommer, T. (2005). ERAD: the long road to destruction. Nat Cell Biol 7, 766-772.

Neuber, O., Jarosch, E., Volkwein, C., Walter, J., and Sommer, T. (2005). Ubx2 links the Cdc48 complex to ER-associated protein degradation. Nat Cell Biol 7, 993-998.

Ng, D. T., Spear, E. D., and Walter, P. (2000). The unfolded protein response regulates multiple aspects of secretory and membrane protein biogenesis and endoplasmic reticulum quality control. J Cell Biol 150, 77-88.

Rabinovich, E., Kerem, A., Frohlich, K. U., Diamant, N., and Bar-Nun, S. (2002). AAA-ATPase p97/Cdc48p, a Cytosolic Chaperone Required for Endoplasmic Reticulum-Associated Protein Degradation. Mol Cell Biol 22, 626-634.

Richly, H., Rape, M., Braun, S., Rumpf, S., Hoege, C., and Jentsch, S. (2005). A series of ubiquitin binding factors connects CDC48/p97 to substrate multiubiquitylation and proteasomal targeting. Cell 120, 73-84.

Schuberth, C., and Buchberger, A. (2005). Membrane-bound Ubx2 recruits Cdc48 to ubiquitin ligases and their substrates to ensure efficient ER-associated protein degradation. Nat Cell Biol 7, 999-1006.

Shamu, C. E., Flierman, D., Ploegh, H. L., Rapoport, T. A., and Chau, V. (2001). Polyubiquitination Is Required for US11-dependent Movement of MHC Class I Heavy Chain from Endoplasmic Reticulum into Cytosol. Mol Biol Cell 12, 2546-2555.

Shamu, C. E., Story, C. M., Rapoport, T. A., and Ploegh, H. L. (1999). The pathway of US11-dependent degradation of MHC class I heavy chains involves a ubiquitin-conjugated intermediate. J Cell Biol 147, 45-58.

Swanson, R., Locher, M., and Hochstrasser, M. (2001). A conserved ubiquitin ligase of the nuclear envelope/endoplasmic reticulum that functions in both ER-associated and Matalpha2 repressor degradation. Genes Dev 15, 2660-2674.

Taxis, C., Hitt, R., Park, S. H., Deak, P. M., Kostova, Z., and Wolf, D. H. (2003). Use of modular substrates demonstrates mechanistic diversity and reveals differences in chaperone requirement of ERAD. J Biol Chem 278, 35903-35913.

Travers, K. J., Patil, C. K., Wodicka, L., Lockhart, D. J., Weissman, J. S., and Walter, P. (2000). Functional and genomic analyses reveal an essential coordination between the unfolded protein response and ER-associated degradation. Cell 101, 249-258.

Vashist, S., and Ng, D. T. (2004). Misfolded proteins are sorted by a sequential checkpoint mechanism of ER quality control. J Cell Biol 165, 41-52.

Verma, R., Aravind, L., Oania, R., McDonald, W. H., Yates, J. R., 3rd, Koonin, E. V., and Deshaies, R. J. (2002). Role of Rpn11 metalloprotease in deubiquitination and degradation by the 26S proteasome. Science 298, 611-615.

Wang, Q., Li, L., and Ye, Y. (2006). Regulation of retrotranslocation by p97-associated deubiquitinating enzyme ataxin-3. J Cell Biol 174, 963-971.

Wiertz, E. J. H. J., Jones, T. R., Sun, L., Bogyo, M., Geuze, H. J., and Ploegh, H. L. (1996a). The human cytomegalovirus US11 gene product dislocates MHC class I heavy chains from the endoplasmic reticulum to the cytosol. Cell 84, 769-779.

Wiertz, E. J. H. J., Tortorella, D., Bogyo, M., Yu, J., Mothes, W., Jones, T. R., Rapoport, T. A., and Ploegh, H. L. (1996b). Sec61-mediated transfer of a membrane protein from the endoplasmic reticulum to the proteasome for destruction. Nature 384, 432-438.

Yao, T., and Cohen, R. E. (2002). A cryptic protease couples deubiquitination and degradation by the proteasome. Nature 419, 403-407.

Ye, Y. (2006). Diverse functions with a common regulator: ubiquitin takes command of an AAA ATPase. J Struct Biol 156, 29-40.

Ye, Y., Meyer, H. H., and Rapoport, T. A. (2001). The AAA ATPase Cdc48/p97 and its partners transport proteins from the ER into the cytosol. Nature 414, 652-656.

Ye, Y., Meyer, H. H., and Rapoport, T. A. (2003). Function of the p97-Ufd1-Np14 complex in retrotranslocation from the ER to the cytosol: dual recognition of nonubiquitinated polypeptide segments and polyubiquitin chains. J Cell Biol 162, 71-84.

Ye, Y., Shibata, Y., Kikkert, M., van Voorden, S., Wiertz, E., and Rapoport, T. A. (2005). Inaugural Article Recruitment of the p97 ATPase and ubiquitin ligases to the site of retrotranslocation at the endoplasmic reticulum membrane. Proc Natl Acad Sci USA 102, 14132-14138.

Ye, Y., Shibata, Y., Yun, C., Ron, D., and Rapoport, T. A. (2004). A membrane protein complex mediates retrotranslocation from the ER lumen into the cytosol. Nature 429, 841-847.

Yu, H., and Kopito, R. R. (1999). The role of multiubiquitination in dislocation and degradation of the alpha subunit of the T cell antigen receptor. J Biol Chem 274, 36852-36858.

Zhong, X., and Pittman, R. N. (2006). Ataxin-3 binds VCP/p97 and regulates retrotranslocation of ERAD substrates. Hum Mol Genet. 15, 2409-2420.

Zhong, X., Shen, Y., Ballar, P., Apostolou, A., Agami, R., and Fang, S. (2004). AAA ATPase p97/valosin-containing protein interacts with gp78, a ubiquitin ligase for endoplasmic reticulum-associated degradation. J Biol Chem 279, 45676-45684.

What is claimed is:

1. A method of inhibiting p97 associated deubiquitination and/or inducing ER stress in a subject in need thereof, comprising administering to said subject, an effective amount of a compound of the following Formula (II), or pharmaceutically acceptable salt, solvate or hydrate thereof:

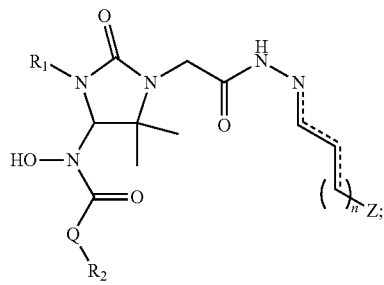

Formula II wherein

Q is O, S, or NR$_A$;

R$_1$ is selected from hydrogen, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted haloalkyl, optionally substituted alkoxy, optionally substituted cycloalkoxy, optionally substituted (cycloalkyl)alkoxy, and optionally substituted heterocycloalkyl;

R$_2$ is selected from hydrogen, optionally substituted alkyl, optionally substituted cycloalkyl, optionally substituted aryl, optionally substituted heteroaryl, optionally substituted haloalkyl, optionally substituted alkoxy, optionally substituted cycloalkoxy, optionally substituted (cycloalkyl)alkoxy, and optionally substituted heterocycloalkyl;

Z is an optionally substituted aryl or an optionally substituted heteroaryl; and n is 0-3.

2. A method of claim 1, wherein the subject is suffering from leukemia, multiple myeloma or lymphoma.

3. The method of claim 2 additionally comprising administering a proteasome inhibitor to the subject.

4. The method of claim 3, wherein the proteasome inhibitor is BORTEZOMIB.

5. A method for treating for leukemia, lymphoma, or multiple myeloma in a subject, the method comprising administering to said subject an effective amount of a compound of formula II:

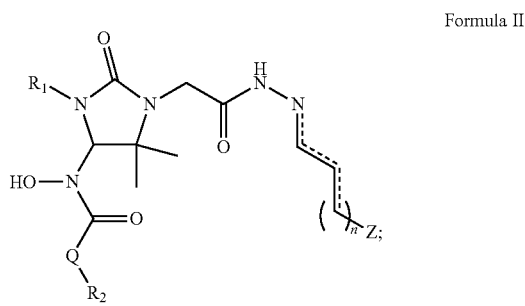

Formula II wherein

Q is O, S, or NR$_A$;

R$_1$ is selected from hydrogen, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted haloalkyl, optionally substituted alkoxy, optionally substituted cycloalkoxy, optionally substituted (cycloalkyl)alkoxy, and optionally substituted heterocycloalkyl;

R$_2$ is selected from hydrogen, optionally substituted alkyl, optionally substituted cycloalkyl, optionally substituted aryl, optionally substituted heteroaryl, optionally substituted haloalkyl, optionally substituted alkoxy, optionally substituted cycloalkoxy, optionally substituted (cycloalkyl)alkoxy, and optionally substituted heterocycloalkyl;

wherein X is O, S, or NR$_B$;

Z is an optionally substituted aryl or an optionally substituted heteroaryl;

and n is 0-3.

6. The method of claim 5, wherein the compound of formula II is:

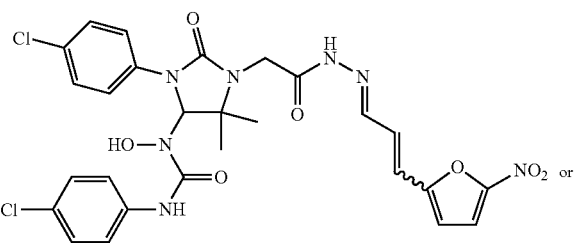

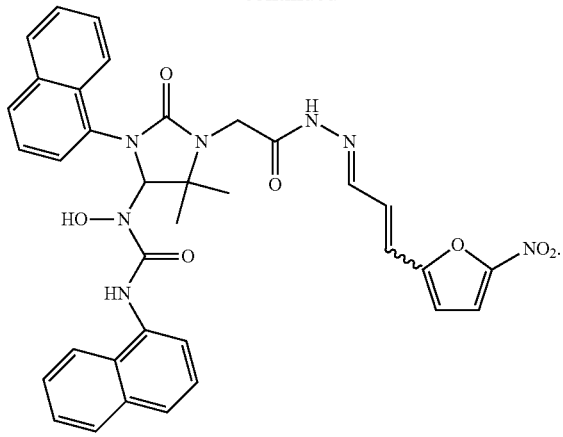

7. The method of claim 5, further comprising an additional therapeutic agent, wherein the additional therapeutic agent is an antineoplastic agent selected from wherein the additional therapeutic agent is an antineoplastic agent selected from an alkylating agent, a folate antagonist, a purine antagonist, a pyrimidine antagonist, a taxane, a topoisomerase, or a therapeutic antibody directed against CD20 or VEGF, or a combination of any of the foregoing.

8. A method of treating a treating a subject suffering from a retroviral infection, comprising administering a compound of the following Formula (II), or pharmaceutically acceptable salt, solvate or hydrate thereof to the subject:

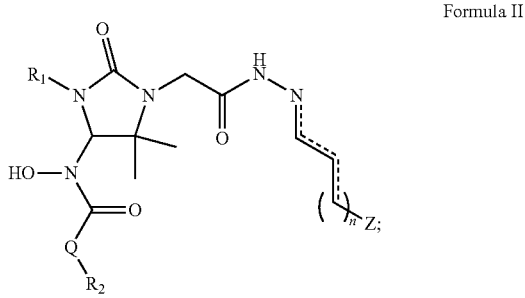

Formula II wherein

Q is O, S, or $NR_4$;

$R_1$ is selected from hydrogen, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted haloalkyl, optionally substituted alkoxy, optionally substituted cycloalkoxy, optionally substituted (cycloalkyl)alkoxy, and optionally substituted heterocycloalkyl;

$R_2$ is selected from hydrogen, optionally substituted alkyl, optionally substituted cycloalkyl, optionally substituted aryl, optionally substituted heteroaryl, optionally substituted haloalkyl, optionally substituted alkoxy, optionally substituted cycloalkoxy, optionally substituted (cycloalkyl)alkoxy, and optionally substituted heterocycloalkyl;

Z is an optionally substituted aryl or an optionally substituted heteroaryl; and n is 0-3.

9. The method of claim 2, wherein the subject is resistant to treatment with a proteasome inhibitor.

10. The method of claim 2, wherein the subject is resistant to treatment with BORTEZOMIB.

11. The method of claim 5, wherein the subject is resistant to treatment with a proteasome inhibitor.

12. The method of claim 5, wherein the subject is resistant to treatment with BORTEZOMIB.

13. The method of claim 5, further comprising administering an additional therapeutic agent to the subject, wherein the additional therapeutic agent is an antineoplastic agent selected from an alkylating agent, a folate antagonist, a purine antagonist, a pyrimidine antagonist, a taxane, a topoisomerase, or a therapeutic antibody directed against CD20 or VEGF, or a combination of any of the foregoing.

14. The method of claim 7, wherein the additional therapeutic agent is an anticancer compound, chosen from mechloroethamine, chlorambucil, cyclophosamide, melphalan, ifosfamide, methotrexate, 6-mercaptopurine, 5-fluorouracil, rituximab, bevacizumab, or a combination of any of the foregoing.

15. The method of claim 5, wherein the step of administering the compound comprises administering the compound orally, topically, parentally, intravenously or intramuscularly.

16. The method of claim 8, wherein the compound is

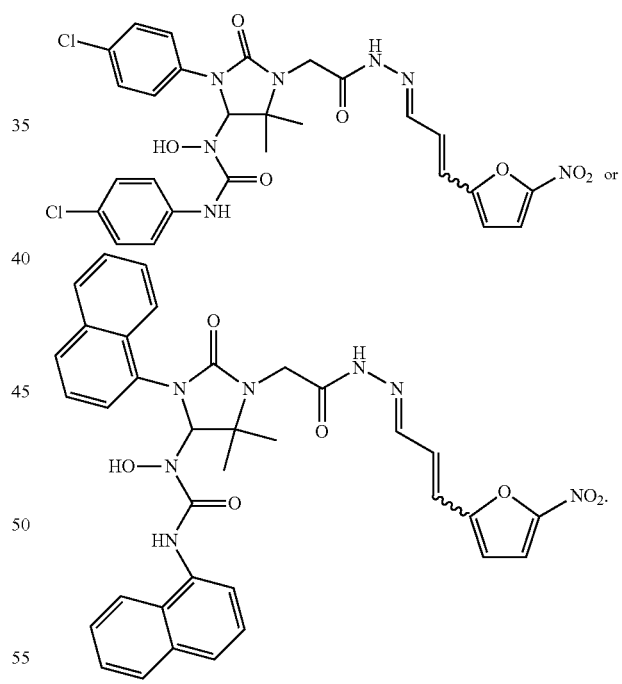

17. The method of claim 5 additionally comprising administering a proteasome inhibitor to the subject.

18. The method of claim 17, wherein the proteasome inhibitor is BORTEZOMIB.

* * * * *